(12) United States Patent
Hossainy et al.

(10) Patent No.: US 7,807,211 B2
(45) Date of Patent: Oct. 5, 2010

(54) THERMAL TREATMENT OF AN IMPLANTABLE MEDICAL DEVICE

(75) Inventors: Syed F. A. Hossainy, Fremont, CA (US); Yiwen Tang, San Jose, CA (US); Manish Gada, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 715 days.

(21) Appl. No.: 10/856,984

(22) Filed: May 27, 2004

(65) Prior Publication Data

US 2005/0233062 A1 Oct. 20, 2005

Related U.S. Application Data

(60) Continuation-in-part of application No. 10/603,794, filed on Jun. 25, 2003, now Pat. No. 7,682,647, and a continuation-in-part of application No. 10/108,004, filed on Mar. 27, 2002, and a continuation-in-part of application No. 10/304,360, filed on Nov. 25, 2002, now abandoned, which is a division of application No. 09/751,691, filed on Dec. 28, 2000, now Pat. No. 6,503,556, application No. 10/856,984, which is a continuation-in-part of application No. 10/751,043, filed on Jan. 2, 2004, now abandoned, which is a continuation of application No. 09/750,595, filed on Dec. 28, 2000, now Pat. No. 6,790,228, which is a continuation-in-part of application No. 09/470,559, filed on Dec. 23, 1999, now Pat. No. 6,713,119, which is a continuation-in-part of application No. 09/390,855, filed on Sep. 3, 1999, now Pat. No. 6,287,628, and a continuation-in-part of application No. 09/390,069, filed on Sep. 3, 1999, now Pat. No. 6,379,381, said application No. 09/750,595 is a continuation-in-part of application No. 09/715,510, filed on Nov. 17, 2000, now Pat. No. 6,749,626, which is a continuation-in-part of application No. 09/540,241, filed on Mar. 31, 2000, now abandoned.

(51) Int. Cl.
  B05D 3/02 (2006.01)
  A61L 27/00 (2006.01)
  A61F 2/06 (2006.01)

(52) U.S. Cl. ............. 427/2.1; 427/2.24; 427/2.25; 427/372.2; 623/1.1; 623/1.42; 623/1.46

(58) Field of Classification Search ............ 427/2.24, 427/2.25, 2.28, 2.1; 525/419; 623/1.1, 1.42, 623/1.44, 1.46
See application file for complete search history.

(56) References Cited

U.S. PATENT DOCUMENTS 2,072,303 A  3/1937  Herrmann et al.

(Continued)

FOREIGN PATENT DOCUMENTS

DE  42 24 401  1/1994

(Continued)

OTHER PUBLICATIONS

Gabriele Perego, Tiziano Vercellio, Copolymers of L and D,L Lactide with 6-caprolactone: synthesis and characterization, Malromol. Chem. 194, 2463-2469 (1993).*

(Continued)

*Primary Examiner*—Timothy H Meeks
*Assistant Examiner*—Cachet I Sellman
(74) *Attorney, Agent, or Firm*—Squire, Sanders & Dempsey L.L.P

(57) ABSTRACT

A method of manufacturing an implantable medical device, such as a drug eluting stent, is disclosed. The method includes subjecting an implantable medical device that includes a polymer to a thermal condition. The thermal condition can result in reduction of the rate of release of an active agent from the device subsequent to the implantation of the device and/or improve the mechanical properties of a polymeric coating on the device.

54 Claims, 19 Drawing Sheets

U.S. PATENT DOCUMENTS

| | | |
|---|---|---|
| 2,386,454 A | 10/1945 | Frosch et al. |
| 3,773,737 A | 11/1973 | Goodman et al. |
| 3,849,514 A | 11/1974 | Gray, Jr. et al. |
| 3,929,992 A | 12/1975 | Sehgal et al. |
| 4,151,413 A | 4/1979 | Arnold |
| 4,226,243 A | 10/1980 | Shalaby et al. |
| 4,316,885 A | 2/1982 | Rakhit |
| 4,325,903 A | 4/1982 | Wissbrun et al. |
| 4,329,383 A | 5/1982 | Joh |
| 4,343,931 A | 8/1982 | Barrows |
| 4,459,252 A | 7/1984 | MacGregor |
| 4,529,792 A | 7/1985 | Barrows |
| 4,611,051 A | 9/1986 | Hayes et al. |
| 4,650,803 A | 3/1987 | Stella et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,059,211 A | 10/1991 | Stack et al. |
| 5,100,883 A | 3/1992 | Schiehser |
| 5,100,992 A | 3/1992 | Cohn et al. |
| 5,102,876 A | 4/1992 | Caufield |
| 5,112,457 A | 5/1992 | Marchant |
| 5,118,677 A | 6/1992 | Caufield |
| 5,118,678 A | 6/1992 | Kao et al. |
| 5,120,725 A | 6/1992 | Kao et al. |
| 5,120,727 A | 6/1992 | Kao et al. |
| 5,120,842 A | 6/1992 | Failli et al. |
| 5,133,742 A | 7/1992 | Pinchuk |
| 5,138,051 A | 8/1992 | Hughes et al. |
| 5,151,413 A | 9/1992 | Caufield et al. |
| 5,162,333 A | 11/1992 | Failli et al. |
| 5,163,952 A | 11/1992 | Froix |
| 5,165,919 A | 11/1992 | Sasaki et al. |
| 5,169,851 A | 12/1992 | Hughes et al. |
| 5,219,980 A | 6/1993 | Swidler |
| 5,221,740 A | 6/1993 | Hughes |
| 5,258,020 A | 11/1993 | Froix |
| 5,258,389 A | 11/1993 | Goulet et al. |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,344,833 A | 9/1994 | Hughes |
| 5,380,299 A | 1/1995 | Fearnot et al. |
| 5,383,928 A | 1/1995 | Scott et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,468,253 A * | 11/1995 | Bezwada et al. ............ 606/230 |
| 5,480,599 A | 1/1996 | Leven et al. |
| 5,485,496 A | 1/1996 | Lee et al. |
| 5,516,881 A | 5/1996 | Lee et al. |
| 5,527,337 A | 6/1996 | Stack et al. |
| 5,527,907 A | 6/1996 | Or et al. |
| 5,569,463 A | 10/1996 | Helmus et al. |
| 5,575,818 A | 11/1996 | Pinchuk |
| 5,578,073 A | 11/1996 | Haimovich et al. |
| 5,583,139 A | 12/1996 | Or et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,651,174 A | 7/1997 | Schwartz et al. |
| 5,658,995 A | 8/1997 | Kohn et al. |
| 5,665,772 A | 9/1997 | Cottens et al. |
| 5,667,767 A | 9/1997 | Greff et al. |
| 5,670,558 A | 9/1997 | Onishi et al. |
| 5,672,605 A | 9/1997 | Or et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,707,867 A | 1/1998 | Glenn |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,766,710 A | 6/1998 | Turnland et al. |
| 5,769,883 A | 6/1998 | Buscemi et al. |
| 5,776,184 A | 7/1998 | Tuch |
| 5,783,657 A | 7/1998 | Pavlin et al. |
| 5,788,979 A | 8/1998 | Alt et al. |
| 5,795,318 A | 8/1998 | Wang et al. |
| 5,798,355 A | 8/1998 | Steiner et al. |
| 5,800,392 A | 9/1998 | Racchini |
| 5,820,917 A | 10/1998 | Tuch |
| 5,824,048 A * | 10/1998 | Tuch .......................... 128/898 |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,843,172 A | 12/1998 | Yan |
| 5,843,960 A | 12/1998 | Steiner et al. |
| 5,846,981 A | 12/1998 | Steiner et al. |
| 5,849,859 A | 12/1998 | Acemoglu |
| 5,851,508 A | 12/1998 | Greff et al. |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,897,911 A | 4/1999 | Loeffler |
| 5,898,029 A | 4/1999 | Lyons et al. |
| 5,902,875 A | 5/1999 | Roby et al. |
| 5,905,168 A | 5/1999 | Dos Santos et al. |
| 5,910,564 A | 6/1999 | Gruning et al. |
| 5,912,253 A | 6/1999 | Cottens et al. |
| 5,914,387 A | 6/1999 | Roby et al. |
| 5,919,893 A | 7/1999 | Roby et al. |
| 5,925,720 A | 7/1999 | Kataoka et al. |
| 5,932,243 A | 8/1999 | Fricker et al. |
| 5,932,299 A | 8/1999 | Katoot |
| 5,955,509 A | 9/1999 | Webber et al. |
| 5,958,385 A | 9/1999 | Tondeur et al. |
| 5,962,007 A | 10/1999 | Cooper et al. |
| 5,962,138 A | 10/1999 | Kolluri et al. |
| 5,968,091 A | 10/1999 | Pinchuk et al. |
| 5,971,954 A | 10/1999 | Conway et al. |
| 5,980,564 A * | 11/1999 | Stinson ..................... 623/23.7 |

| | | | | | | |
|---|---|---|---|---|---|---|
| 5,980,928 | A | 11/1999 | Terry | 6,299,604 B1 | 10/2001 | Ragheb et al. |
| 5,980,972 | A | 11/1999 | Ding | 6,306,176 B1 | 10/2001 | Whitbourne |
| 5,985,890 | A | 11/1999 | Cottens et al. | 6,309,402 B1 | 10/2001 | Jendersee et al. |
| 5,997,517 | A | 12/1999 | Whitbourne | 6,331,313 B1 | 12/2001 | Wong et al. |
| 6,001,117 | A | 12/1999 | Huxel et al. | 6,335,029 B1 | 1/2002 | Kamath et al. |
| 6,010,530 | A | 1/2000 | Goicoechea | 6,344,035 B1 | 2/2002 | Chudzik et al. |
| 6,011,125 | A | 1/2000 | Lohmeijer et al. | 6,346,110 B2 | 2/2002 | Wu |
| 6,013,621 | A | 1/2000 | Nishi et al. | 6,358,556 B1 | 3/2002 | Ding et al. |
| 6,015,541 | A | 1/2000 | Greff et al. | 6,379,381 B1 | 4/2002 | Hossainy et al. |
| 6,015,815 | A | 1/2000 | Mollison | 6,384,046 B1 | 5/2002 | Schuler et al. |
| 6,033,582 | A | 3/2000 | Lee et al. | 6,387,124 B1 | 5/2002 | Buscemi et al. |
| 6,034,204 | A | 3/2000 | Mohr et al. | 6,387,379 B1 | 5/2002 | Goldberg et al. |
| 6,042,875 | A | 3/2000 | Ding et al. | 6,395,326 B1 * | 5/2002 | Castro et al. ................ 427/2.24 |
| 6,051,576 | A | 4/2000 | Ashton et al. | 6,406,739 B1 | 6/2002 | LeBoeuf et al. |
| 6,051,648 | A | 4/2000 | Rhee et al. | 6,419,692 B1 | 7/2002 | Yang et al. |
| 6,054,553 | A | 4/2000 | Groth et al. | 6,451,373 B1 | 9/2002 | Hossainy et al. |
| 6,056,906 | A | 5/2000 | Werneth et al. | 6,475,235 B1 | 11/2002 | Jayaraman |
| 6,056,993 | A | 5/2000 | Leidner et al. | 6,482,834 B2 | 11/2002 | Spada et al. |
| 6,060,451 | A | 5/2000 | DiMaio et al. | 6,494,862 B1 | 12/2002 | Ray et al. |
| 6,060,518 | A | 5/2000 | Kabanov et al. | 6,503,538 B1 | 1/2003 | Chu et al. |
| 6,066,156 | A | 5/2000 | Yan | 6,503,556 B2 | 1/2003 | Harish et al. |
| 6,080,488 | A | 6/2000 | Hostettler et al. | 6,503,954 B1 | 1/2003 | Bhat et al. |
| 6,083,534 | A * | 7/2000 | Wallach et al. ............... 424/484 | 6,506,437 B1 | 1/2003 | Harish et al. |
| 6,096,070 | A | 8/2000 | Ragheb et al. | 6,527,801 B1 | 3/2003 | Dutta |
| 6,099,562 | A | 8/2000 | Ding et al. | 6,527,863 B1 | 3/2003 | Pacetti et al. |
| 6,100,346 | A * | 8/2000 | Jamiolkowski et al. ...... 525/419 | 6,528,526 B1 | 3/2003 | Myers et al. |
| 6,110,188 | A | 8/2000 | Narciso, Jr. | 6,530,950 B1 | 3/2003 | Alvarado et al. |
| 6,110,483 | A | 8/2000 | Whitbourne et al. | 6,530,951 B1 | 3/2003 | Bates et al. |
| 6,113,629 | A | 9/2000 | Ken | 6,540,776 B2 | 4/2003 | Sanders Millare et al. |
| 6,120,491 | A | 9/2000 | Kohn et al. | 6,544,223 B1 | 4/2003 | Kokish |
| 6,120,536 | A | 9/2000 | Ding et al. | 6,544,543 B1 | 4/2003 | Mandrusov et al. |
| 6,120,788 | A | 9/2000 | Barrows | 6,544,582 B1 | 4/2003 | Yoe |
| 6,120,847 | A | 9/2000 | Yang et al. | 6,547,819 B2 | 4/2003 | Strecker |
| 6,120,904 | A | 9/2000 | Hostettler et al. | 6,555,157 B1 | 4/2003 | Hossainy |
| 6,121,027 | A | 9/2000 | Clapper et al. | 6,558,733 B1 | 5/2003 | Hossainy et al. |
| 6,129,761 | A | 10/2000 | Hubbell | 6,565,659 B1 | 5/2003 | Pacetti et al. |
| 6,136,333 | A | 10/2000 | Cohn et al. | 6,572,644 B1 | 6/2003 | Moein |
| 6,139,573 | A | 10/2000 | Sogard et al. | 6,574,497 B1 | 6/2003 | Pacetti |
| 6,143,037 | A | 11/2000 | Goldstein et al. | 6,585,755 B2 | 7/2003 | Jackson et al. |
| 6,143,354 | A | 11/2000 | Koulik et al. | 6,585,765 B1 | 7/2003 | Hossainy et al. |
| 6,153,252 | A | 11/2000 | Hossainy et al. | 6,585,926 B1 | 7/2003 | Mirzaee |
| 6,159,978 | A | 12/2000 | Myers et al. | 6,605,154 B1 | 8/2003 | Villareal |
| 6,165,212 | A | 12/2000 | Dereume et al. | 6,616,765 B1 | 9/2003 | Wu et al. |
| 6,172,167 | B1 | 1/2001 | Stapert et al. | 6,623,448 B2 | 9/2003 | Slater |
| 6,177,523 | B1 | 1/2001 | Reich et al. | 6,623,764 B1 * | 9/2003 | Sokoll et al. ................. 424/501 |
| 6,180,632 | B1 | 1/2001 | Myers et al. | 6,625,486 B2 | 9/2003 | Lundkvist et al. |
| 6,200,985 | B1 | 3/2001 | Cottens et al. | 6,645,135 B1 | 11/2003 | Bhat |
| 6,203,551 | B1 | 3/2001 | Wu | 6,645,195 B1 | 11/2003 | Bhat et al. |
| 6,206,915 | B1 | 3/2001 | Fagan et al. | 6,652,581 B1 | 11/2003 | Ding |
| 6,211,249 | B1 | 4/2001 | Cohn et al. | 6,656,216 B1 | 12/2003 | Hossainy et al. |
| 6,214,901 | B1 | 4/2001 | Chudzik et al. | 6,656,506 B1 | 12/2003 | Wu et al. |
| 6,221,102 | B1 | 4/2001 | Baker et al. | 6,660,034 B1 | 12/2003 | Mandrusov et al. |
| 6,228,934 | B1 | 5/2001 | Horowitz et al. | 6,663,662 B2 | 12/2003 | Pacetti et al. |
| 6,231,600 | B1 | 5/2001 | Zhong | 6,663,880 B1 | 12/2003 | Roorda et al. |
| 6,240,616 | B1 | 6/2001 | Yan | 6,666,880 B1 | 12/2003 | Chiu et al. |
| 6,245,753 | B1 | 6/2001 | Byun et al. | 6,673,154 B1 | 1/2004 | Pacetti et al. |
| 6,245,760 | B1 | 6/2001 | He et al. | 6,673,385 B1 | 1/2004 | Ding et al. |
| 6,248,129 | B1 | 6/2001 | Froix | 6,689,099 B1 | 2/2004 | Mirzaee |
| 6,251,136 | B1 | 6/2001 | Guruwaiya et al. | 6,695,920 B1 | 2/2004 | Pacetti et al. |
| 6,254,632 | B1 | 7/2001 | Wu et al. | 6,706,013 B1 | 3/2004 | Bhat et al. |
| 6,258,121 | B1 | 7/2001 | Yang et al. | 6,709,514 B1 | 3/2004 | Hossainy |
| 6,258,371 | B1 | 7/2001 | Koulik et al. | 6,712,845 B2 | 3/2004 | Hossainy |
| 6,262,034 | B1 | 7/2001 | Mathiowitz et al. | 6,713,119 B2 | 3/2004 | Hossainy et al. |
| 6,270,788 | B1 | 8/2001 | Koulik et al. | 6,716,444 B1 | 4/2004 | Castro et al. |
| 6,273,913 | B1 | 8/2001 | Wright et al. | 6,723,120 B2 | 4/2004 | Yan |
| 6,277,449 | B1 | 8/2001 | Kolluri et al. | 6,733,768 B2 | 5/2004 | Hossainy et al. |
| 6,281,225 | B1 | 8/2001 | Hearst et al. | 6,739,033 B2 | 5/2004 | Hijlkema et al. |
| 6,283,947 | B1 | 9/2001 | Mirzaee | 6,740,040 B1 | 5/2004 | Mandrusov et al. |
| 6,283,949 | B1 | 9/2001 | Roorda | 6,743,462 B1 | 6/2004 | Pacetti |
| 6,284,305 | B1 | 9/2001 | Ding et al. | 6,749,626 B1 | 6/2004 | Bhat et al. |
| 6,284,788 | B1 | 9/2001 | Mittendorf et al. | 6,753,071 B1 | 6/2004 | Pacetti |
| 6,287,628 | B1 | 9/2001 | Hossainy et al. | 6,758,859 B1 | 7/2004 | Dang et al. |
| 6,293,959 | B1 | 9/2001 | Miller et al. | 6,759,054 B2 | 7/2004 | Chen et al. |

| | | |
|---|---|---|
| 6,764,505 B1 | 7/2004 | Hossainy et al. |
| 6,823,576 B2 | 11/2004 | Austin |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 6,948,223 B2 | 9/2005 | Shortt |
| 7,077,859 B2 | 7/2006 | Sirhan et al. |
| 7,291,165 B2 | 11/2007 | Rosenthal et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0046518 A1 | 11/2001 | Sawhney |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0082685 A1* | 6/2002 | Sirhan et al. ............... 623/1.42 |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0127263 A1* | 9/2002 | Carlyle et al. ............... 424/423 |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |

| | | |
|---|---|---|
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0220665 A1 | 11/2004 | Hossainy et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2005/0118344 A1 | 6/2005 | Pacetti |
| 2005/0119720 A1 | 6/2005 | Gale et al. |
| 2005/0233062 A1 | 10/2005 | Hossainy et al. |

FOREIGN PATENT DOCUMENTS

| | | |
|---|---|---|
| EP | 0 301 856 | 2/1989 |
| EP | 0 323 042 | 7/1989 |
| EP | 0 396 429 | 11/1990 |
| EP | 0 401 747 | 12/1990 |
| EP | 0 414 632 | 2/1991 |
| EP | 0 475 230 | 3/1992 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 875 218 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 978 288 | 2/2000 |
| EP | 0 982 041 | 3/2000 |
| EP | 1 023 879 | 8/2000 |
| EP | 1 036 562 | 9/2000 |
| EP | 1 064 942 | 1/2001 |

| | | |
|---|---|---|
| EP | 1 192 957 | 4/2002 |
| EP | 1 273 314 | 1/2003 |
| JP | 11299901 | 11/1999 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 90/01969 | 3/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 95/31104 | 11/1995 |
| WO | WO 96/13273 | 5/1996 |
| WO | WO 96/40140 | 12/1996 |
| WO | WO 96/40174 | 12/1996 |
| WO | WO 97/03654 | 2/1997 |
| WO | WO 97/10011 | 3/1997 |
| WO | WO 97/31020 | 8/1997 |
| WO | WO 97/45105 | 12/1997 |
| WO | WO 97/46590 | 12/1997 |
| WO | WO 98/02441 | 1/1998 |
| WO | WO 98/04256 | 2/1998 |
| WO | WO 98/08463 | 3/1998 |
| WO | WO 98/09523 | 3/1998 |
| WO | WO 98/10747 | 3/1998 |
| WO | WO 98/17331 | 4/1998 |
| WO | WO 98/23228 | 6/1998 |
| WO | WO 98/32398 | 7/1998 |
| WO | WO 98/36784 | 8/1998 |
| WO | WO 98/44921 | 10/1998 |
| WO | WO 98/44922 | 10/1998 |
| WO | WO 99/01118 | 1/1999 |
| WO | WO 99/16386 | 4/1999 |
| WO | WO 99/19471 | 4/1999 |
| WO | WO 99/19473 | 4/1999 |
| WO | WO 99/24036 | 5/1999 |
| WO | WO 99/38546 | 8/1999 |
| WO | WO 99/39720 | 8/1999 |
| WO | WO 99/42104 | 8/1999 |
| WO | WO 99/44584 | 9/1999 |
| WO | WO 99/44597 | 9/1999 |
| WO | WO 99/60997 | 12/1999 |
| WO | WO 99/61040 | 12/1999 |
| WO | WO 99/63981 | 12/1999 |
| WO | WO 00/02599 | 1/2000 |
| WO | WO 00/09085 | 2/2000 |
| WO | WO 00/12147 | 3/2000 |
| WO | WO 00/15208 | 3/2000 |
| WO | WO 00/18446 | 4/2000 |
| WO | WO 00/24390 | 5/2000 |
| WO | WO 00/32234 | 6/2000 |
| WO | WO 00/32238 | 6/2000 |
| WO | WO 00/33878 | 6/2000 |
| WO | WO 00/38590 | 7/2000 |
| WO | WO 00/38703 | 7/2000 |
| WO | WO 00/38754 | 7/2000 |
| WO | WO 00/42949 | 7/2000 |
| WO | WO 00/56247 | 9/2000 |
| WO | WO 00/57818 | 10/2000 |
| WO | WO 00/64506 | 11/2000 |
| WO | WO 00/66122 | 11/2000 |
| WO | WO 00/71052 | 11/2000 |
| WO | WO 00/74665 | 12/2000 |
| WO | WO 01/01890 | 1/2001 |
| WO | WO 01/14387 | 3/2001 |
| WO | WO 01/15751 | 3/2001 |
| WO | WO 01/17577 | 3/2001 |
| WO | WO 01/23395 | 4/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/035131 | 5/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/004945 | 1/2005 |

OTHER PUBLICATIONS

Van de Velde et al. Biopolymers; overview of several properties and consequences on their applications. Polymer Testing vol. 21 (2002) pp. 433-442.*

Anonymous, *A Simple Approach for Glass Transition Temperature Prediction*, http://www.geocities.com/ResearchTriangle/Thinktank/4146/6400glass-temperature.html, printed May 5, 2005 (2 pages).

Anonymous, *Appendix I—Glass Transition Temperature ($T_g$)* www.Dymax.com/pdf/SPIE-Paper-Apendix.pdf, printed May 9, 2005 (2 pages).

Anonymous, *Cardiologists Draw—Up the Dream Stent*, Clinica 710:15 (Jun. 17, 1996), http://www.dialogweb.com/cgi/document?reg=1061848202959, printed Aug. 25, 2003 (2 pages).

Anonymous, *Differential Scanning Calorimetry*, http://www:pslc.ws/macrog/dsc.htm, printed May 9, 2005 (8 pages).

Anonymous, *Glass transition temperature*, http://palimpsest.stanford.edu/don/dt/dt1549.html, printed May 5, 2005 (1 page).

Anonymous, *Glass Transition Temperature*, http://islnotes.cps.msu.edu/trp/back/mol_glas.html, printed May 5, 2005 (1 page).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *How Big are Polymers?* www.chemeng.ucla.edu/che112/Notes, printed May 9, 2005, (13 pages).

Anonymous, *Measuring and Understanding Tg (Glass Transition Temperature)*, Arlon, Application Notes (4 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Anonymous, *The Glass Transition*, http://www.pslc.ws/macrog/tg.htm printed May 18, 2005 (11 pages).

Anonymous, *Thermoplastics—An Introduction*, http://www.azom.com/details.asp?ArticleID+83&head=Thermoplastics%2B-%2BAn%2BIntroduction, printed May 18, 2005 (5 pages).

Aoyagi et al., *Preparation of cross-linked aliphatic polyester and application to thermo-responsive material*, Journal of Controlled Release 32:87-96 (1994).

Arvanitoyannis et al., *Novel star-shaped polylactide with glycerol using stannous octoate or tetraphenyl tin as catalyst: 1 Synthesis, characterization and study of their biodegradability*, Polymer vol. 36, No. 15, pp. 2947-2956 (1995).

Baird et al, *Dielectric behaviour and morphology of polyvinylidene fluoride*, Journal of Material Science 10:1248-1251 (1975).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Birmingham Polymers, Inc., DLPLA IV vs. Mw, http://www.birminahampolymers.com/htdocs/dIpla.htm, printed Apr. 26, 2004 (1 page).

Birmingham Polymers, Inc., Standard Products, http://www.birminghamoolymers.com/htdocs/Standard_Products.htm, printed Apr. 26, 2004 (2 pages).

Birmingham Polymers, Inc., *Physical Properties of Selected Polymers*, http://www.birminghampolymers.com/htdocs/physical_properties.htm, printed Apr. 26, 2004(2 pages).

Birmingham Polymers, Inc., *Chemical Properties of Selected Polymers*, http://www.birminghampolymers.com/htdocs/Chemical Properties.htm, printed May 19, 2005 (2 pages).

Birmingham Polymers, Inc., *Biodegradation Information*, http://www.birminghampolymers.com/htdocs/biodegradation.htm, printed Apr. 26, 2004 (2 pages).

Black et al., *Glass Transitions of Some Block Copolymers*, Journal of Applied Polymer Science 18:2307-2310 (1974).

Bliznyuk et al., *Surface Glass Transition Temperature of Amorphous Polystyrene Measured by SFM*, pp. 1-5.

Bloembergen et al., *Studies of Composition and Crystallinity of Bacterial Poly(β-hydroxybutyrate-co-βhydroxyvalerate)*, Macromolecules 19, pp. 2865-2871 (1986).

Buchholz et al., *Cooling rate dependence of the glass transition temperature of polymer melts: Molecular dynamics study*, Journal of Chemical Physics 117(15):7364-7372 (Oct. 15, 2002).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5)1347-1353 (Nov. 1989).

Ding et al., *Novel Synthesis of Poly(p-phenylene sulfide) from Cyclic Disulfide Oligomers*, Macromolecules 29:4811-4812 (1996).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Eling et al., *Biodegradable materials of poly(L-lactic acid): 1. melt-spun and solution-spun fibres*, Polymer, vol. 23, pp. 1587-1593 (1982).

Fernandez-Martin et al., *Glass Transition Temperature and Heat Capacity of Heterotacticlike PMMA*, Journal of Polymer Science: Polymer Physics Edition 19:1353-1363 (1981).

Forrest et al., *Effect of Free Surfaces on the Glass Transition Temperature of Thin Polymer Films*, Physical Review Letters 77(10):2002-2005 (Sep. 2, 1996).

Fryer et al., *Dependence of the Glass Transition Temperature of Polymer Films on Interfacial Energy and Thickness*, Macromolecules 34(16):5627-5634 (2001).

Fujii et al., *Investigation of the Stereoregularity of Poly(vinyl Alcohol)*, Journal of Polymer Science: Part A 2:2327-2347 (1964).

Gee et al., *The effect of ionizing radiation on the thermal properties of linear high polymers: Part 2. Nylon-6*, pp. 192-197 (1970).

Grohens et al., *Tacticity and surface chemistry effects on the glass transition temperature of thin supported PMMA films*, Mat. Res. Soc. Symp. 629:FF1.7.1-FF1.7.7 (2000).

*Guidant Licenses Everolimus From Novartis for Drug Eluting Stents* (Press Release, Mar. 27, 2002), http//biz.yahoo.com/bw/020327/272460_1.html, printed Mar. 27, 2002 (2 pages).

Helmus, *Overview of Biomedical Materials*, MRS Bulletin, pp. 33-38 (1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

*International Nonproprietary Names for Pharmaceutical Substances (INN)*, WHO Drug Information 14(3):183, 184, 194 (2000) (3 pages).

International Search Report and Written Opinion for PCT/US2004/017060, filed May 28, 2004, mailed Dec. 30, 2004, 10 pgs.

Jacobsen et al., *Filling of Poly(Lactic Acid) With Native Starch*, Polymer Engineering and Science, vol. 36, No. 22, pp. 2799-2804 (1996).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

*KYNAR® and KYNAR®FLEX PVDF, The Base Resins for Demanding Industrial Applications*, http://www.products.arkemagroup.com/print.cfm, printed May 18, 2005 (3 pages).

Lam et al., *Biodegradation of porous versus non-porous poly(L-lactic acid) films*, J. of Materials Science: Materials Medicine 5, pp. 181-189 (1994).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Löfgren et al., *Synthesis and Characterization of Biodegradable Homopolymers and Block Copolymers ,Based on 1,5-Dioxepan-2-one*, Macromolecules 27:5556-5562 (1994).

Liu et al., *Drug release characteristics of unimolecular polymeric micelles*, Journal of Controlled Release 68:167-174 (2000).

Lotz, *Phase Transitions and Structure of Crystalline Polymers*, pp. 1-27.

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Micoulaut et al., *Glass Transition temperature variation, cross-linking and structure in network glasses: A stochastic approach*, Europhysics Letters 47(5):568-574 (1999).

Migliaresi et al., *Dynamic Mechanical and Calorimetric Analysis of Compression-Molded PLLA of Different Molecular Weights: Effect of Thermal Treatments*, J. of Applied Polymer Science, vol. 43, pp. 83-95 (1991).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nijenhuis et al., *Highly crystalline as-polymerized poly(L-lactide)*, Polymer bulletin 26, pp. 71-77 (1991).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Parravicini et al., *Crystallization of Poly(Ethylene Terephthalate) (PET) from the Oriented Mesomorphic Form*, pp. 875-885 (1994).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Reeve et al., *Polylactide Stereochemistry:Effect on Enzymatic Degradability*, Macromolecules 27, pp. 825-831 (1994).

Rogers et al., *Glass Formation in Polymers. I. The Glass Transitions of the Poly-(n-Alkyl Methacrylates)*, 61:985-990 (Jul. 1957).

Saotome, et al., *Novel Enzymatically Degradable Polymers Comprising α-Amino Acid, 1,2-Ethanediol, and Adipic Acid*, Chemistry Letters, pp. 21-24, (1991).

Sarasua et al., *Crystallization and Melting Behavior of Polylactides*, Macromolecules 31, pp. 3895-3905 (1998).

Scott et al., *Ehtylene-Vinyl Acetate Semi-Batch Emulsion Copolymerization: Use of Factorial Experiments for Process Optimization*, pp. 539-555 (1993).

Shigeno, *Prevention of Cerebrovascular Spasm by Bosentan, Novel Endothelin Receptor*; Chemical Abstract 125:212307 (1996).

Sichina, *Characterization of Polymers by TMA*, Perkin Elmer Polymers technical note (9 pages).

Sun et al., *Novel Copolyesters Containing Naphthalene Structure. I. From Bis(hydroxyalkyl)naphthalate and Bis[4-(2-hydroxyethoxy)aryl] Compounds*, Journal of Polymer Science: Part A: Polymer Chemistry 34:1783-1792 (1996).

Taylor et al., *An Applied Approach to Film Formation; The glass transition temperature evolution of plasticized latex films*, downloaded May 5, 2005 (13 pages).

TECHSPRAY Product Information, *HFE Flux Remover*, http://www.techspray.com/1686info.htm, printed May 9, 2005 (2 pages).

Tsige et al., *Simulation study of the glass transition temperature in poly(methyl methacrylate)*, Physical Review E vol. 65: (2002) (8 pages).

*Transplant 2001: Certican (Everolimus) Effective in Preventing Acute Rejection in Renal Transplantation*, http://www.docguide.com/dg.nsf/PrintPrint/A9A24F321A71712485256A4E00689824, printed May 9, 2005.

van Beusekom et al., *Coronary stent coatings*, Coronary Artery Disease 5(7): 590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

European Search Report for 05780079.9-2107, mailed Jan. 17, 2008, 6 pages.

EPO Examination Report for application 04 812 597.5-2307, mailed May 26, 2007, 2 pgs.

EPO Examination Report for application 04 812 597.5-2307, mailed Sep. 6, 2007, 3 pgs.

EPO Examination Report for application 04 812 597.5-2307, mailed Jul. 4, 2008, 3 pgs.

International Search Report and Written Opinion for PCT/US2004/040121, filed Nov. 30, 2004, mailed Apr. 12, 2005, 12 pgs.

International Search Report and Written Opinion for PCT/US2004/017060, filed May 28, 2004, mailed Dec. 30, 2004, 10 pgs.

International Search Report for PCT/US2005/018579 filed May 26, 2005, mailed May 24, 2006, 16 pages.

\* cited by examiner

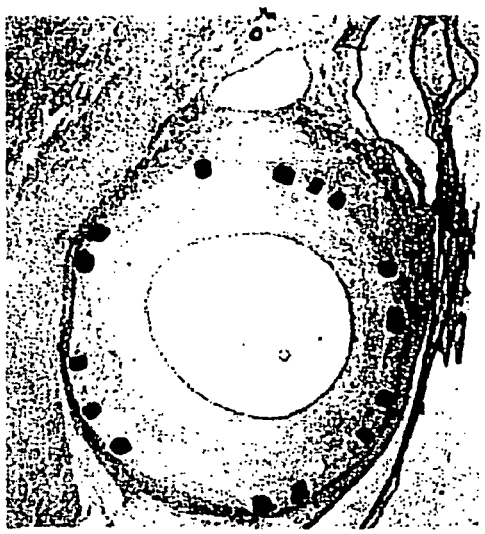 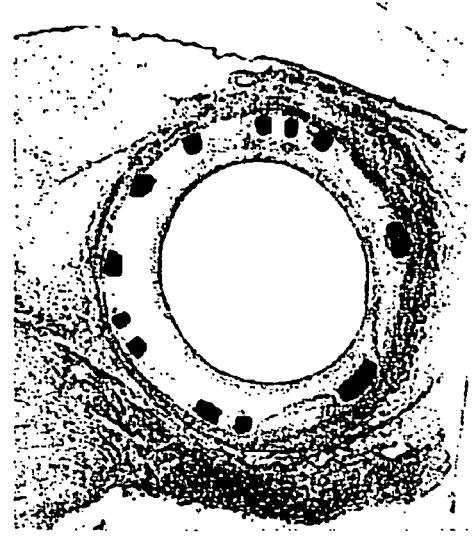
FIG. 9A       FIG. 9B
FIG. 10A

THERMAL TREATMENT OF AN IMPLANTABLE MEDICAL DEVICE

CROSS REFERENCE

This application is a continuation-in-part of U.S. patent application Ser. No. 10/603,794, filed on Jun. 25, 2003, and which issued as U.S. Pat. No. 7,682,647 on Mar. 23, 2010. This application is also a continuation-in-part of U.S. patent application Ser. No. 10/108,004, which was filed on Mar. 27, 2002. Furthermore, this application is a continuation-in-part of U.S. patent application Ser. No. 10/304,360, now abandoned filed on Nov. 25, 2002, which is a divisional application of U.S. patent application Ser. No. 09/751,691, filed on Dec. 28, 2000, and which issued as U.S. Pat. No. 6,503,556 on Jan. 7, 2003. Additionally, this application is a continuation-in-part of U.S. patent application Ser. No. 10/751,043, now abandoned, filed on Jan. 2, 2004, which is a continuation of U.S. patent application Ser. No. 09/750,595, filed on Dec. 28, 2000, and which issued as U.S. Pat. No. 6,790,228 on Sep. 14, 2004. U.S. patent application Ser. No. 09/750,595, is a continuation-in-part of U.S. patent application Ser. No. 09/470,559, filed on Dec. 23, 1999, which issued as U.S. Pat. No. 6,713,119 on Mar. 30, 2004, and which is a continuation-in-part of U.S. application Ser. No. 09/390,855, filed on Sep. 3, 1999 and issuing as U.S. Pat. No. 6,287,628 on Sep. 11, 2001, and which is also a continuation-in-part of U.S. patent application Ser. No. 09/390,069, filed on Sep. 3, 1999, and issuing U.S. Pat. No. 6,379,381 on Apr. 30, 2002. U.S. patent application Ser. No. 09/750,595 is also a continuation-in-part of U.S. patent application Ser. No. 09/715,510, filed on Nov. 17, 2000 and issuing as U.S. Pat. No. 6,749,626 on Jun. 15, 2004, which is a continuation-in-part of U.S. patent application Ser. No. 09/540,241, now abandoned, filed on Mar. 31, 2000.

BACKGROUND OF THE INVENTION

1. Field of the Invention

The invention relates to implantable medical devices, one example of which is a stent. More particularly, the invention relates to a method of thermally treating an implantable medical device that includes a polymer, for example, a polymeric coating on the device.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Mechanical intervention via stents has reduced the rate of restenosis as compared to balloon angioplasty. Yet, restenosis is still a significant clinical problem with rates ranging from 20-40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method of medicating stents involves the use of a polymeric carrier coated onto the surface of the stent. A composition including a solvent, a polymer dissolved in the solvent, and an active agent dispersed in the blend is applied to the stent by immersing the stent in the composition or by spraying the composition onto the stent. The solvent is allowed to evaporate, leaving on the stent strut surfaces a coating of the polymer and the active agent impregnated in the polymer.

A stent coating can be exposed to significant stress, for example, radial expansion as the stent is deployed. A potential shortcoming of the foregoing method of medicating stents is that the mechanical integrity of a polymeric drug coating can fail in the biological lumen, for example as a result of stress. In some instances, the polymeric coating may have poor adhesion to the surface of the stent. In other instances, if the polymeric coating contains multiple layers of materials, the different layers may not attach well to each other and lack sufficient cohesiveness. Poor cohesion can result if there is inadequate interfacial compatibility between the surface of the stent and the polymer in the coating.

Failure of the mechanical integrity of the polymeric coating while the stent is localized in a patient can lead to a serious risk of embolization because a piece of the polymeric coating can tear or break off from the stent. Polymeric stent coatings having a high drug loading are especially vulnerable to fracture during and after deployment.

It is desirable to provide a polymeric coating that has improved adhesion to the surface of the stent. It also is desirable to improve the cohesion of multiple layers of polymeric material on a stent. Moreover, it is desirable to be able to increase the quantity of the therapeutic substance carried by the polymeric coating without perturbing the mechanical properties of the coating or significantly increasing the thickness of the coating.

Another potential shortcoming of the foregoing method of medicating stents is that the release rate of the active agent may be too high to provide an efficacious treatment. This shortcoming may be especially pronounced with certain active agents. For instance, it has been found that the release rate of 40-O-(2-hydroxy)ethyl-rapamycin from a standard polymeric coating is greater than 50% in about 24 hours.

Thus, there is a need for a coating that reduces the release rate of active agents in order to provide a more efficacious release rate profile.

Yet another shortcoming is that there can be significant manufacturing inconsistencies. For instance, there can be release rate variability among different stents. It is believed that when some polymers dry on a stent surface to form a coating, different polymer morphologies can develop for different stent coatings, even if the coating process parameters are consistent. The differences in polymer morphology may cause the release rate of the active agent from the polymeric coatings to vary significantly. As a consequence of the inconsistent release rate profiles among stents, there can be clinical complications. Additionally, when stents are stored, the release rate from the stent coating can change during the storage time, known as "release rate drift." Thus, there is a need for a method that reduces the variability of the release rate of active agents among stents and over time.

The present invention provides a method and coating to meet the foregoing as well as other needs.

SUMMARY

According to one aspect of the present invention, a method of coating an implantable medical device is disclosed, the method including applying a composition to an implantable medical device, the composition including a polymer component and a solvent; and heating the polymer component to a temperature equal to or greater than the glass transition temperature of the polymer component. In one embodiment, the temperature is (a) equal to the glass transition temperature of the polymer component plus the melting temperature of the polymer component, divided by 2; (b) equal to 0.9 times the melting temperature of the polymer component, wherein the melting temperature of the polymer component is expressed in Kelvin; (c) less than the melting temperature of the polymer component; (d) greater than the melting temperature of the polymer component; or (e) equal to or greater than the crystallization temperature of the polymer component. In another embodiment, the polymer component is heated at a temperature equal to or greater than the glass transition temperature until a dry coating is formed on the device and optionally for a period of time thereafter, the dry coating comprising (a) less than about 10% residual solvent or water (w/w); (b) less than about 2% residual solvent or water (w/w); (c) less than about 1% residual solvent or water (w/w); or (d) 0% residual solvent or water (w/w). In one embodiment, the composition is free of any active agents, while in another embodiment, the composition further includes an active agent.

According to another aspect, a method of manufacturing an implantable medical device is disclosed, the method including applying a semicrystalline polymer to an implantable medical device; and exposing the polymer to a temperature equal to or greater than the crystallization temperature of the polymer for a duration of time. In one embodiment, the polymer includes poly(lactic acid). In another embodiment, the polymer includes a block copolymer or a graft copolymer, wherein a moiety of the block copolymer or the graft copolymer is poly(lactic acid).

In another aspect, a method of manufacturing a stent having a body made at least in part from a polymer component is disclosed, the method comprising exposing the polymer component to a temperature equal to or greater than the glass transition temperature of the polymer component. In one embodiment, the stent is a biodegradable stent.

According to a further aspect, a method of manufacturing an implantable medical device is disclosed, the method including forming a first region including a first polymer on the device; forming a second region of a second polymer on the device, the second region including an active agent, the first region being over or under the second region; and heating (i) the first polymer to a temperature equal to or above the glass transition temperature of the first polymer, or (ii) the second polymer to a temperature equal to or above the glass transition temperature of the second polymer. In one embodiment, the first polymer has a glass transition temperature greater than the second polymer. In another embodiment, the second polymer has a glass transition temperature greater than the first polymer.

In yet another aspect, a method of manufacturing a stent coating is disclosed, the method including applying a composition to a stent, the composition including a polymer and a solvent; allowing some, most or all of the solvent to evaporate to form a coating; and exposing the coating to a temperature sufficient to increase the crystallinity of the polymer in at least a portion of the coating.

In a further aspect of the present invention, a method of manufacturing an implantable medical device is disclosed, the device including a polymer and a drug, where the method comprises treating the device to a temperature greater than ambient temperature for a duration of time, wherein the temperature and the duration of exposure are sufficient to decrease the release rate of the drug from the device after the device has been implanted into a biological lumen. In one embodiment, the device is made in whole or in part from the polymer. In another embodiment, the polymer is biodegradable. In yet another embodiment, the standard deviation of the mean release rate of the drug in a 24 hour period is lower than the standard deviation of the mean release rate for a group of devices which have not been exposed to the temperature.

In yet another aspect, a method of manufacturing a coating for an implantable medical device is disclosed, the method including exposing a polymeric coating on the device to a temperature greater than ambient temperature for a duration of time, wherein the temperature and the duration of exposure is sufficient to increase the adhesion of the polymeric coating to the device. In one embodiment, the polymeric coating is free from any active agents. In another embodiment, the polymeric coating includes an amorphous polymer. In yet another embodiment, the polymeric coating includes a bioabsorable polymer.

In a further aspect of the present invention, a method of forming a coating for an implantable medical device is disclosed, the method including (a) applying a first composition including a first polymer and a solvent on the device; (b) heating the first polymer to a temperature equal to or greater than about the glass transition temperature of the first polymer; (c) applying a second composition including a second polymer and a solvent over the first polymer; and (d) heating the second polymer to a temperature equal to or greater than about the glass transition temperature of the second polymer. In one embodiment, the heating of the first polymer is conducted after removal of some, most or all of the solvent in the first composition. In another embodiment, the heating of the second polymer is conducted after removal of some, most or all of the solvent in the second composition. In yet another embodiment, the first or the second composition, but not both, additionally include an active agent.

BRIEF DESCRIPTION OF THE FIGURES

FIG. 9A is a picture of a histology slide of a coronary vessel from the control group in accordance with Example 16;

FIG. 9B is a picture of a histology slide of a coronary vessel from the actinomycin D group in accordance with Example 16;

FIG. 10A is a picture of a histology slide of a coronary vessel from the control group in accordance with Example 26;

DETAILED DESCRIPTION

Herein is disclosed a method of manufacturing an implantable medical device, such as a stent, by using a thermal treatment process. The implantable medical device manufactured in accordance with embodiments of the present invention may be any suitable medical substrate that can be implanted in a human or veterinary patient. In the interests of brevity, methods of manufacturing a drug delivery or drug eluting stent are described herein. However, one of ordinary skill in the art will understand that other medical substrates can be manufactured using the methods of the present invention. For example, the thermal treatment process can be directed to an implantable medical device having a body that includes a polymer, and optionally, a drug. In one embodiment, the polymer is biodegradable, bioabsorbable or bioerodable. The embodiments directed to a coating are equally applicable to a device, such as a stent, made from a polymer or a combination of polymers.

Coating

The thermal treatment process described herein includes exposing (i.e., heating) a polymer contained in a coating. In one aspect of the present invention, the polymer is exposed to a temperature sufficient to increase the adhesion of a coating to an implantable medical device. In another aspect, the polymer is exposed to a temperature sufficient to decrease the release rate of an active agent from a drug coating on an implantable medical device. "Polymer," "poly," and "polymeric" are inclusive of homopolymers, copolymers, terpolymers etc., including random, alternating, block, cross-linked, blends and graft variations thereof. The active agent can be any substance capable of exerting a therapeutic or prophylactic effect.

Some of the embodiments of polymeric coatings are illustrated by FIGS. 1A-1H. The Figures have not been drawn to scale, and the thickness of the various layers have been over or under emphasized for illustrative purposes.

Figure 1A:
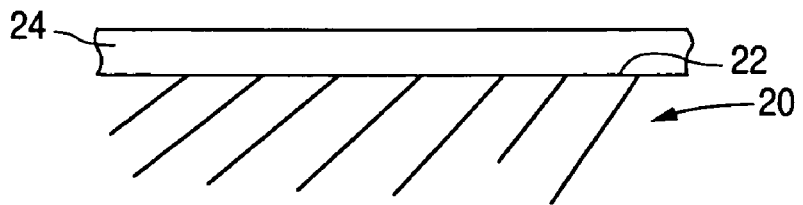
FIGS. 1A-1H illustrate coatings deposited on an implantable medical substrate in accordance with various embodiments of the present invention.

Referring to FIG. 1A, a body of a medical substrate 20, such as a stent, is illustrated having a surface 22. A primer layer 24 is deposited on surface 22. The polymer in primer layer 24 is free of any active agents, although incidental active agent migration into primer layer 24 can occur. Primer layer 24 can include a poly(lactic acid).

Figure 1B:
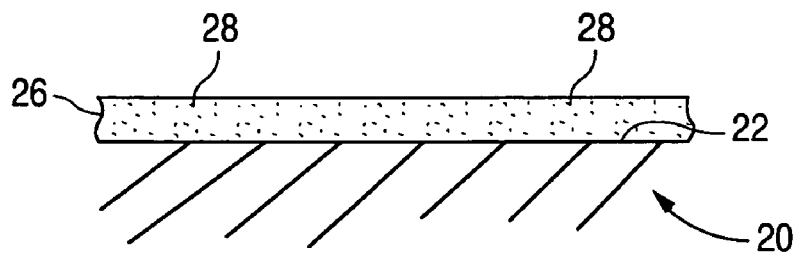

Referring to FIG. 1B, a reservoir layer 26 having a polymer and an active agent 28 (e.g., 40-O-(2-hydroxy)ethyl-rapamycin, known by the trade name of everolimus, available from Novartis as Certican™) dispersed in the polymer is deposited on surface 22. Reservoir layer 26 can release the active agent when medical substrate 20 is inserted into a biological lumen.

Figure 1C:
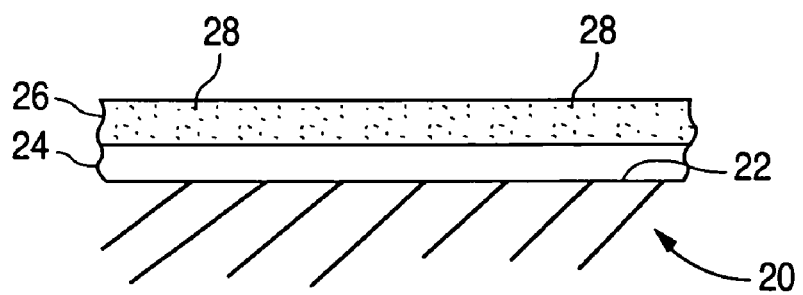

Referring to FIG. 1C, reservoir layer 26 is deposited on primer layer 24. Primer layer 24 serves as an intermediary layer for increasing the adhesion between reservoir layer 26 and surface 22. Increasing the amount of active agent 28 admixed within the polymer can diminish the adhesiveness of reservoir layer 26 to surface 22. Accordingly, using an active agent-free polymer as an intermediary primer layer 24 allows for a higher active agent content for reservoir layer 26.

Figure 1D:
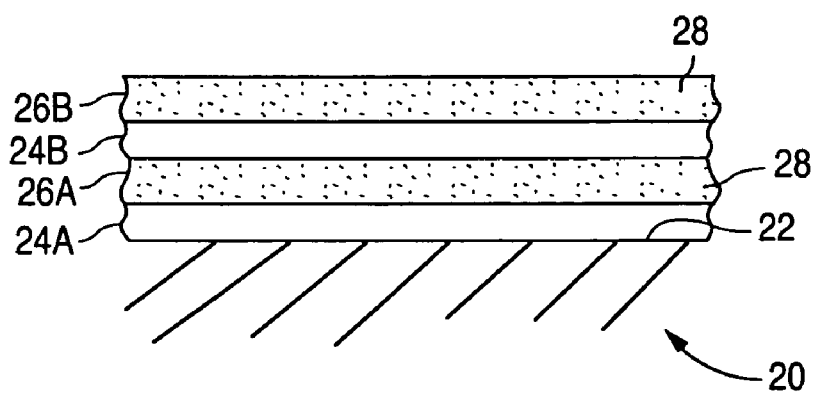

The coating of the present invention can also have multiple primer and reservoir layers, the layers alternating between the two types of layers through the thickness of the coating. Referring to FIG. 1D, for instance, medical substrate 20 can have primer layer 24A deposited on surface 22, followed by reservoir layer 26A deposited on primer layer 24A. A second primer layer, primer layer 24B, can then be deposited on reservoir layer 26A. Reservoir layer 26B is deposited over primer layer 24B. The different layers through the thickness of the coating can contain the same or different components. For instance, primer layers 24A and 24B can contain the same or different polymers. Furthermore, reservoir layers 26A and 26B can contain the same or different polymers and/or active agents.

Figure 1E:
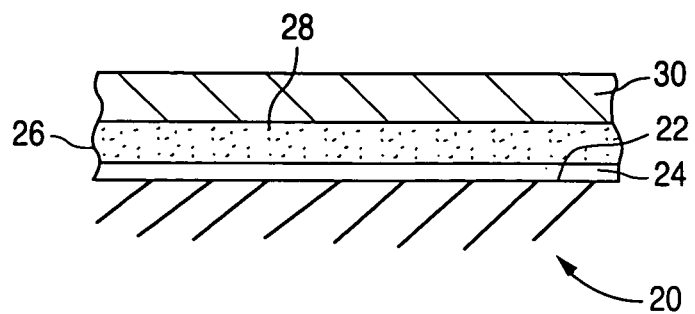
Figure 1F:
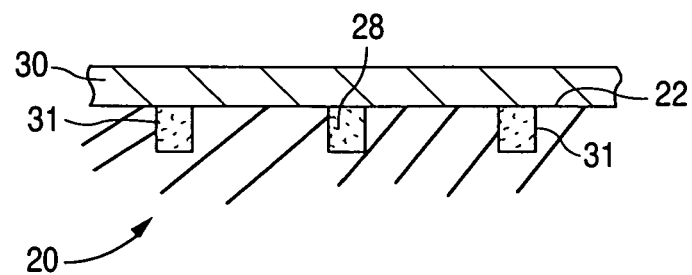
Figure 1G:
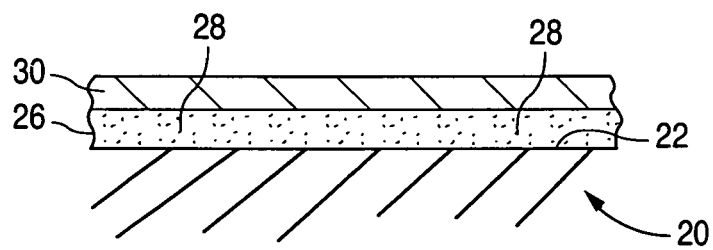

The coating can also include a barrier layer. Referring to FIG. 1E, medical substrate 20 is illustrated having reservoir layer 26 deposited on primer layer 24. A barrier layer or rate-reducing membrane 30 including a polymer is formed over at least a selected portion of reservoir layer 26. Barrier layer 30 functions to reduce the rate of release of active agent 28 from medical substrate 20.

As previously shown in FIG. 1B, the coating can be constructed without a primer layer. For instance, referring to FIG. 1F, medical substrate 20 includes cavities or micro-pores 31 formed in the body for releasably containing active agent 28.

Barrier layer 30 is disposed on surface 22 of medical substrate 20, covering cavities 31. Barrier layer 30 can reduce the rate of release of active agent 28 from micropores 31. Furthermore, referring to FIG. 1G, medical substrate 20 is illustrated having reservoir layer 26 deposited on surface 22. Barrier layer 30 is formed over at least a selected portion of reservoir layer 26.

Figure 1H:
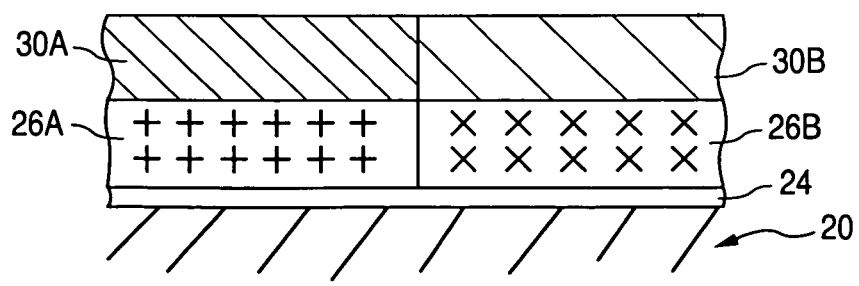

One of ordinary skill in the art can appreciate that the coating can be constructed to provide for a variety of selected release parameters. Such selected patterns may become particularly useful if a combination of active agents is used, each of which requires a different release parameter. FIG. 1H illustrates, for example, medical substrate 20 having a first reservoir layer 26A disposed on a selected portion of primer layer 24. First reservoir layer 26A contains a first active agent, e.g., 40-O-(2-hydroxy)ethyl-rapamycin. A second reservoir layer 26B can also be disposed on primer layer 24. Second reservoir layer 26B contains a second active agent, e.g., taxol. First and second reservoir layers 26A and 26B are covered by first and second barrier layers 30A and 30B, respectively. The particular components of reservoir layers 26A and 26B, and barrier layers 30A and 30B, can be selected so that the release rate of the active agent from first reservoir layer 26A is different or the same than the release rate of the active agent from second reservoir layer 26B.

By way of example, and not limitation, primer layer 24 can have any suitable thickness, examples of which can be in the range of about 0.1 to about 10 microns, more narrowly about 0.1 to about 1 micron. Reservoir layer 26 can have any suitable thickness, for example, a thickness of about 0.1 microns to about 10 microns, more narrowly about 0.5 microns to about 6 microns. The amount of the active agent to be included on medical substrate 20 can be further increased by applying a plurality of reservoir layers 24 on top of one another. Barrier layer 30 can have any suitable thickness, for example, a thickness of about 0.1 to about 10 microns, more narrowly from about 0.25 to about 5 microns. The particular thickness of each layer is based on the type of procedure for which medical substrate 20 is employed, the amount of the active agent to be delivered, the rate at which the active agent is to be delivered, and the thickness of the other coating layers.

Thermal Treatment of a Coating

The method of the present invention includes exposing a polymer on a stent or a stent made from a polymer to a thermal treatment. Treatment includes heating or exposing the polymer to a temperature and maintaining the temperature for a duration of time. The duration of time can be less than a second, a second, minutes, or hours. In some embodiments, maintenance of temperature includes fluctuation in the temperature. The temperature can be increased or decreased during treatment so long as it remains within the range of the selected temperature.

In one embodiment, the thermal treatment is conducted on a composition applied to the stent, for example immediately after the composition has been applied to the stent while the composition on the stent is remains wet. The composition, for instance, can include a polymer (or polymers) and a solvent (or solvents), and optionally one or more active agents or drugs. The thermal treatment can be terminated when the coating becomes dry or extended for a period of time subsequent to the drying of the coating.

In another embodiment, the thermal treatment is conducted subsequent to the evaporation of the solvent, when the polymer is in a dry form. In other words, the thermal treatment is conducted when the polymeric coating is a dry coating. "Dry coating" is defined as a coating with less than about 10% residual fluid (e.g., solvent(s) or water) content (w/w). In one embodiment, the coating has less than about 2% residual fluid content (w/w), and more narrowly, less than about 1% residual fluid content (w/w). A coating can also have 0% residual fluid content (w/w).

The amount of residual fluids in the coating can be determined by a Karl Fisher, or ThermoGravimetric Analysis (TGA), study. For example, a coated stent can be placed in the TGA instrument, and the weight change can be measured at 100° C. as an indication of water content, or measured at a temperature equal to the boiling temperature of the solvent used in the coating as an indication of the solvent content.

The stent can undergo the thermal treatment process at any appropriate stage of manufacture, such as before being packaged, or concurrently with or subsequent to the stent being secured onto a stent delivery device such as a catheter. For instance, the stent coating can be exposed to the appropriate temperature as the stent is being crimped onto the delivery device, and then further coated with a polymeric drug coating material.

The heat source/emitter used to thermally treat the coating can be any apparatus that emits radiation capable of heating the polymeric coating. For example, the heat source can be a cauterizer tip, a RF source, or a microwave emitter. The heat source can also be a blower that includes a heating device so that the blower can direct a warm gas onto the implantable device. The gas can be inert (e.g., air, argon, nitrogen, etc.). For example, the heating device can be an electric heater incorporating heating coils or a system that includes a gas source and a computer controller to control the temperature of the gas directed at the stents.

Figure 2:
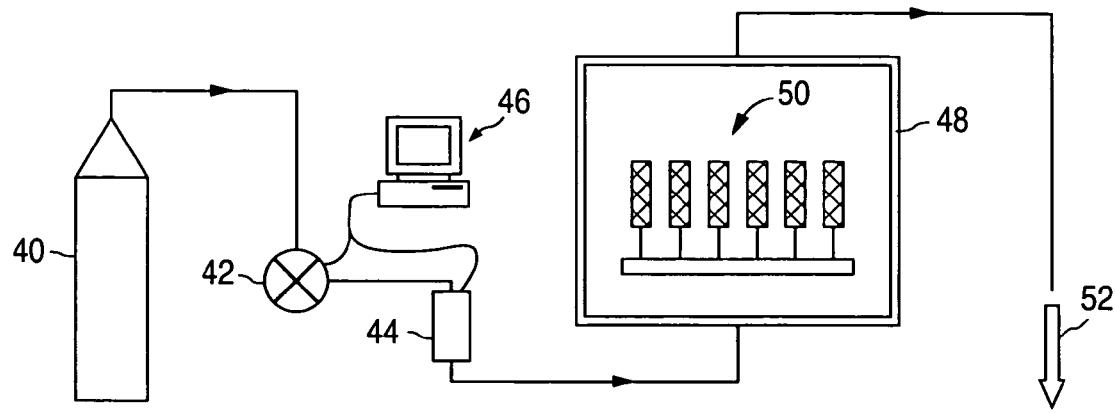
FIG. 2 is an illustration of a system for thermally treating stents.

Referring to FIG. 2, a gas system for the thermal treatment process can include a gas source 40, a flow controller 42 (e.g., a flow controller available from Eurotherm Control, Inc., Leesburg, Va.), an in-line heater 44 (e.g., an in-line heater available from Sylvania, Danvers, Mass.), a computer controller 46, an air tight chamber 48 for holding a plurality of stents 50 and an exhaust 52. Computer controller 46 can be in communication with flow controller 42 and in-line heater 44 to control the amount of air and temperature, respectively, which is delivered to chamber 48. Exhaust 52 can provide a route for unwanted components (e.g., oxygen) to travel after being removed from the stent coatings. In-line heater 44 can be used to precisely and gradually increase the temperature of the gas delivered by gas source 40 to the temperature used to conduct the thermal treatment.

In one embodiment, a polymeric coating on a stent or a polymeric stent body is exposed to a temperature for a duration of time sufficient to improve the mechanical properties of the coating or the stent body. In one embodiment, the temperature can be above ambient temperature. The temperature can also be below the melting temperature of the polymer. For example, a polymer in a primer layer can be exposed to the temperature to improve the mechanical properties of the primer layer. The thermal treatment can be beneficial because the treatment can cause the primer layer to act as a more effective adhesive tie layer between the stent substrate and subsequently applied layers of polymer. For example, as demonstrated by Example 30-34, the heat treatment can cause the primer layer to act as a better adhesive tie layer between a metallic surface of the stent and a drug reservoir layer. Without being bound by any particular theory, it is believed that the thermal treatment process of a primer layer can improve adhesion of a drug-delivery coating on a stent by (1) improving the film formation of the primer layer (e.g., causing the polymeric primer layer to flow into imperfections (i.e., microcracks) in the stent substrate); (2) removing residual stresses in the coating; and/or (3) if the polymer is a semicrystalline polymer, increasing the crystallinity of the polymer.

The thermal treatment can also be beneficial because the treatment can improve the adhesion between multiple layers of coating material. Without being bound by any particular theory, it is believed that the thermal treatment process will improve adhesion by increasing polymer chain entanglement between the polymers of the different layers.

In another embodiment, polymeric coatings having an active agent can be exposed to a temperature that is greater than ambient temperature and is sufficient to decrease the release rate of the active agent from the coating. The coatings illustrated in FIGS. 1B-H, for instance, can be exposed to the thermal treatment process to decrease the release rate of the active agent from the coatings. For example, without thermal treatment, an active agent (such as 40-O-(2-hydroxy)ethyl-rapamycin) can diffuse from the polymer matrix at a rate that could be too high for certain clinical conditions. By using the process of the present invention, however, the coating can be exposed to a sufficient temperature effective to decrease the release rate of 40-O-(2-hydroxy)ethyl-rapamycin, or analog or derivative thereof, by about 50% as compared to a control group, as demonstrated in Example 53 below.

Without being bound by any particular theory, it is believed that the thermal treatment process can decrease the release rate of the active agent from the polymeric drug coating by redistributing the microphase distribution of the active agent in the coating, thereby causing the active agent to cluster. In particular, the redistribution can decrease the surface area of the active agent clusters as the clusters are exposed to bodily fluids at the treatment site. Furthermore, the thermal treatment can decrease the release rate of the active agent by (1) decreasing the free volume in an amorphous polymer; (2) increasing the crosslinking of the polymer in the coating; and (3) repairing minute imperfections in the coating such as cracks formed during the initial coating process.

Furthermore, it is believed that an active agent has a greater diffusivity in the amorphous domain of a polymer as compared to the crystalline domain. Most polymeric materials used for drug delivery stent coatings have some crystallinity and the degree of polymer crystallinity directly affects an active agent's diffusivity due to changes in free volume and the increase in the volume fraction of the crystalline phase. Without being bound by any particular theory, it is believed that the diffusion rate of the active agent from the polymer can be decreased because heating the polymer increases the percent crystallinity of the polymer.

Additionally, using the thermal treatment process to treat a polymeric drug coating can increase the manufacturing consistency of drug delivery stents by reducing the variability of the release rate of active agents among stents. The thermal treatment process can also reduce the release rate drift over time. "Release rate drift" refers to the phenomenon in which the release rate of an active agent from a polymeric coating can change over time, for instance, while the stent is in storage. Release rate drift may occur because of changes in the morphology of a polymeric coating over a period of time, for example by exposure to degradation agents such as oxygen and moisture. As demonstrated by Example 95, by exposing a stent coating to a temperature greater than the glass transition temperature of the polymer in the coating, the standard deviation of the mean release rate of the active agent in a 24 hour period can be decreased so that the standard deviation is lower than the standard deviation of the mean release rate for a baseline group of stents (i.e., stents which have not been subjected to a thermal treatment process). It is believed that the thermal treatment process can increase manufacturing consistency by moving a polymeric stent coating closer to a thermodynamic equilibrium.

In one embodiment, the polymer in the coating is a thermoplastic polymer. In another embodiment, the polymer in the coating is an amorphous polymer (e.g., D,L-poly(lactic acid)). As understood by those of ordinary skill in the art, "amorphous polymers" refer to those polymers that are void of crystallinity. Amorphous polymers can be differentiated from semicrystalline or crystalline polymers by certain quantifiable characteristics. For example, as further described herein, amorphous polymers do not have a melting temperature ($T_m$) (while crystalline and semicrystalline polymers do have a $T_m$), and can have a sharp glass transition. It is believed that the heat treatment of an amorphous polymer in a coating can improve the polymeric film formation on the stent.

In another embodiment of the present invention, the polymer in the coating is a semicrystalline polymer (e.g., polyvinyl chloride or an ethylene vinyl alcohol copolymer). As understood by those of ordinary skill in the art, "semicrystalline polymers" refer to those polymers that have at least some crystallinity. Semicrystalline polymers can be differentiated from amorphous polymers by certain quantifiable characteristics. For example, as further described herein, semicrystalline polymers have a glass transition temperature ($T_g$) and a $T_m$.

In one embodiment, a polymeric coating including a semicrystalline polymer is exposed to the crystallization temperature ($T_c$) of the semicrystalline polymer or above the $T_c$. In one embodiment, the polymer should have a $T_c$ greater than ambient temperature. "Crystallization temperature" refers to the temperature at which a semicrystalline polymer has its highest percent crystallinity. Amorphous polymers do not exhibit a crystallization temperature. The crystallization temperature of ethylene vinyl alcohol copolymer (44 mole % ethylene), for instance, is about 415° K. Other examples of crystallization temperatures include 396° K. for poly(ethylene terephthalate) as measured by differential scanning calorimetry (as reported by Parravicini et al., J. Appl. Polym. Sci., 52(7), 875-85 (1994)); and 400° K. for poly(p-phenylene sulfide) as measured by differential scanning calorimetry (as reported by Ding et al. Macromolecules, 29(13), 4811-12 (1996)).

It is believed that the composition components (e.g., solvents) and process parameters that are often used to coat stents do not allow for maximum crystallinity in the polymer matrix. If a highly volatile solvent is included in the composition, for example, then the polymer does not have sufficient time to fully crystallize before the solvent has evaporated from the coating. As noted above, it is believed that the primer layer can act as a more effective adhesive tie layer if the percent crystallinity of a semicrystalline polymer is increased by the heat treatment. Also, the release rate of a drug from the polymeric matrix can be reduced by increasing the percent of crystallinity of the polymeric coating (e.g., the reservoir and/or barrier layers.) "Percent crystallinity" refers to the percentage of the polymer material that is in a crystalline form. It is thought that the methods of the present invention can increase the percent crystallinity of the polymer by about 5 to 30, more narrowly about 20 to 30 percent crystallinity.

Those of ordinary skill in the art understand that there are several methods for determining the percent crystallinity in polymers. These methods are, for example, described in L. H. Sperline, Introduction to Physical Polymer Science ($3^{rd}$ ed. 2001). The first involves the determination of the heat of fusion of the whole sample by calorimetric methods. The heat of fusion per mole of crystalline material can then be estimated independently by melting point depression experiments. The percent crystallinity is then given by heat of fusion of the whole sample divided by the heat of fusion per mole of crystalline material times 100. Representative example of this process and calculation are described in Sarasua et al., Crystallization and Melting Behavior of Polylactides, Macromolecules 31(12), 3895-3905 (1998); and Reeve et al., Polylactide Stereochemistry: Effect of Enzymatic Degradability, Macromolecules 27(3), 825-31 (1994) (citing Bloembergen et al., Studies of Composition and Crystallinity of Bacterial Poly(β-hydroxybutyrate-co-β-hydroxyvalerate, Macromolecules 19(11), 2865-70 (1986)).

A second method involves the determination of the density of the crystalline portion via X-ray analysis of the crystal structure, and determining the theoretical density of a 100% crystalline material. The density of the amorphous material can be determined from an extrapolation of the density from the melt to the temperature of interest. Then the percent crystallinity is given by:

$$\% \text{ Crystallinity} = \frac{\rho_{exptl} - \rho_{amorph}}{\rho_{100\% \, cryst} - \rho_{amorph}} \times 100$$

where $\rho_{exptl}$ represents the experimental density, and $\rho_{amorph}$ and $\rho_{100\% \, cryst}$ are the densities of the amorphous and crystalline portions, respectively.

A third method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This third method can be quantified by the crystallinity index, CI, where $$CI = \frac{A_c}{A_a + A_c}$$

and where $A_c$ and $A_a$ represent the area under the Bragg diffraction line and corresponding amorphous halo, respectively.

In some embodiments of the present invention, the thermal treatment process can be used to heat a polymeric coating on a stent to a temperature equal to or greater than a $T_g$ of a polymer included in the coating. As noted above, both amorphous and semicrystalline polymers exhibit glass transition temperatures. Additionally, if the polymer is a semicrystalline polymer, the polymeric coating can be exposed to a temperature equal to or greater than the $T_g$ and less than the $T_m$ of the polymer included in the coating. In another embodiment, the polymer is exposed to a temperature greater than the $T_m$ of the polymer included in the coating. Amorphous polymers do not exhibit a $T_m$. In one embodiment, the $T_g$ and $T_m$ of the polymer is greater than ambient temperature.

The polymer can include a crystalline component and an amorphous component. In one embodiment, the polymer is exposed to a temperature equal to or greater than the $T_g$ of one or both components. In another embodiment, the polymer is exposed to a temperature less than the $T_m$ of the crystalline component. In yet another embodiment, the polymer is exposed to a temperature greater than the $T_m$ of the crystalline component.

In yet another embodiment, the polymeric coating is exposed to the annealing temperature of the polymer. "Annealing temperature" refers to the temperature equal to $(T_g+T_m)/2$. The annealing temperature for ethylene vinyl alcohol copolymer, for instance, is about 383° K. The polymeric coating can also be exposed, in another embodiment, to a temperature equal to 0.9 times the $T_m$ of the polymer, with the $T_m$ expressed in Kelvin (e.g., about 394° K. for ethylene vinyl alcohol copolymer).

The $T_g$ is the temperature at which the amorphous domains of a polymer change from a brittle vitreous state to a plastic state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement.

Figure 4:
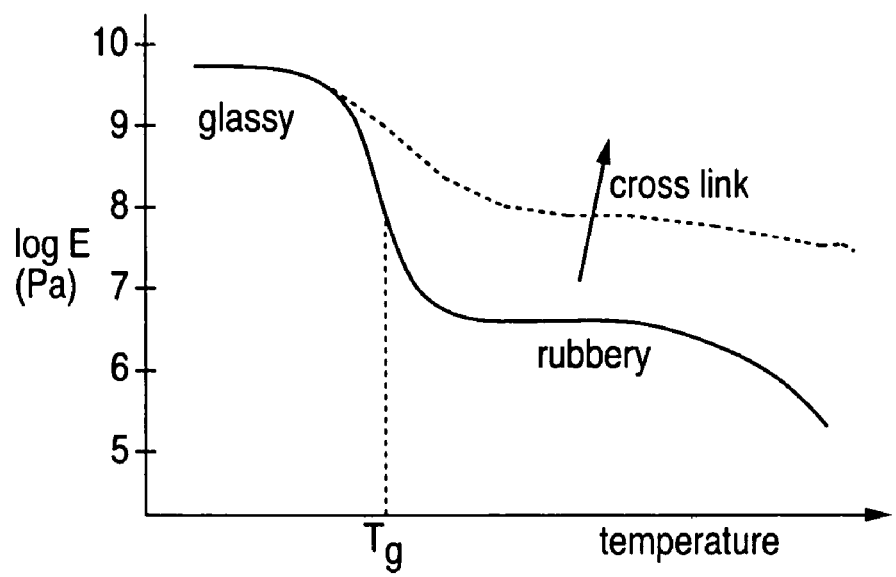
FIG. 4 is graph of the relationship of elasticity versus temperature for a polymer.

$T_g$ of a given polymer can be dependent on the heating rate and can be influenced by the thermal history of the polymer. Furthermore, the chemical structure of the polymer heavily influences the glass transition by affecting mobility. Generally, flexible main-chain components lower the $T_g$; bulky side-groups raise the $T_g$; increasing the length of flexible side-groups lowers the $T_g$; and increasing main-chain polarity increases the $T_g$. Additionally, the presence of crosslinking polymeric components can increase the observed $T_g$ for a given polymer. For instance, FIG. 4 illustrates the effect of temperature and crosslinking on the modulus of elasticity of a polymer, showing that forming cross-links in a polymer can increase the $T_g$ and shift the elastic response to a higher plateau—one that indicates that the polymer has become more glassy and brittle. Moreover, molecular weight can significantly influence $T_g$, especially at lower molecular weights where the excess of free volume associated with chain ends is significant.

The $T_m$ of a polymer, on the other hand, is the temperature at which the last trace of crystallinity in a polymer disappears as a sample is exposed to increasing heat. The $T_m$ of a polymer is also known as the fusion temperature ($T_f$). The $T_m$ is always greater than the $T_g$ for a given polymer.

Like the $T_g$, the $T_m$ of a given polymer is influenced by the structure of the polymer. The most influential inter- and intramolecular structural characteristics include structural regularity, bond flexibility, close-packing ability, and interchain attraction. In general, high melting points are associated with highly regular structures, rigid molecules, close-packing capability, strong interchain attraction, or two or more of these factors combined.

Figure 3:
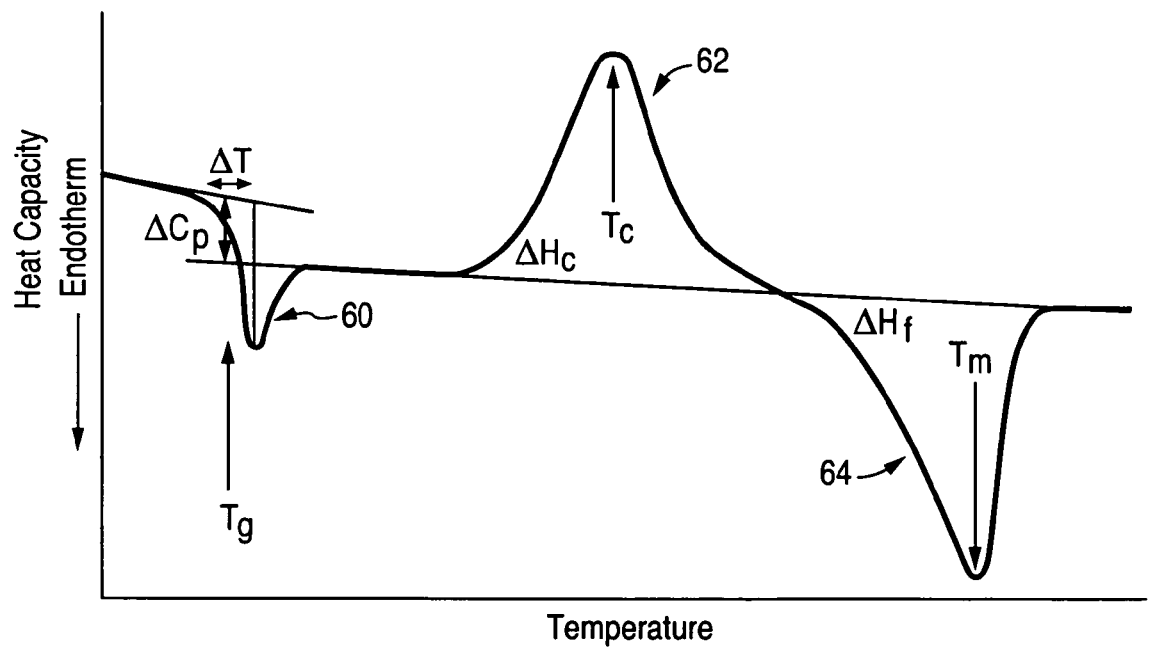
FIG. 3 is a graph of the relationship of heat capacity versus temperature for a polymer.

Referring to FIG. 3, if the coating polymer is a semicrystalline polymer, as the polymeric coating is exposed to an increasing temperature, the polymer exhibits three characteristic thermal transitions represented by first curve 60, second curve 62 and third curve 64. FIG. 3 illustrates the change in heat capacity (endothermic v. exothermic) of a semicrystalline polymer as the polymer is exposed to an increasing temperature, as measured by the differential scanning calorimetry (DSC) method. DSC uses the relationship between heat capacity and temperature as the basis for determining the thermal properties of polymers and is further described below.

By way of illustration, when a semicrystalline polymer is exposed to an increasing temperature, the crystallinity of the polymer begins to increase as the increasing temperature reaches the $T_g$. At and above the $T_g$, the increased molecular motion of the polymer allows the polymer chains to move around more to adopt a more thermodynamically stable relationship, and thereby increase the percent crystallinity of the polymer sample. In FIG. 3, the $T_g$ is shown as point $T_g$ of first curve 60, which is the temperature at which half of the increase in heat capacity ($\Delta C_p$) has occurred. The percent crystallinity then increases rapidly after point $T_g$ and is maximized at the $T_c$ of the polymer, which is indicated at the point $T_c$ (the apex of second curve 62). As the temperature continues to increase, the temperature approaches the $T_m$ of the polymer, and the percent crystallinity decreases until the temperature reaches the melting temperature of the polymer (at point $T_m$ of curve 64). As noted above, $T_m$ is the temperature where the last trace of crystallinity in the polymer disappears. The heat of crystallization, $\Delta H_c$, and the heat of fusion, $\Delta H_f$, can be calculated as the areas under curves 62 and 64. The heat of crystallization and heat of fusion must be equal, but with opposite signs.

The $T_g$ and/or the $T_m$ of the polymer that is to be exposed to the thermal treatment should be determined experimentally in order to determine which temperatures can be used to thermally treat the polymeric coating. As used herein, "test polymer" means the polymer that is measured to determine the $T_g$ and/or the $T_m$ of the polymer. "Coating polymer" means the polymer that is actually applied as a component of the stent coating, in other words, the one or more polymers applied as components of the primer layer, drug reservoir layer and barrier layer.

In order to accurately characterize the thermal properties of the coating polymer, one should consider the number of factors that can influence the $T_g$ and $T_m$ of a polymer. In particular, the factors include (1) the structure of the polymer (e.g., modification of side groups and dissimilar stereoregularity); (2) the molecular weight of the polymer; (3) the molecular-weight distribution ($M_w/M_n$) of the polymer; (4) the crystallinity of the polymer; (5) the thermal history of the polymer; (6) additives or fillers that are included in the polymer; (7) the pressure applied to the polymer as the polymer is heated; (8) residual fluids in the polymer; (9) the rate that the polymer is heated; and (10) the method used to apply the polymer to the substrate (e.g., a controlled deposition process as compared to a spray coating process).

One can account for the foregoing factors by using a test polymer that is substantially the same as the coating polymer, and is tested under substantially the same conditions as the conditions used to conduct the thermal treatment of the polymeric coating. The test polymer should have the same chemical structure as the coating polymer, and should have substantially the same molecular weight and molecular-weight distribution as the coating polymer. For example, if the polymer is a blend of copolymers or homopolymers, the test polymer should have substantially the same percentage of components as the coating polymer. At the same time, the test polymer should have substantially the same crystallinity as the coating polymer. Methods of determining cystallinity are discussed herein. Additionally, the composition used to form the test polymer should include the same compounds (e.g., additives such as therapeutic substances) and fluids (e.g., solvent(s) and water) that are mixed with the coating polymer. Moreover, the test polymer should have the same thermal history as the coating polymer. The test polymer should be prepared under the same conditions as the coating polymer, such as using the same solvent, temperature, humidity and mixing conditions. The heating rate used for measuring the transition temperature of the test polymer should be substantially similar to the heating rate used to conduct the thermal treatment of the polymeric coating. Finally, the method used to apply the test polymer to the substrate should be the same as the method used to apply the polymeric coating to the stent.

The $T_g$ and $T_m$ of the test polymer can be measured experimentally by testing a bulk sample of the polymer. As understood by one of ordinary skill in the art, a bulk sample of the polymer can be prepared by standard techniques, for example those that are outlined in the documentation accompanying the instruments used to measure the transition temperature of the polymer.

There are several methods that can be used to measure the $T_g$ and $T_m$ of a polymer. The $T_g$ and $T_m$ can be observed experimentally by measuring any one of several basic thermodynamic, physical, mechanical, or electrical properties as a function of temperature. Methods of measuring glass transition temperatures and melting temperatures are understood by one of ordinary skill in the art and are discussed by, for example, L. H. Sperling, Introduction to Physical Polymer Science, Wiley-Interscience, New York ($3^{rd}$ ed. 2001); and R. F. Boyer, in Encyclopedia of Polymer Science and Technology, Suppl. Vol. 2, N. M. Bikales, ed., Interscience, New York (1977).

Figure 5:
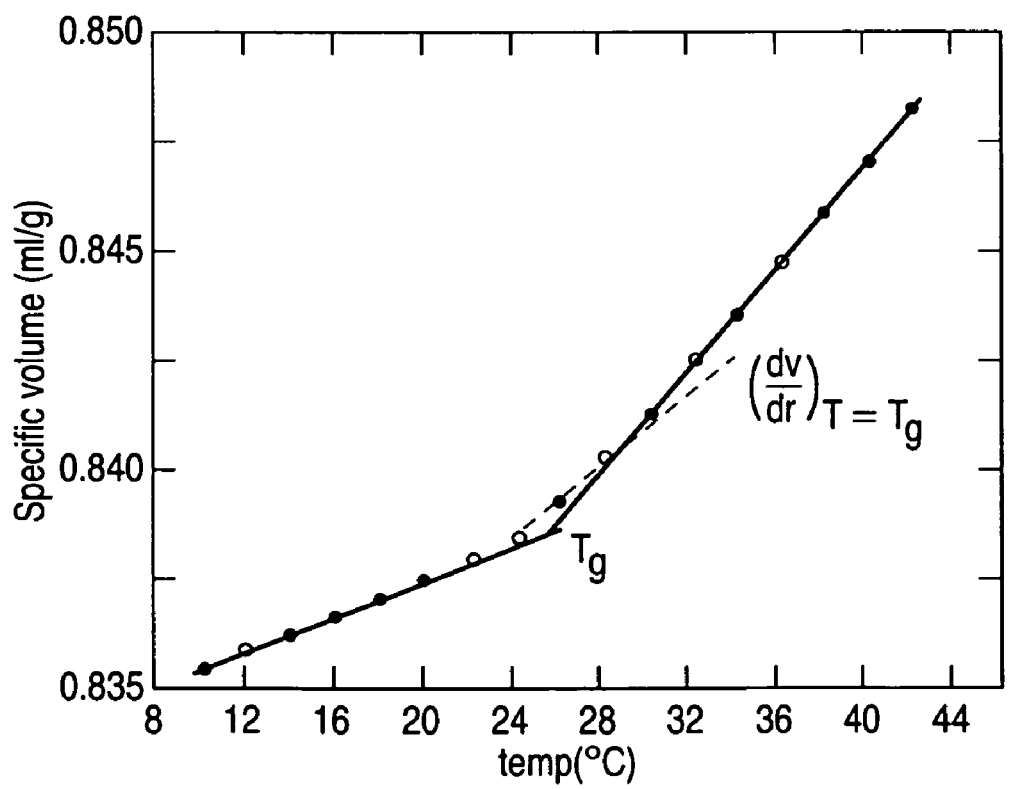
FIG. 5 is a graph of the relationship of specific volume versus temperature for a polymer.

The $T_g$ of a bulk sample can be observed by measuring the expansion of the polymer as the polymer is exposed to increasing temperature. This process is known as dilatometry. There are at least two ways of characterizing polymers via dilatometry. One way is to measure the linear expansivity of the polymer sample. Another method involves performing volume-temperature measurements, where the polymer is confined by a liquid and the change in volume is recorded as the temperature is raised. The usual confining liquid is mercury, since it does not swell organic polymers and has no transition of its own through most of the temperature range of interest. The results may be plotted as specific volume versus temperature as shown in FIG. 5, which illustrates a representative example of a dilatometric study of branched poly(vinyl acetate). Since the elbow in volume-temperature studies is not sharp (measurements of $T_g$ using dilatometric studies show a dispersion of about 20-30° C.), the two straight lines below and above the transition are extrapolated until they meet. The extrapolated meeting point is taken as the $T_g$. A representative example of an apparatus that can be used to measure a $T_g$ via dilatometric studies is the Dilatometer DIL 402 PC (available from Netzsch, Inc., Exton, Pa.).

Thermal methods can also be used to measure the $T_g$ of a bulk sample. Two closely related methods are differential thermal analysis (DTA), and differential scanning calorimetry (DSC). Both methods yield peaks relating to endothermic and exothermic transitions and show changes in heat capacity. A representative example of a DTA apparatus is the Rheometrics STA 1500 which provides simultaneous thermal analysis via DTA and DSC.

In addition to the information that can be produced by a DTA, the DSC method also yields quantitative information relating to the enthalpic changes in the polymer (the heat of fusion of the temperature, $\Delta H_f$). The DSC method uses a servo system to supply energy at a varying rate to the sample and the reference, so that the temperatures of the two stay equal. The DSC output plots energy supplied against average temperature. By this method, the areas under the peaks can be directly related to the enthalpic changes quantitatively.

Referring to FIG. 3, the $T_g$ can be taken as the temperature at which one-half of the increase in the heat capacity, $\Delta C_p$, has occurred. The increase in $\Delta C_p$ is associated with the increased molecular motion of the polymer.

A method of separating a transient phenomenon such as a hysteresis peak from the reproducible result of the change in heat capacity is obtained via the use of modulated DSC. Here, a sine wave is imposed on the temperature ramp. A real-time computer analysis allows a plot of not only the whole data but also its transient and reproducible components. Representative examples of modulated DSC apparatuses are those in the Q Series™ DSC product line from TA Instruments, New Castle, Del.

Another representative example of an apparatus that uses DSC as the base technology for measuring the $T_g$ is a micro thermal analyzer, such as the μTA™ 2990 product from TA Instruments. A micro thermal analyzer can have an atomic force microscope (AFM) that is used in conjunction with a thermal analyzer. The instrument can be used to analyze individual sample domains identified from the AFM images. In a micro thermal analyzer such as the μTA™ 2990, the AFM measurement head can contain an ultra-miniature probe that functions as a programmable heat source and temperature sensor. A micro thermal analyzer, therefore, can provide information similar to that from traditional thermal analysis, but on a microscopic scale. For example, the μTA™ 2990 can provide images of a sample in terms of its topography, relative thermal conductivity and relative thermal diffusivity. The μTA™ 2990 can also provide spatial resolution of about 1 μm with a thermal probe and atomic resolution with regular AFM probes. Other advantages of the μTA™ 2990 is that it can heat the polymer sample from ambient to about 500° C. at heating rates up to 1500° C./minute which allows for rapid thermal characterization (e.g., in less than 60 seconds), and it can hold the sample isothermically over a broad range of temperatures (e.g., −70 to 300° C.), which allows for thermal characterization over a broad temperature range.

Since the notion of the glass-rubber transition stems from a softening behavior, mechanical methods can provide very direct determination of the $T_g$ for a bulk sample. Two fundamental types of measurement prevail: the static or quasi-static methods, and the dynamic methods. For amorphous polymers and many types of semicrystalline polymers in which the crystallinity does not approach 100%, stress relaxation, Gehman, and/or Glash-Berg instrumentation provide, through static measurement methods, rapid and inexpensive scans of the temperature behavior of new polymers before going on to more complex methods. Additionally, there are instruments that can be employed to measure dynamic mechanical spectroscopy (DMS) or dynamic mechanical analysis (DMA) behavior. A representative example of an apparatus for a DMA method is the DMA 242, available from Netzsch, Inc., Exton, Pa.

Another method for studying the mechanical spectra of all types of polymers, especially those that are not self-supporting, is torsional braid analysis (TBA). In this case the polymer is dipped onto a glass braid, which supports the sample. The braid is set into a torsional motion. The sinusoidal decay of the twisting action is recorded as a function of time as the temperature is changed. Because the braid acts as a support medium, the absolute magnitudes of the transitions are not obtained; only their temperatures and relative intensities are recorded.

The $T_g$ of a bulk sample of a polymer can also be observed by utilizing electromagnetic methods. Representative examples of electromagnetic methods for the characterization of transitions in polymers are dielectric loss (e.g., using the DEA 2970 dielectric analyzer, available from TA Instruments, New Castle, Del.) and broad-line nuclear magnetic resonance (NMR).

If the thickness of the coating polymer is ultra thin (i.e., less than 1 micron), it may be useful to utilize specialized measuring techniques, at least to compare the results with the values determined by measuring a bulk polymer sample to ensure that the bulk values are not affected by the thickness of the polymer layer. Specialized techniques may be useful because it has recently been observed that the $T_g$ of a polymer can be influenced by the thickness of the polymer layer. Researchers, for example, have observed that polystyrene films on hydrogen-passivated Si had glass transition temperatures that were lower than the bulk value if the thickness of the films was less than 0.04 microns. See Forest et al., Effect of Free Surfaces on the $T_g$ of Thin Polymer Films, Physical Review Letters 77(10), 2002-05 (September 1996).

Brillouin light scattering (BLS) can be used to measure the $T_g$ of a polymer in an ultra thin film. The ultra thin films can be prepared by spin casting the polymer onto a substrate (e.g., the same substrate used to support the coating polymer on the stent). A spinning apparatus is available, for example, from Headway Research, Inc., Garland, Tex. BLS can also be used to find the $T_g$ of a polymer in a bulk sample. In BLS studies of bulk polymers, one measures the velocity $v_L$ of the bulk longitudinal phonon, where $v_L=(C_{11}/\rho)^{1/2}$, $C_{11}$ is the longitudinal elastic constant, and $\rho$ is the density. Since $C_{11}$ is a strong function of $\rho$, as the sample temperature is changed, the temperature dependence of $v_L$ exhibits an abrupt change in slope at the temperature at which the thermal expansivity is discontinuous, i.e., the $T_g$. For thin films, BLS probes the elastic properties through observation of film-guided acoustic phonons. The guided acoustic modes are referred to as Lamb modes for freely standing films. For further discussion of the application of BLS for measuring $T_g$, see Forest et al., Effect of Free Surfaces on the Glass Transition Temperature of Thin Polymer Films, Physical Review Letters 77(10), 2002-05 (September 1996); and Forest et al., Mater. Res. Soc. Symp. Proc. 407, 131 (1996).

The $T_g$ of an ultra thin polymer film can also be determined by using three complementary techniques: local thermal analysis, ellipsometry and X-ray reflectivity. See, e.g., Fryer et al., Dependence of the Glass Transition Temperature of Polymer Films on Interfacial Energy and Thickness, Macromolecules 34, 5627-34 (2001). Using ellipsometry (e.g., with a Rudolph AUTO EL™ nulling ellipsometer) and X-ray reflectivity (e.g., with a SCINTAG XDS 2000™), the $T_g$ is determined by measuring changes in the thermal expansion of the film. Using local thermal analysis, on the other hand, the $T_g$ is determined by measuring changes in the heat capacity and thermal conductivity of the film and the area of contact between a probe and the polymer surface.

Table 1 lists the $T_g$ for some of the polymers used in the embodiments of the present invention. The cited temperature is the temperature as reported in the noted reference and is provided by way of illustration only and is not meant to be limiting.

TABLE 1

| POLYMER | $T_g$ (°K) | METHOD USED TO CALCULATE $T_g$ | REFERENCE |
|---|---|---|---|
| Ethylene vinyl alcohol copolymer | 330 | DMA | Tokoh et al., Chem. Express, 2(9), 575-78 (1987) |
| Poly(n-butyl methacrylate) | 293 | Dilatometry | Rogers et al., J. Phys. Chem., 61, 985-90 (1957) |
| Poly(ethylene-co-(vinyl acetate) | 263 | DSC and DMA | Scott et al., J. Polym. Sci., Part A, Polym. Chem., 32(3), 539-55 (1994) |
| Poly(ethylene terephthalate) | 343.69 | DSC | Sun et al., J. Polym. Sci., Part A, Polym. Chem., 34(9), 1783-92 (1996) |
| Poly-(vinylidene fluoride) | 243 | Dielectric relaxation | Barid et al., J. Mater. Sci., 10(7), 1248-51 (1975) |
| Poly(p-phenylene sulfide) | 361 | DSC | Ding et al., Macromolecules, 29(13), 4811-12 (1996) |
| Poly(6-aminocaproic acid) | 325 | DSC | Gee et al., Polymer, 11, 192-97 (1970) |
| Poly(methyl methacrylate) | 367 | DSC | Fernandez-Martin et al., J. Polym. Sci., Polym. Phys. Ed., 19(9), 1353-63 (1981) |
| Poly(vinyl alcohol) | 363 | Dilatometry | Fujii et al., J. Polym. Sci., Part A, 2, 2327-47 (1964) |
| Poly(epsilon-caprolactone) | 208 | DSC | Loefgren et al., Macromolecules, 27(20), 5556-62 (1994) |

As noted above, "polymer" as used herein is inclusive of homopolymers, copolymers, terpolymers etc., including random, alternating, block, cross-linked, blends and graft variations thereof. By using the methods of measurement described above, one may observe more than one $T_g$ for some of these types of polymers. For example, some polymer blends that exhibit two phase systems can have more than one $T_g$. If the polymer of the coating is a combination or blend of polymers, then the selected temperature is determined as previously described. For example, if the coating is a blend of ethylene vinyl alcohol copolymer and poly(vinyl alcohol) the $T_g$ of the blend can be calculated by using a DSC method. In some embodiments, the lower $T_g$ is the designated $T_g$. In another embodiment, the higher $T_g$ is the designated $T_g$.

Additionally, some semicrystalline polymers can have two glass transitions, especially when they have a higher percent crystallinity. See Edith A. Turi, Thermal Characterization of Polymeric Materials, Academic Press, Orlando, Fla. (1981). Bulk-crystallized polyethylene and polypropylene, for example, can have two glass transition temperatures at a relatively high percent crystallinity. The lower of the two transitions is represented as $T_g(L)$, which can be the same as the conventional $T_g$ at zero crystallinity. The higher transition is designated as $T_g(U)$ and becomes more detectable as the crystallinity increases. The difference, $\Delta T_g = T_g(U) - T_g(L)$, tends to approach zero as the fractional crystallinity $\chi$ approaches zero.

It has also been reported that block and graft copolymers can have two separate glass transition temperatures. For some of these polymers, each $T_g$ can be close to the $T_g$ of the parent homopolymer. The following Table 2 lists the glass transition temperatures for representative examples of block and graft copolymers that can be used in the present invention. As illustrated by Table 2, most of these block and graft copolymers exhibit two glass transition temperatures. The cited temperatures were reported in Black and Worsfold, J. Appl. Polym. Sci., 18, 2307 (1974). The researches from this reference used a thermal expansion technique to measure the temperatures, and are provided by way of illustration only.

TABLE 2

| $M_1$ | $M_2$ | % $M_1$ | Total MW | Lower $T_g$ (°K) | Upper $T_g$ (°K) |
|---|---|---|---|---|---|
| α-Methylstyrene | Vinyl acetate | 18 | 103,000 | 308 | 455 |
| α-Methylstyrene | Vinyl chloride | 67 | 39,000 | 265 | 455 |
| α-Methylstyrene | Styrene | 45 | 61,000 | 400 | — |
| Styrene | Methyl methacrylate | 40 | 70,000 | — | 371 |
| Styrene | Butyl acrylate | 46 | 104,000 | 218 | 372 |
| Styrene | Ethylene oxide | 50 | 40,000 | 201 | 373 |
| Styrene | Isoprene | 50 | 1,000,000 | 198 | 374 |
| Styrene | Isobutylene | 40 | 141,000 | 204 | 375 |
| Methyl Methacrylate | Ethyl acrylate | 56 | 162,000 | 250 | 388 |
| Methyl Methacrylate | Vinyl acetate | 50 | 96,000 | 311 | 371 |
| Methyl Methacrylate | Ethyl methacrylate | 50 | 104,000 | 342 | 379 |

In one embodiment of the present invention, if the polymer exhibits more than one $T_g$, the polymer is exposed to a temperature equal to or greater than the lowest observed $T_g$. It is believed that by exposing a polymer to a temperature equal to or greater than the lowest $T_g$, the coating characteristics will be improved because at least some of the amorphous domains will be modified during the process. In another embodiment, if the polymer in the coating exhibits more than one $T_g$, the polymer is exposed to a temperature equal to or greater than the highest observed $T_g$. By exposing the polymer to the highest $T_g$, it is believed that one can maximize the improvement in coating characteristics, for example, maximizing polymer adhesion and/or cohesion, or maximizing the drug release rate reduction.

As noted above, in one embodiment, the polymer in the coating can be exposed to a temperature equal to or greater than the $T_g$ and less than the $T_m$ of the polymer. There are several types of methods that can be used to measure the $T_m$ of a polymer. For example, the $T_m$ can be observed by measuring visual, physical, and thermal properties as a function of temperature.

$T_m$ can be measured by visual observation by using microscopic techniques. For instance, the disappearance of crystallinity in a semicrystalline or crystalline polymer can be observed with a microscope, with the sample housed between crossed nicols (i.e., an optical material that functions as a prism, separating light rays that pass through it into two portions, one of which is reflected away and the other transmitted). As a polymer sample is heated, the sharp X-ray pattern characteristic of crystalline material gives way to amorphous halos at the $T_m$.

Another way of observing the $T_m$ is to observe the changes in specific volume with temperature. Since melting constitutes a first-order phase change, a discontinuity in the volume is expected. The $T_m$ should give a discontinuity in the volume, with a concomitant sharp melting point. Because of the very small size of the crystallites in bulk crystallized polymers, however, most polymers melt over a range of several degrees. The $T_m$ is the temperature at which the last trace of crystallinity disappears. This is the temperature at which the largest and/or most "perfect" crystals are melting.

Alternatively, the $T_m$ can be determined by using thermomechanical analysis (TMA) that uses a thermal probe (e.g., available from Perkin Elmer, Norwalk, Conn.). The $T_m$ can also be determined with a thermal-based method. For example, a differential scanning calorimetry (DSC) study can be used to determine the $T_m$. The same process for DSC as described above for the determination of $T_g$ can be used to determine the $T_m$. Referring to FIG. 3, the $T_m$ of the representative polymer is the peak of curve 64.

Table 3 lists the $T_m$ for some of the polymers used in the embodiments of the present invention. The cited temperature is the temperature as reported in the noted reference and is provided by way of illustration only and is not meant to be limiting.

TABLE 3

| POLYMER | $T_m$ (°K) | METHOD USED TO CALCULATE $T_m$ | REFERENCE |
| --- | --- | --- | --- |
| Ethylene vinyl alcohol copolymer | 437.3 | DMA | Tokoh et al., Chem. Express, 2(9), 575-78 (1987) |
| Poly(ethylene terephthalate) | 526.38 | DSC | Sun et al., J. Polym. Sci., Part A, Polym. Chem., 34(9), 1783-92 (1996) |
| Poly(vinylidene fluoride) | 444 | Dielectric relaxation | Barid et al., J. Mater. Sci., 10(7), 1248-51 (1975) |
| Poly(p-phenylene sulfide) | 560 | DSC | Ding et al., Macromolecules, 29(13), 4811-12 (1996) |
| Poly(6-aminocaproic acid) | 498 | DSC | Gee et al., Polymer, 11, 192-97 (1970) |
| Poly(vinyl alcohol) | 513 | TMA | Fujii et al., J. Polym. Sci., Part A, 2, 2327-47 (1964) |
| Poly(epsilon-caprolactone) | 330.5 | DSC | Loefgren et al., Macromolecules, 27(20), 5556-62 (1994) |

One can observe more than one $T_m$ while using the standard techniques to measure $T_m$ as described herein. For example, while using a DSC method of measuring $T_m$, a double melting peak can be observed. It has been suggested that multiple observed melting points can be due to the presence of two or more distinct crystal or morphological structures in the initial sample. It has also been suggested that this phenomenon can be the results of annealing occurring during the measurement process (e.g., during a DSC process) whereby crystals of low perfection melt have time to recrystallize a few degrees above and to remelt. See, e.g., Sarasua et al., Crystallization and Melting Behavior of Polylactides, Macromolecules 31(12), 3895-3905 (1998). To the extent that more than one $T_m$ is observed, the embodiments using $T_m$ herein use the highest observed $T_m$.

In the embodiments of the present invention, the thermal treatment process can be used to improve the mechanical properties of polymeric coatings having various coating structures, for instance, those structures illustrated in FIGS. 1A-1H. In the embodiments of the present invention, the thermal treatment process can also be used to reduce the release rate of an active agent from polymeric coatings having various coating structures. Referring to FIGS. 1B-1H, for instance, reservoir layer 26 can be exposed to a temperature sufficient to reduce the release rate of active agent 28 from the coating. In some embodiments, barrier layer 30 can be treated in lieu of or in addition to the reservoir layer 26.

Referring to FIG. 1A, primer layer 24 can be exposed to the thermal treatment process before a reservoir layer is applied to medical substrate 20 to improve the mechanical properties of the polymeric coating. By performing the thermal treatment process before application of the active agent containing reservoir coating, one can avoid exposing heat sensitive active agents to temperatures that can degrade or otherwise adversely affect the active agent. In yet another embodiment, the thermal treatment process is used to treat a coating having multiple layers wherein at least one of the layers is a primer layer. Referring to FIG. 1C, for instance, the coating including primer layer 24 and reservoir layer 26 can be heat treated.

In one embodiment, the polymer in primer layer 24 is exposed to a temperature equal to or greater than the $T_g$ of the polymer. In another embodiment, the polymer in primer layer 24 is exposed to a heat treatment at a temperature range equal to or greater than about the $T_g$ and optionally less than about the $T_m$ of the polymer. The device should be exposed to the heat treatment for any suitable duration of time that would allow for the formation of the primer coating on the surface of the device.

In one embodiment, primer layer 24 includes a thermoplastic polymer, such as ethylene vinyl alcohol copolymer, polycaprolactone, poly(lactide-co-glycolide), or poly(hydroxybutyrate). Table 4 lists the $T_g$ and $T_m$ for some of the polymers that can be used for primer layer 24. The cited exemplary temperature and time for exposure are provided by way of illustration and are not meant to be limiting.

TABLE 4

| Polymer | $T_g$ (° K) | $T_m$ (° K) | Exemplary Temperature (° K) | Exemplary Duration of Time For Heating |
|---|---|---|---|---|
| ethylene vinyl alcohol copolymer | 330 | 437.3 | 413 | 4 hours |
| polycaprolactone | 208 | 330.5 | 323 | 2 hours |
| ethylene vinyl acetate (e.g., 33% vinyl acetate content) | 309 | 336 | 318 | 2 hours |
| Polyvinyl alcohol | 363 | 513 | 438 | 2 hours |

In other embodiments, the polymer in primer layer 24 is exposed to (1) the $T_c$ of the polymer; (2) the annealing temperature of the polymer; (3) a temperature equal to 0.9 times the $T_m$ of the polymer, or (4) a temperature equal to or greater than the $T_m$ of the polymer.

In another embodiment, the thermal treatment process is used to treat a coating having reservoir layer 26. For example, referring to FIGS. 1B-1E, 1G and 1H, the polymer in reservoir layer 26 is exposed to a temperature equal to or greater than the $T_g$ of the polymer in reservoir layer 26. The polymer in reservoir layer 26 can also be exposed to a temperature equal to or greater than the $T_g$ and, optionally, less than the $T_m$ of the polymer. Also, the polymer can be exposed to (1) the $T_c$ of the polymer; (2) the annealing temperature of the polymer; (3) a temperature equal to 0.9 times the $T_m$ of the polymer; or (4) a temperature equal to or greater than the $T_m$ of the polymer. If reservoir layer 26 is covering a primer layer 24, the process can also be aimed at exposing the polymer(s) of primer layer 24 to a temperature equal to or greater than the $T_g$, equal to the $T_c$, the annealing temperature, a temperature equal to 0.9 times the $T_m$ or equal to or greater than the $T_m$ of the polymer(s). If, however, the $T_g$ of the primer layer is excessively high or higher than the $T_m$ of reservoir layer 26, such high temperatures may adversely affect the active agents.

The thermal treatment process can also be directed to a polymeric coating having a polymeric reservoir layer 26 covered at least in part by barrier layer 30 as illustrated by FIGS. 1E-1H. Referring to FIG. 1E, for instance, reservoir layer 26 can be deposited on primer layer 24 and covered by barrier layer 30. The polymer in barrier layer 30 can be exposed to a temperature equal to or greater than the $T_g$ of the polymer in barrier layer 30. A polymer included in barrier layer 30 can also be exposed to a temperature equal to or greater than the $T_g$ and, optionally, less than the $T_m$ of the polymer. Also, the polymer can be exposed to (1) the $T_c$ of the polymer; (2) the annealing temperature of the polymer or (3) a temperature equal to 0.9 times the $T_m$ of the polymer. If barrier layer 30 is covering a reservoir layer 26, reservoir layer 26 can also be heated to a temperature equal to or greater than the $T_g$ of a polymer in reservoir layer 26, equal to the $T_c$ of a polymer in reservoir layer 26, the annealing temperature of a polymer in reservoir layer 26, equal to 0.9 times the $T_m$ of the polymer, or equal to or greater than the $T_m$ of the polymer.

If the polymeric coating includes multiple layers of coating, the thermal treatment process can be conducted so that polymers in the different layers are heat treated simultaneously. By way of example, referring to FIG. 1G, the polymers in reservoir layer 26 and barrier layer 30, respectively, can be simultaneously exposed to a temperature equal to or greater than the $T_g$ of the polymers in the two layers. The polymers in reservoir layer 26 and barrier layer 30 can also be simultaneously exposed to (1) a temperature equal to or greater than the $T_g$ and less than the $T_m$ of the polymers; (2) the $T_c$ of the polymers; (3) the annealing temperature of the polymers; (4) a temperature equal to 0.9 times the $T_m$ of the polymers or (5) a temperature equal to or greater than the $T_m$ of the polymers. The polymers in reservoir layer 26 and barrier layer 30 can be simultaneously exposed to the appropriate temperature if, for instance, the polymer in reservoir layer 26 has the same or substantially the same thermal properties as the polymer in barrier layer 30. For example, the polymer in reservoir layer 26 can have about the same $T_c$ or $T_g$ as the polymer in barrier layer 30. The polymers in reservoir layer 26 and barrier layer 30 can also be simultaneously exposed to the appropriate temperature if the temperature used to conduct the thermal treatment is sufficiently high to surpass the selected temperature (e.g., annealing temperature, $T_c$, etc.) for each polymer.

The thermal treatment process can also be conducted to selectively treat the various polymeric layers. For example, one can selectively treat the polymeric layers by constructing a coating that has layers with polymers having different thermal properties. The coating illustrated by FIG. 1C, for instance, can be constructed so that the polymer in primer layer 24 has different thermal properties than the polymer in reservoir layer 26. In one embodiment, if the polymer in primer layer 24 has a $T_g$ that is higher than the $T_g$ of the polymer in reservoir layer 26, the polymeric coating is exposed to a temperature greater than the $T_g$ of the polymer in reservoir layer 26, but less than the $T_g$ of the polymer in primer layer 24. This process can also be used if the annealing temperature or $T_c$ of the polymer in primer layer 24 is greater than the annealing temperature or $T_c$ of the polymer in reservoir layer 26. In another embodiment, if the polymer in primer layer 24 has a $T_g$ that is lower than the $T_g$ of the polymer in reservoir layer 26, the polymeric coating is exposed to a temperature greater than the $T_g$ of the polymer in primer layer 24, but less than the $T_g$ of the polymer in reservoir layer 26. This process can also be used if the annealing temperature or $T_c$ of the polymer in primer layer 24 is lower than the annealing temperature or $T_c$ of the polymer in reservoir layer 26.

In another example, the coating illustrated by FIG. 1E can be constructed so that the polymer in reservoir layer 26 has different thermal properties than the polymer in barrier layer 30. In one embodiment, if the polymer in reservoir layer 26 has a $T_g$ that is higher than the $T_g$ of the polymer in barrier layer 30, the polymeric coating is exposed to a temperature greater than the $T_g$ of the polymer in barrier layer 30, but less than the $T_g$ of the polymer in reservoir layer 26. This process can also be used if the annealing temperature or $T_c$ of the polymer in reservoir layer 26 is greater than the annealing temperature or $T_c$ of the polymer in barrier layer 30. In another embodiment, if the polymer in reservoir layer 26 has a $T_g$ that is lower than the $T_g$ of the polymer in barrier layer 30, the polymeric coating is exposed to a temperature greater than the $T_g$ of the polymer in reservoir layer 26, but less than the $T_g$ of the polymer in barrier layer 30. This process can also be used if the annealing temperature or $T_c$ of the polymer in reservoir layer 26 is lower than the annealing temperature or $T_c$ of the polymer in barrier layer 30.

The heat source can be directed to only certain portions of the stent or only for certain durations so that the diffusion rates of the active agent from the polymer differs in various portions of the coating. Referring to FIG. 1H, for example, the polymeric material in barrier layer 30B can be exposed to a thermal treatment, whereas the polymeric material in barrier layer 30A is not. As a result, the release rate of the active agent from the polymeric material in barrier 30B can be lower than the release rate of the active agent from the polymeric material in barrier 30A. The release rate difference can result because, for example, the polymer of barrier layer 30B will have a higher percent crystallinity than the polymeric material in barrier layer 30A.

In another example, the stent can have two or more segments along the longitudinal axis of the stent, such as a first segment, a second segment and a third segment. The radiation could be directed substantially only at the first segment and the third segment, for instance, by using a cauterizer tip. Alternatively, the radiation could be set higher for the first and third segments, or the radiation could be directed at the first and third segments for a longer duration than the second segment. As a result, the polymer along the first segment and the third segment would have a greater percent crystallinity than the polymer along the second segment. Therefore, the diffusion rates of the active agent from the polymer matrix along the first segment and the third segment would be less than the diffusion rate along the second segment. In one embodiment, the first and third segments can be on the opposing end portions of the stent, the second segment being the middle region of the stent.

If the polymer in the coating is semicrystalline, the time that the coating is exposed to radiation can be limited so that the percent crystallinity is not maximized throughout the entire thickness of the coating. In other words, the shallower regions of the coating will have a higher percent crystallinity than the deeper regions. The degree of crystallinity decreases as a function of the depth of the coating. In a particular example, if the coating is defined as having four regions, with the fourth region as the deepest, by controlling the thermal treatment, the first or shallowest region would have a higher percent crystallinity, followed by the second, third and lastly fourth region, which would have the lowest degree of crystallinity.

The selected duration of the thermal treatment of the polymeric coating can depend on the selected exposure temperature, and the thermal characteristics of the polymer in the coating, among other environmental factors such as the humidity. The duration of the thermal treatment, for instance, can be from about 30 seconds to about 48 hours. By way of example, in a thermal treatment of a coating having ethylene vinyl alcohol copolymer and actinomycin D, the polymer can be exposed to a temperature of about 473° K. for about 2 minutes, or about 353° K. for about 2 hours.

The exposure temperature should not adversely affect the characteristics of the polymer or the active agent present in the coating. In order to prevent possible degradation of the active agent or the polymer in the coating, additives can be mixed with the polymer before or during the coating process to shift the thermal profile of the polymer (i.e., decrease the $T_g$ and $T_m$ of the polymer). For example, a plasticizer, which is usually a low molecular weight nonvolatile molecule, can be dissolved with the polymer before the application process. The plasticizer can be an active agent. A representative example of an additive is dioctyl phthalate. The selected duration of the thermal treatment of the reservoir layer and/or barrier layer can depend on the selected exposure temperature, the thermal characteristics of the polymer in the coating, the thermal stability of the active agent and the desired release rate, among other factors.

Sterilization of the Stent

After the stent has been coated according to the various embodiments of the present invention, the stent can be sterilized by various methods. In an embodiment of the present invention, the particular procedure used to sterilize the coating can also be modified to conduct the thermal treating process. For example, an electron beam or a gas sterilization procedure can be used to conduct the thermal treating process and to sterilize the coating that has been formed on the stent. Representative examples of gas sterilization procedures include those using ethylene oxide, steam/autoclaving, hydrogen peroxide and peracetic acid. The sterilization processes can be modified so that the temperature produced during the process is sufficient to have the desired effect on the coating, for example, to decrease the release rate of the active agent from the polymeric coating, but not significantly degrade the active agent. For example, for the electron beam sterilization procedure, the exposure temperature is at least a function of dose, dose rate, heat capacity of the coating material and the degree of insulation of the product. These variables can be adjusted so that the coating is exposed to the appropriate temperature.

Forming a Primer Layer

As noted above, the presence of an active agent in a polymeric matrix can interfere with the ability of the matrix to adhere effectively to the surface of the device. Increasing the quantity of the active agent reduces the effectiveness of the adhesion. High drug loadings in the coating can hinder the retention of the coating on the surface of the device. A primer layer can serve as a functionally useful intermediary layer between the surface of the device and an active agent-containing or reservoir coating, or between multiple layers of reservoir coatings. The primer layer provides an adhesive tie between the reservoir coating and the device—which, in effect, would also allow for the quantity of the active agent in the reservoir coating to be increased without compromising the ability of the reservoir coating to be effectively contained on the device during delivery and, if applicable, expansion of the device.

The primer layer can be formed by applying a polymer or prepolymer to the stent by conventional methods. For example, a polymer or a prepolymer can be applied by applying the polymer directly onto the stent substrate such as by powder coating or by vapor deposition. In one embodiment, an unsaturated prepolymer (e.g., an unsaturated polyester or acrylates) is applied to the device, and then heat treated to cause the prepolymer to crosslink.

The polymer or prepolymer can also be applied by depositing a polymer composition onto the stent. The polymer composition can be prepared by combining a predetermined amount of a polymer or a prepolymer and a predetermined amount of a solvent or a combination of solvents. "Solvent" is defined as a liquid substance or composition that is compatible with the components of the composition and is capable of dissolving the component(s) at the concentration desired in the composition. The mixture can be prepared in ambient pressure and under anhydrous atmosphere. If necessary, a free radical or UV initiator can be added to the composition for initiating the curing or cross-linking of a prepolymer. Heating and stirring and/or mixing can be employed to effect dissolution of the polymer into the solvent. The composition can then be applied by convention methods such as by spraying the stent substrate with the composition or dipping the substrate into the composition.

The polymers used for the primer material should have a high capacity of adherence to the surface of an implantable device, such as a metallic surface of a stent, or a high capacity of adherence to a polymeric surface such as the surface of a stent made of polymer, or a previously applied layer of polymeric material.

Stainless steel such as 316L is a commonly used material for the manufacturing of a stent. Stainless steel includes a chromium oxide surface layer which makes the stent corrosion resistant and confers, in large part, biocompatibility properties to the stent. The chromium oxide layer presents oxide, anionic groups, and hydroxyl moieties, which are polar. Consequently, polymeric materials with polar substituents and cationic groups can adhere to the surface.

Representative examples of suitable polymeric materials include polyisocyanates, unsaturated polymers, high amine content polymers, acrylates, polymers with high content of hydrogen bonding groups, silane coupling agents, titanates and zirconates.

Representative examples of polyisocyanates include triisocyanurate, alphatic polyisocyanate resins based on hexamethylene diisocyanate, aromatic polyisocyanate prepolymers based on diphenylmethane diisocyanate, polyisocyanate polyether polyurethanes based on diphenylmethane diisocyanate, polymeric isocyanates based on toluene diisocyanate, polymethylene polyphenyl isocyanate, and polyester polyurethanes.

Representative examples of unsaturated polymers include polyester diacrylates, polycaprolactone diacrylates, polyester diacrylates, polytetramethylene glycol diacrylate, polyacrylates with at least two acrylate groups, polyacrylated polyurethanes, and triacrylates. With the use of unsaturated prepolymers a free radical or UV initiator can be added to the composition for the thermal or UV curing or cross-linking process. For thermal curing, examples of free radicals initiators are benzoyl peroxide; bis(2,4-dichlorobenzoyl) peroxide; dicumyl peroxide; 2,5-bis(tert-butyl peroxy)-2,5-dimethyl hexane; ammonium persulfate, and 2,2'-azobisisobutyronitrile. As is understood by one of ordinary skill in the art, each initiator requires a different temperature to induce decomposition. For UV curing, examples of initiators include 2,2-dimethoxy-2-phenylacetophenone; 1-hydroxycyclohexyl phenyl ketone; benzoin ethyl ether; and benzophenone. These initiators can be activated by illumination with a medium pressure Hg bulb that contains wavelengths between 250 and 350 nm.

Representative examples of high amine content polymers include polyethyleneamine, polyallylamine, and polylysine.

Representative examples of acrylates include copolymers of ethyl acrylate, methyl acrylate, butyl methacrylate, methacrylic acid, acrylic acid, and cyanoacrylates.

Representative examples of high content of hydrogen bonding group polymers include polyethylene-co-polyvinyl alcohol, epoxy polymers based on the diglycidylether of bisphenol A with amine crosslinking agents, epoxy polymers cured by polyols and lewis acid catalysts, epoxy phenolics, epoxy-polysulfides, ethylene vinyl acetate, melamine formaldehydes, polyvinylalcohol-co-vinyl acetate polymers, resorcinol-formaldehydes, urea-formaldehydes, polyvinylbutyral, polyvinylacetate, alkyd polyester resins, acrylic acid modified ethylene vinyl acetate polymers, methacrylic acid modified ethylene vinyl acetate polymers, acrylic acid modified ethylene acrylate polymers, methacrylic acid modified ethylene acrylate polymers, anhydride modified ethylene acrylate butylene, and anhydride modified ethylene vinyl acetate polymers.

Representative examples of silane coupling agents include 3-aminopropyltriethoxysilane and (3-glydidoxypropyl)methyldiethoxysilane.

Representative examples of titanates include tetra-iso-propyl titanate and tetra-n-butyl titanate.

Representative examples of zirconates include n-propyl zirconate and n-butyl zirconate.

Other polymers can be used for the primer material. Representative examples of polymers for the primer layer include ethylene vinyl alcohol copolymer; poly(butylmethacrylate); copolymers of vinyl monomers with each other and olefins, such as ethylene-methyl methacrylate copolymers, acrylonitrile-styrene copolymers, ABS resins, and ethylene-vinyl acetate copolymers; poly(hydroxyvalerate); poly(epsilon-caprolactone); poly(lactide-co-glycolide); poly(hydroxybutyrate); poly(hydroxybutyrate-co-valerate); polydioxanone; polyorthoester; polyanhydride; poly(glycolic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; poly(lactic acid)-block-polyphosphazene, styrene-block-isobutylene and carboxymethyl cellulose.

Ethylene vinyl alcohol is functionally a very suitable choice of polymer. Ethylene vinyl alcohol copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 47%. Typically, 44 mole percent ethylene is suitable. Ethylene vinyl alcohol copolymer is available commercially from companies such as Aldrich Chemical Company, Milwaukee, Wis., or EVAL Company of America, Lisle, Ill., or can be prepared by conventional polymerization procedures that are well known to one of ordinary skill in the art. The copolymer possesses good adhesive qualities to the surface of a stent, particularly stainless steel surfaces, and has illustrated the ability to expand with a stent without any significant detachment of the copolymer from the surface of the stent.

In one embodiment of the present invention, the polymer in the primer layer is a biologically degradable polymer. The terms "biologically degradable," "biologically erodable,"

"biologically absorbable," and "biologically resorbable" polymers, which are used interchangeably, are defined as polymers that are capable of being completely degraded, dissolved, and/or eroded over time when exposed to bodily fluids such as blood and are gradually resorbed, absorbed and/or eliminated by the body. The processes of breaking down and eventual absorption and elimination of the polymer can be caused, for example, by hydrolysis, metabolic processes, bulk or surface erosion, and the like.

Whenever the reference is made to "biologically degradable," "biologically erodable," "biologically resorbable," and "biologically absorbable" stent coatings and/or polymers forming such stent coatings, it is understood that after the process of degradation, erosion, absorption, or resorption has been completed, no coating will remain on the stent. In some embodiments, traces or residues may remain. The terms "degradable," "biodegradable," or "biologically degradable" are intended to broadly include biologically degradable, biologically erodable, biologically absorbable, and biologically resorbable coatings and/or polymers.

In one embodiment, a stent that is made in whole or in part from a biodegradable polymer or a combination of biodegradable polymers is subjected to the thermal treatment in accordance to the various embodiments of the invention.

In a particular embodiment of the present invention, the biologically degradable, erodable, absorbable and/or resorbable polymers that can be used for making the primer layer includes at least a poly(lactic acid). Poly(lactic acid) includes poly(D,L-lactic acid) (DLPLA), poly(D-lactic acid) (DPLA) and poly(L-lactic acid) (LPLA).

The stereochemical composition of the poly(lactic acid) can dramatically affect the properties of the poly(lactic acid). For example, it has been reported that LPLA can be a semi-crystalline polymer that can have a $T_g$ of about 67° C., and a $T_m$ of about 180° C. On the other hand, DLPLA can be an amorphous polymer that can have a $T_g$ of about 58° C. or lower. See, e.g., Reeve et al., Polylactide Stereochemistry: Effect of Enzymatic Degradability, Macromolecules 27(3), 825-31 (1994). It should be noted that the amorphous form of PLA may have certain performance advantages as a component of stent coatings; for example, it has been found that DLPLA is more readily absorbable under biological conditions than LPLA.

Poly(lactic acid) has the formula H—[O—CH(CH₃)—C(O)]ₙ—OH and can be obtained by ring-opening polymerization of lactide (a cyclic dimer of lactic acid), as demonstrated schematically by reaction (I), where lactide is compound (A) and poly(lactic acid) is compound (B):

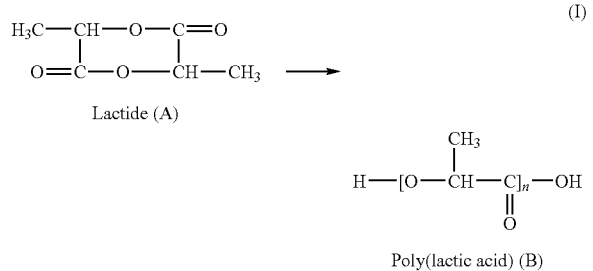

The molecular weight of poly(lactic acid) can be for example about 30,000 to about 300,000 Daltons. The molecular weight is proportional to the value of the integer n in the compound (B), which can be for example about 416 to about 4,166. Those having ordinary skill in the art can determine the conditions under which the transformation of lactide to poly(lactic acid) illustrated by reaction (I) can be carried out.

Alternatively, polymers containing moieties derived from poly(lactic acid) can be also used in addition to or instead of, poly(lactic acid), for making the primer layer. One type of alternative polymers based on poly(lactic acid) includes derivatives of poly(lactic acid), for example, hydrolyzed or carboxylated poly(lactic acid), or a blend thereof. Using the hydrolyzed or carboxylated poly(lactic acid) is expected to result in the increased rate of degradation of the coating.

The hydrolyzed poly(lactic acid) is a polymeric product comprising a mixture of the original (unhydrolized) poly(lactic acid) (B) and oligomeric and/or polymeric products of the hydrolysis thereof. The products of hydrolysis can include a complex mixture of oligomers of lactic acid, monomeric lactic acid and other products that can include hydroxylated species. The mixture can contain about 1 mass % to about 20 mass % original poly(lactic acids) (B) having the molecular weight as indicated above, and the balance, the products of hydrolysis thereof. The oligomeric and/or polymeric products of hydrolysis of poly(lactic acid) can have an average molecular weight of about 1,000 to about 20,000 Daltons.

To obtain the hydrolyzed poly(lactic acid), poly(lactic acid) can be hydrolyzed under the condition that can be selected by those having ordinary skill in the art. The process of hydrolysis is polymer-analogous transformation and can be carried out until the mixture of poly(lactic acid) and the products of hydrolysis thereof are obtained, the mixture having a desired ratio between poly(lactic acid) and the products of hydrolysis thereof. The desired ratio can be also determined by those having ordinary skill in the art.

The carboxylated poly(lactic acid) comprises poly(lactic acid) terminated with a carboxyl group and can be obtained by ring-opening polymerization of lactide (A), in the presence of a butylene acid (HO—R—COOH) serving as a ring opening catalyst as demonstrated schematically by reaction (II), where the carboxylated poly(lactic acid) is compound (C):

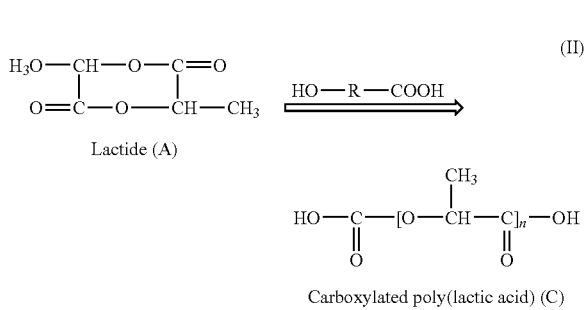

Hydroxy acid (HO—R—COOH), the ring-opening catalyst in reaction (II) can be any suitable butylene acid that can be selected by those having ordinary skill in the art. One example of butylene acid that can be used is hydroacetic (glycolic) acid.

The carboxylated poly(lactic acid) can be a fully carboxylated poly(lactic acid), i.e., can be a 100% product (C). The molecular weight of the fully carboxylated poly(lactic acid) can be about 1,000 to about 20,000 Daltons. The fully carboxylated poly(lactic acid) can be obtained from Birmingham Polymers, Inc. of Birmingham, Ala.

The carboxylated poly(lactic acid) can also be in a mixture with original poly(lactic acid) (B). The mixture can contain between about 1 mass % to about 20 mass % original poly (lactic acid) (B) having the molecular weight as indicated above, and the balance, the carboxylated poly(lactic acid) (C).

Another type of polymer based on poly(lactic acid) that can be used for the primer layer includes graft copolymers, and block copolymers, such as AB block-copolymers ("diblock-copolymers") or ABA block-copolymers ("triblock-copolymers"), or mixtures thereof. The molecular weight of blocks A can be about 300 to about 40,000 Daltons, more narrowly, about 8,000 to about 30,000 Daltons, for example, about 15,000 Daltons. The molecular weight of blocks B can be about 50,000 to about 250,000 Daltons, more narrowly, about 80,000 to about 200,000 Daltons, for example, about 100,000 Daltons.

The terms "block-copolymer" and "graft copolymer" are defined in accordance with the terminology used by the International Union of Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions. "Graft copolymer" refers to a polymer composed of macromolecules with one or more species of block connected to the main chain as side chains, these side chains having constitutional or configuration features that differ from those in the main chain.

The term "AB block-copolymer" is defined as a block-copolymer having moieties A and B arranged according to the general formula -$\{[A-]_m-[B]_n\}_{-x}$, where each of "m," "n," and "x" is a positive integer, and $m \geq 2$, and $n \geq 2$.

The term "ABA block-copolymer" is defined as a block-copolymer having moieties A and B arranged according to the general formula -$\{[A-]_m-[B]_n-[A-]_p\}_{-x}$, where each of "m," "n," "p," and "x" is a positive integer, and $m \geq 2$, and $n \geq 2$, and $p \geq 2$.

The blocks of the ABA and AB block-copolymers need not be linked on the ends, since the values of the integers determining the number of A and B blocks are such as to ensure that the individual blocks are usually long enough to be considered polymers in their own right. Accordingly, the ABA block copolymer can be named poly A-block-co-poly B block-co-poly block-copolymer, and the AB block copolymer can be named poly A-block-co-poly B block-copolymer. Blocks "A" and "B," can be larger than the three-block size and can be alternating or random. Note that the term "copolymer" encompasses for the purposes of this disclosure a polymer with two or more constituent monomers and does not imply a polymer of only two monomers.

In one embodiment, the block polymers or graft polymers of the present invention include a biologically compatible moiety. For example, both ABA and AB block-copolymers can be used to contain the block(s) of poly(lactic acid), and block(s) of a biologically compatible moiety, providing the AB or ABA block-copolymer with blood compatibility. To illustrate, in one embodiment, moiety A is poly(lactic acid) and moiety B is the biocompatible moiety. In another embodiment, moiety B is poly(lactic acid), and moiety A is the biocompatible moiety. In one embodiment, the biocompatible moieties are selected in such a way so that to make the entire ABA and AB block-copolymers biologically degradable.

Examples of suitable biocompatible moieties include poly (alkylene glycols), for example, poly(ethylene-glycol) (PEG), poly(ethylene oxide), poly(propylene glycol) (PPG), poly(tetramethylene glycol), or poly(ethylene oxide-co-propylene oxide); lactones and lactides, for example, ε-caprolactone, β-butyrolactone, δ-valerolactone, or glycolide; poly(N-vinyl pyrrolidone); poly(acrylamide methyl propane sulfonic acid) and salts thereof (AMPS and salts thereof); poly(styrene sulfonate); sulfonated dextran; polyphosphazenes; poly (orthoesters); poly(tyrosine carbonate); hyaluronic acid; hyaluronic acid having a stearoyl or palmitoyl substituent group; copolymers of PEG with hyaluronic acid or with hyaluronic acid-stearoyl, or with hyaluronic acid-palmitoyl; heparin; copolymers of PEG with heparin; a graft copolymer of poly(L-lysine) and PEG; or copolymers thereof. A molecular weight of a suitable biocompatible polymeric moiety can be below 40,000 Daltons to ensure the renal clearance of the compound, for example, between about 300 and about 40,000 Daltons, more narrowly, between about 8,000 and about 30,000 Daltons, for example, about 15,000 Daltons. Lactones and lactides mentioned above can also replace a part or all of DLPLA in the block-copolymer, if desired.

Accordingly, one example of the AB block copolymer that can be used is poly(D,L-lactic acid)-block-poly(ethylene-glycol) (DLPLA-PEG). One possible structure of the DLPLA-PEG lock-copolymer is shown by formula (III):

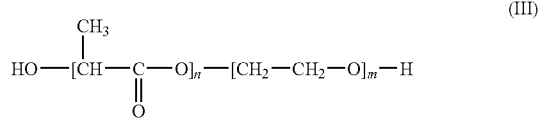

(III)

The DLPLA-PEG block-copolymer shown by formula (III) can have a total molecular weight of about 30,000 to about 300,000 Daltons, for example, about 60,000 Daltons as measured by the gel-permeation chromatography (GPC) method in tetrahydrofuran. The molecular weight of the PEG blocks can be about 500 to about 30,000 Daltons, for example, about 550 Daltons, and the molecular weight of the DLPLA blocks can be about 1,500 to about 20,000 Daltons, for example, about 1,900 Daltons. Accordingly, in formula (III), "n" is an integer that can have a value of about 21 to about 278, and "m" is an integer that can have a value of about 11 to about 682.

One example of the ABA block copolymer that can be used is poly(D,L-lactic acid)-block-poly(ethylene-glycol)-block-poly(D,L-lactic acid) (DLPLA-PEG-DLPLA). One possible structure of the DLPLA-PEG-DLPLA block-copolymer is shown by formula (IV):

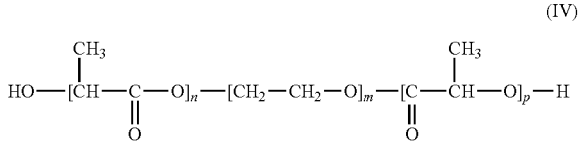

(IV)

The DLPLA-PEG-DLPLA block-copolymer shown by formula (IV) can have a total molecular weight of about 30,000 to about 300,000 Daltons, for example, about 60,000 Daltons as measured by a GPC method in tetrahydrofuran. The molecular weight of the PEG blocks can be about 500 to about 30,000 Daltons, for example, about 7,500 Daltons; and the molecular weight of the DLPLA blocks can be about 1,500 to about 20,000 Daltons, for example, one terminal DLPLA block can have the molecular weight of about 3,400 Daltons, and the other terminal DLPLA block can have the molecular weight of about 10,000 Daltons. Accordingly, in formula (IV), "n" is an integer that can have a value of about 21 to about 278; "m" is an integer that can have a value of about 11 to about 682; and "p" is an integer that can have a value of about 21 to about 278.

If desired, the positions of the moieties can be switched to obtain a BAB block-copolymer, poly(ethylene-glycol)-block-poly(D,L-lactic acid)-block-poly(ethylene-glycol) (PEG-DLPLA-PEG). One possible structure of the PEG-DLPLA-PEG block-copolymer is shown by formula (V):

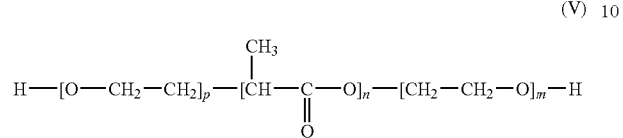

(V)

The PEG-DLPLA-PEG block-copolymer shown by formula (V) can have a total molecular weight of about 30,000 to about 300,000 Daltons, for example, about 60,000 Daltons as measured by the GPC method in tetrahydrofuran. The molecular weight of the PEG block can be about 500 to about 30,000 Daltons, for example, about 7,500 Daltons; and the molecular weight of the DLPLA blocks can be about 1,500 to about 20,000 Daltons. Accordingly, in formula (V), "n" is an integer that can have a value of about 21 to about 278; "m" is an integer that can have a value of about 11 to about 682, and "p" is an integer that can have a value of about 11 to about 682.

Block-copolymers shown by formulae (III-V) can be synthesized by standard methods known to those having ordinary skill in the art, for example, copolycondensation of PEG with DLPLA. The process of copolycondensation can be catalyzed by an acid or a base, if necessary.

According to one embodiment, hydrolyzed block copolymers of PEG and DPLA can be used for making the stent coatings. Both AB and ABA and BAB block-copolymers discussed above can be used to obtain the hydrolyzed block copolymers of PEG and DPLA. The hydrolyze block copolymers of PEG and DPLA are polymeric products comprising a mixture of block copolymers of PEG and DPLA and products of partial hydrolysis thereof. The mixture can contain about 1 mass % to about 20 mass % unhydrolyzed block copolymers of PEG and DPLA and the balance, the products of hydrolysis thereof.

To obtain the hydrolyzed block copolymers of PEG and DPLA, the block-copolymers can be hydrolyzed under the conditions that can be selected by those having ordinary skill in the art. The process of hydrolysis can be carried out until the mixture of the block-copolymer and the products of partial hydrolysis thereof is obtained, the mixture having a desired ratio between the block-copolymer and the products of partial hydrolysis thereof. The desired ratio can be also determined by those having ordinary skill in the art.

In accordance with other embodiments of the present invention, the biologically degradable polymer in the primer layer includes:
(a) poly(hydroxybutyrate) (PHB);
(b) poly(hydroxyvalerate) (PHV);
(c) poly(hydroxybutyrate-co-valerate);
(d) poly(caprolactone) (PCL);
(e) poly(lactide-co-glycolide) (PLGA);
(f) poly(glycerol-sebacate) (PGS);
(g) poly(ester amide);
(h) collagen;
(i) elastin;
(j) silk;
(k) AB and ABA block-copolymers of PEG with poly (butylene terephthalate) (PBT), e.g., poly(ethylene-glycol)-block-poly(butylene terephthalate) (PEG-PBT), poly(ethylene-glycol)-block-poly(butylene terephthalate)-block-poly(ethylene-glycol) (PEG-PBT-PEG), or poly(butylene terephthalate)-block-poly(ethylene-glycol)-block poly(butylene terephthalate) (PBT-PEG-PBT); and
(l) AB and ABA block-copolymers of PEG with PCL, e.g., poly(ethylene-glycol)-block-poly(caprolactone) (PEG-PCL), poly(ethylene-glycol)-block-poly(caprolactone)-block-poly(ethylene-glycol) (PEG-PCL-PEG), or poly (caprolactone)-block-poly(ethylene-glycol)block-poly (caprolactone) (PCL-PEG-PCL).

Any mixture of compounds of groups (a)-(l) described above can be also used. PEG-PBT and PEG-PBT-PEG block copolymers are known under a trade name POLYACTIVE and are available from IsoTis Corp. of Holland. These polymers can be obtained, for example, by trans-esterification of dibutylene terephthalate with PEG. In POLYACTIVE, the ratio between the units derived from ethylene glycol and the units derived from butylene terephthalate can be about 0.67:1 to about 9:1. The molecular weight of the units derived from ethylene glycol can be about 300 to about 4,000 Daltons, and the molecular weight of the units derived from butylene terephthalate can be about 50,000 to about 250,000, for example, about 100,000 Daltons.

DLPLA-PEG-DLPLA, PEG-DLPLA-PEG, PEG-PBT, PEG-PBT-PEG, PBT-PEG-PBT, PEG-PCL, PEG-PCL-PEG, and PCL-PEG-PCL block copolymers all contain fragments with ester bonds. Ester bonds are known to be water-labile bonds. When in contact with slightly alkaline blood, ester bonds are subject to catalyzed hydrolysis, thus ensuring biological degradability of the block-copolymer. One product of degradation of every block polymer, belonging to the group DLPLA-PEG-DLPLA, PEG-DLPLA-PEG, PEG-PBT, PEG-PBT-PEG, PBT-PBG-PBT, PEG-PCL, PEG-PCL-PEG, and PCL-PEG-PCL is expected to be PEG, which is highly biologically compatible.

If a solvent is used to form a polymer composition for application to the stent, the solvent should be mutually compatible with the polymer and should be capable of placing the polymer into solution at the concentration desired in the solution. Useful solvents should also be able to expand the chains of the polymer for maximum interaction with the surface of the device, such as a metallic surface of a stent. Examples of solvent can include, but are not limited to, dimethylsulfoxide (DMSO), dimethyl acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof. Examples of mixtures of solvents include:
(1) DMAC and methanol (e.g., a 50:50 by mass mixture);
(2) water, i-propanol, and DMAC (e.g., a 10:3:87 by mass mixture);
(3) i-propanol and DMAC (e.g., 80:20, 50:50, or 20:80 by mass mixture);
(4) acetone and cyclohexanone (e.g., 80:20, 50:50, or 20:80 by mass mixture);
(5) acetone and xylene (e.g., a 50:50 by mass mixture);
(6) acetone, FLUX REMOVER AMS, and xylene (e.g., a 10:50:40 by mass mixture); and
(7) 1,1,2-trichloroethane and chloroform (e.g., an 80:20 by mass mixture).

By way of example, and not limitation, the polymer can comprise from about 0.1% to about 35%, more narrowly about 2% to about 20% by weight of the total weight of the composition, and the solvent can comprise from about 65% to about 99.9%, more narrowly about 80% to about 98% by weight of the total weight of the composition. A specific weight ratio is dependent on factors such as the material from which the implantable device is made and the geometrical structure of the device.

Figure 6A:
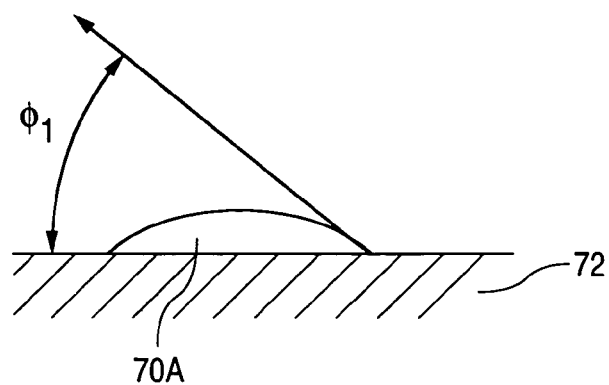
FIG. 6A illustrates a fluid on a solid substrate having a contact angle $\Phi_1$.
Figure 6B:
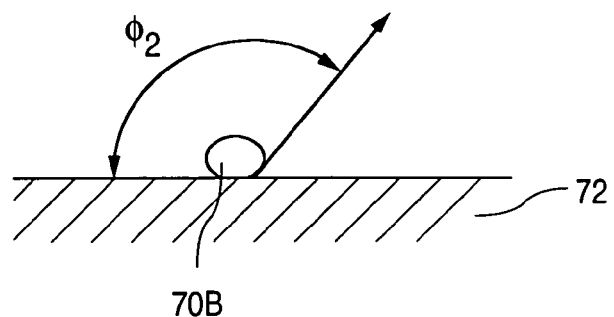
FIG. 6B illustrates a fluid on a solid substrate having a contact angle $\Phi_2$.

A fluid can be added to the composition to enhance the wetting of the composition for a more uniform coating application. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 6A illustrates a fluid droplet 70A on a solid substrate 72, for example a stainless steel surface. Fluid droplet 70A has a high capillary permeation that corresponds to a contact angle $\Phi_1$, which is less than about 90°. In contrast, FIG. 6B illustrates a fluid droplet 70B on solid substrate 72, having a low capillary permeation that corresponds to a contact angle $\Phi_2$, which is greater than about 90°. The wetting fluid, typically, should have a viscosity not greater than about 50 centipoise, narrowly about 0.3 to about 5 centipoise, more narrowly about 0.4 to about 2.5 centipoise. The wetting fluid, accordingly, when added to the composition, reduces the viscosity of composition.

The wetting fluid should be mutually compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. By way of example and not limitation, the polymer can comprise from about 0.1% to about 35%, more narrowly from about 2% to about 20% by weight of the total weight of the composition; the solvent can comprise from about 19.9% to about 98.9%, more narrowly from about 58% to about 84% by weight of the total weight of the composition; the wetting fluid can comprise from about 1% to about 80%, more narrowly from about 5% to about 40% by weight of the total weight of the composition. The specific weight ratio of the wetting fluid depends on the type of wetting fluid employed and type of and the weight ratio of the polymer and the solvent. More particularly, tetrahydrofuran used as the wetting fluid can comprise, for example, from about 1% to about 44%, more narrowly about 21% by weight of the total weight of the solution. Dimethylformamide used as the wetting fluid can comprise, for example, from about 1% to about 80%, more narrowly about 8% by weight of the total weight of the solution. 1-butanol used as the wetting fluid can comprise, for example, from about 1% to about 33%, more narrowly about 9% by weight of the total weight of the solution. N-butyl acetate used as the wetting fluid can comprise, for example, from about 1% to about 34%, more narrowly about 14% by weight of the total weight of the solution. DMAC used as the wetting fluid can comprise, for example, from about 1% to about 40%, more narrowly about 20% by weight of the total weight of the solution.

Table 5 illustrates some examples of suitable combinations for the primer composition:

TABLE 5

| Polymer | Solvent | Wetting Fluid | Initiators |
|---|---|---|---|
| EVOH | DMSO | — | — |
| EVOH | DMSO | THF | — |
| polyester polyurethanes | dimethylformamide | — | — |
| polyester polyurethanes | dimethylformamide | DMAC | — |
| polycaprolactone | chloroform | n-butyl acetate | — |
| polyacrylate polyurethane | ethyl acetate | — | benzophenone |
| polyacrylated polyurethane | ethyl acetate | — | 1-hydroxy-cyclohexyl phenyl ketone |
| polyethyleneamine | $H_2O$ | — | — |
| methacrylic acid copolymer | THF | — | — |
| ethylene vinylacetate (e.g., 40% vinyl acetate content) | methylethylketone | — | — |
| aminopropyl-triethoxysilane | ethanol/water 95/5 blend (w/w) | — | — |
| (3-glycidoxypropyl) methyldiethoxysilane | toluene | — | — |
| tetra-iso-propyl titanate (e.g., 0.25% w/w in isopropanol) | isopropanol | — | — |
| tetra-n-butyl titanate (e.g., 0.1-5% w/w in ethyl acetate) | ethyl acetate | — | — |

With the use of a thermoset polymer, an initiator may be required. By way of example, epoxy systems consisting of diglycidyl ether of bisphenol A resins can be cured with amine curatives, thermoset polyurethane prepolymers can cured with polyols, polyamines, or water (moisture), and acrylated urethane can be cured with UV light. Examples 27 and 28 provide illustrative descriptions. If baked, the temperature can be above the $T_g$ of the selected polymer.

With the use of the inorganic polymers, such as silanes, titanates, and zirconates the composition containing the prepolymer or precursor is applied and the solvent is allowed to evaporate. Example 29 provides a brief description.

Forming an Active Agent-Containing Coating

The composition containing the active agent can be prepared by first forming a polymer solution by adding a predetermined amount of a polymer to a predetermined amount of a compatible solvent. The polymer can be added to the solvent at ambient pressure and under anhydrous atmosphere. If necessary, gentle heating and stirring and/or mixing can be employed to effect dissolution of the polymer into the solvent, for example 12 hours in a water bath at about 60° C.

Sufficient amounts of the active agent can then be dispersed in the blended composition of the polymer and the solvent. The active agent can be mixed with the polymer solution so that the active agent forms a true solution or becomes saturated in the blended composition. If the active agent is not completely soluble in the composition, operations including mixing, stirring, and/or agitation can be employed to effect homogeneity of the residues. The active agent can also be first added to a solvent that is capable of more readily dissolving the active agent prior to admixing with the polymer composition. The active agent can also be added so that the dispersion is in fine particles.

The polymer can comprise from about 0.1% to about 35%, more narrowly from about 0.5% to about 20% by weight of the total weight of the composition, the solvent can comprise from about 59.9% to about 99.8%, more narrowly from about 79% to about 99% by weight of the total weight of the composition, and the active agent can comprise from about 0.1% to about 40%, more narrowly from about 1% to about 9% by weight of the total weight of the composition. Selection of a specific weight ratio of the polymer and solvent is dependent on factors such as, but not limited to, the material from which the device is made, the geometrical structure of the device, the type and amount of the active agent employed, and the release rate desired.

Representative examples of polymers that can be combined with the active agent for the reservoir layer include the polymers noted above for the primer layer. Ethylene vinyl alcohol copolymer, for example, is functionally a very suitable choice of polymer because ethylene vinyl alcohol copolymer allows for good control capabilities of the release rate of the active agent. As a general rule, an increase in the amount of the ethylene comonomer content decreases the rate that the active agent is released from the copolymer matrix. The release rate of the active agent typically decreases as the hydrophilicity of the copolymer decreases. An increase in the amount of the ethylene comonomer content increases the overall hydrophobicity of the copolymer, especially as the content of vinyl alcohol is concomitantly reduced. It is also thought that the release rate and the cumulative amount of the active agent that is released is directly proportional to the total initial content of the agent in the copolymer matrix. Accordingly, a wide spectrum of release rates can be achieved by modifying the ethylene comonomer content and the initial amount of the active agent.

Poly(butylmethacrylate) ("PBMA") and ethylene-vinyl acetate copolymers can also be especially suitable polymers for the reservoir layer. In one embodiment, the polymer in the reservoir coating is a mixture of PBMA and an ethylene-vinyl acetate copolymer.

In one embodiment of the invention, the polymer in the reservoir layer is a biologically biodegradable polymer, such as one of the polymers listed above for formation of the primer layer. The biological degradation, erosion, absorption and/or resorption of a biologically degradable, absorbable and/or resorbable polymer are expected to cause the release rate of the drug due to the gradual disappearance of the polymer that is included in the reservoir layer. By choosing an appropriate degradable polymer the stent coating can be engineered to provide either fast or slow release of the drug, as desired. Those having ordinary skill in the art can determine whether a stent coating having slow or fast release rate is advisable for a particular drug. For example, fast release may be recommended for stent coatings loaded with antimigratory drugs which often need to be released within 1 to 2 weeks. For antiproliferative drugs, slow release may be needed (up to 30 days release time).

Representative examples of solvents include the solvents listed above for the primer layer. The active agent may be any substance capable of exerting a therapeutic or prophylactic effect in the practice of the present invention. Exposure of the composition to the active agent should not adversely alter the active agent's composition or characteristic. Accordingly, the particular active agent is selected for compatibility with the blended composition.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., TAXOTERE®, from Aventis S.A., Frankfurt, Germany), methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (bivalirudin, Biogen, Inc., Cambridge, Mass.). Examples of such cytostatic or antiproliferative agents include angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., PRINVIL® and PRINZIDE® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin; serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, anti-inflammatory agents, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6, 6-tetramethylpiperidine-1-oxyl (4-amino-TEMPO), tacrolimus, dexamethasone, rapamycin, rapamycin derivatives, ABT-578, clobetasol, cytostatic agents, prodrugs thereof, co-drugs thereof, and a combination thereof.

Rapamycin can be a very suitable choice of active agent. Additionally, 40-O-(2-hydroxy)ethyl-rapamycin (everolimus), or a functional analog or structural derivative thereof, can be an especially functional choice of active agent. Examples of analogs or derivatives of 40-O-(2-hydroxy) ethyl-rapamycin include but are not limited to 40-O-(3-hydroxy)propyl-rapamycin and 40-O-[2-(2-hydroxy)ethoxy] ethyl-rapamycin, and 40-O-tetrazole-rapamycin.

40-O-(2-hydroxy)ethyl-rapamycin binds to the cytosolic immunophyllin FKBP12 and inhibits growth factor-driven cell proliferation, including that of T-cells and vascular smooth muscle cells. The actions of 40-O-(2-hydroxy)ethyl-rapamycin occur late in the cell cycle (i.e., late G1 stage) compared to other immunosuppressive agents such as tacrolimus or cyclosporine which block transcriptional activation of early T-cell-specific genes. Since 40-O-(2-hydroxy)ethyl-rapamycin can act as a potent anti-proliferative agent, it is believed that 40-O-(2-hydroxy)ethyl-rapamycin can be an effective agent to treat restenosis by being delivered to a local treatment site from a polymeric coated implantable device such as a stent.

The release rate of 40-O-(2-hydroxy)ethyl-rapamycin can be advantageously controlled by various methods and coatings as described herein. In particular, by using the methods and coatings of the present invention, the release rate of the 40-O-(2-hydroxy)ethyl-rapamycin, or analog or derivative thereof, can be less than about 50% in 24 hours.

When the 40-O-(2-hydroxy)ethyl-rapamycin is blended with a polymer for the reservoir layer, the ratio of 40-O-(2-hydroxy)ethyl-rapamycin, or analog or derivative thereof, to polymer by weight in the reservoir layer can be about 1:2.8 to about 1:1. The 40-O-(2-hydroxy)ethyl-rapamycin, or analog or derivative thereof, in the reservoir layer can be in the amount of about 50 μg to about 500 μg, more narrowly about 90 μg to about 350 μg, and the polymer is in the amount of about 50 μg to about 1000 μg, more narrowly about 90 μg to about 500 μg.

The dosage or concentration of the active agent required to produce a therapeutic effect should be less than the level at which the active agent produces unwanted toxic effects and greater than the level at which non-therapeutic effects are obtained. The dosage or concentration of the active agent required to inhibit the desired cellular activity of the vascular region, for example, can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Forming a Barrier Layer to Reduce the Rate of Release

In some coatings, the release rate of the active agent may be too high to be clinically useful. For example, as shown in Example 58 below, for 40-O-(2-hydroxy)ethyl-rapamycin the percentage of 40-O-(2-hydroxy)ethyl-rapamycin released from a stent coating without a barrier layer in 24 hours was determined to be 58.55% as measured in a porcine serum release rate procedure. The release rate from the coating of Example 58 may be too high for a treatment using 40-O-(2-hydroxy)ethyl-rapamycin as the active agent. A barrier layer can reduce the rate of release or delay the time at which the active agent is released from the reservoir layer.

In accordance with one embodiment, the barrier layer can be applied on a selected region of the reservoir layer to form a rate reducing member. The barrier layer can be applied to the reservoir layer prior to or subsequent to the heat treatment. The composition for the barrier layer can be free or substantially free of active agents. Incidental migration of the active agent into the barrier layer can occur during or subsequent to the formation of the barrier layer. Alternatively, for maximum blood compatibility, compounds such as poly(ethylene glycol), heparin, heparin derivatives having hydrophobic counterions, or polyethylene oxide can be added to the barrier layer, or disposed on top of the barrier layer. The addition can be by blending, mixing, conjugation, bonding, etc.

The choice of polymer for the barrier layer can be the same as the selected polymer for the primer layer and/or reservoir layer. The use of the same polymer, as described for some of the embodiments, significantly reduces or eliminates any interfacial incompatibilities, such as lack of cohesion, which may exist in the employment of two different polymeric layers.

Polymers that can be used for a barrier layer include the examples of polymers listed above for the primer layer and/or reservoir layer. Representative examples of polymers for the barrier layer also include polytetrafluoroethylene, perfluoro elastomers, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, polybutenes, styrene-ethylene-styrene block copolymers, styrene-butylene-styrene block copolymers, styrene-butadiene-styrene block copolymers, and ethylene methacrylic acid copolymers of low methacrylic acid content.

Ethylene vinyl alcohol copolymer is functionally a very suitable choice of polymer for the barrier layer. Fluoropolymers are also a suitable choice for the barrier layer composition. For example, polyvinylidene fluoride (otherwise known as KYNAR™, available from Atofina Chemicals, Philadelphia, Pa.) can be dissolved in acetone, methylethylketone, DMAC, and cyclohexanone, and can optionally be combined with ethylene vinyl alcohol copolymer to form the barrier layer composition. Also, solution processing of fluoropolymers is possible, particularly the low crystallinity varieties such as CYTOP™ available from Asahi Glass and TEFLON AF™ available from DuPont. Solutions of up to about 15% (wt/wt) are possible in perfluoro solvents, such as FC-75 (available from 3M under the brand name FLUORINERT™), which are non-polar, low boiling solvents. Such volatility allows the solvent to be easily and quickly evaporated following the application of the polymer-solvent solution to the implantable device.

PBMA and ethylene-vinyl acetate copolymers can also be especially suitable polymers for the barrier layer. PBMA, for example, can be dissolved in a solution of xylene, acetone and HFE FLUX REMOVER™ (Techspray, Amarillo, Tex.). The polymer in the barrier layer can be a mixture of PBMA and an ethylene-vinyl acetate copolymer.

The barrier layer can also be styrene-ethylene/butylene-styrene block copolymer. Styrene-ethylene/butylene-styrene block copolymer, e.g., KRATON™ G-series, can be dissolved in non-polar solvents such as, but not limited to, toluene, xylene, and decalin.

Other choices of polymers for the rate-limiting membrane include, but are not limited to, ethylene-anhydride copolymers; and ethylene-acrylic acid copolymers having, for example, a mole % of acrylic acid of from about 2% to about 25%. The ethylene-anhydride copolymer available from Bynel adheres well to ethylene vinyl alcohol copolymer and thus would function well as a barrier layer over a reservoir layer made from ethylene vinyl alcohol copolymer. The copolymer can be dissolved in organic solvents, such as dimethylsulfoxide and DMAC. Ethylene vinyl acetate polymers can be dissolved in organic solvents, such as toluene and n-butyl acetate. Ethylene-acrylic acid copolymers can be dissolved in organic solvents, such as methanol, isopropyl alcohol, and dimethylsulfoxide.

Yet another choice of polymer for the rate-limiting membrane is a cross-linked silicone elastomer. Loose silicone and silicone with very low cross-linking are thought to cause an inflammatory biological response. However, it is believed that a thoroughly cross-linked silicone elastomer, having low levels of leachable silicone polymer and oligomer, is an essentially non-inflammatory substance.

Silicone elastomers, such as Nusil MED-4750™, MED-4755™, or MED2-6640™, having high tensile strengths, for example between 1200 psi and 1500 psi, will likely have the best durability during crimping, delivery, and expansion of a stent as well as good adhesion to a reservoir layer, e.g., ethylene vinyl alcohol copolymer or the surface of an implantable device.

The composition for a rate-reducing membrane or diffusion barrier layer can be prepared by the methods used to prepare a polymer solution as described above. The polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the composition. Selection of a specific weight ratio of the polymer and solvent is dependent on factors such as, but not limited to, the type of polymer and solvent employed, the type of underlying reservoir layer, and the method of application.

Forming a Finishing Layer

Depending on the polymer used for the reservoir or barrier layers, it may be advantageous to form a finishing layer that is especially biocompatible on the surface of the coating that is exposed to the biological lumen when inserted into a patient. The finishing layer can be formed on the surface of the coating subsequent to the thermal treatment. Representative examples of biocompatible polymers or biocompatible agents for the finishing layer include, but are not limited to polyethylene oxide, poly(ethylene glycol), hyaluronic acid, polyvinyl pyrrolidone, heparin, heparin derivatives such as those having hydrophobic counterions, and phosphylcholine.

Methods for Applying the Compositions to the Device

The primer composition can first be applied to the stent. Application of the composition can be by any conventional method, such as by spraying the composition onto the prosthesis, using a controlled deposition system or by immersing the prosthesis in the composition. A representative example of a spray coating device is the EFD 780S device with VALVEMATE™ 7040 control system (manufactured by EFD Inc., East Providence, R.I.). A representative example of a controlled deposition system is described in U.S. Pat. No. 6,395,326 to Castro et al. Briefly, the controlled deposition system can include a dispenser that is configured to follow the pattern of the stent structures to deposit a coating directed on the surface of the stent. One exemplary type of dispenser includes an ink-jet printhead type dispenser. Another exemplary type of a dispenser that can be used is a microinjector capable of injecting small volumes ranging from about 2 to about 70 nL, such as NANOLITER™ 2000 available from World Precision Instruments or Pneumatic PICOPUMPS™ PV830 with Micropipette available from Cell Technology System.

Operations such as wiping, centrifugation, blowing, or other web-clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. Any excess coating can also be vacuumed off the surface of the device.

After the application of the primer composition, the solvent in the composition on the stent should be removed before the application of the reservoir layer composition. The solvent can be allowed to evaporate or evaporation can be induced by heating the device at a predetermined temperature for a predetermined period of time. The heating can be conducted in an anhydrous atmosphere and at ambient pressure. The heating can also be conducted under a vacuum condition. In some embodiments, the thermal treatment according to the various embodiments of the invention can be used before or after removal of the solvent or a significant amount of the solvent from the primer layer. A dry or wet coating of the primer layer can therefore be subjected to the thermal treatment temperature for a duration of time that improves the properties of the primer layer.

The composition containing the active agent can be applied to a designated region of the primer coating or the surface of the device. As noted above for the primer layer, the solvent can be removed from the composition by allowing the solvent to evaporate or heating the stent. The thermal treatment according to the various embodiments of the invention can be used before or after removal of the solvent or a significant amount of the solvent from the reservoir layer. A dry or wet coating of the reservoir layer can therefore be subjected to the thermal treatment temperature for a duration of time that improves the properties of the reservoir layer or the underlying primer layer (if a primer layer is included).

The diffusion barrier layer can be formed on a designated region of the active agent-containing coating subsequent to the evaporation of the solvent and the drying of the polymer for the active agent-containing coating. The above-described processes can be similarly repeated for the formation of the diffusion barrier layer. For instance, the thermal treatment according to the various embodiments of the invention can be used before or after removal of the solvent or a significant amount of the solvent from the barrier layer. A dry or wet coating of the barrier layer can therefore be subjected to the thermal treatment temperature for a duration of time that improves the properties of the barrier layer or the underlying layer(s).

Depending on the coating process, residual water and oxygen may remain in the coating after the baking processes used to remove the solvents. For example, after a coating process that occurs in a 60% relative humidity coating environment, a coating with ethylene vinyl alcohol copolymer can have about 2% residual content of water (w/w). These residual components may adversely react with the polymer during the thermal treatment process if they are not removed beforehand. The stents can advantageously be processed to remove essentially all of the water and/or free oxygen that may have been absorbed by the composition during the coating process. The stents, for example; can be placed in a dessicator and then heated in a convection oven to remove any residual water. The stents can also be placed in a vacuum oven or in a gas chamber before undergoing the thermal treatment process. If a gas chamber is used, the chamber can be in communication with a gas source that provides an inert gas such as nitrogen or argon that can remove the water and free oxygen in the coating. The duration required for the process to remove residual water can be determined by a Karl Fisher, or TGA study.

Examples of the Device

Examples of implantable medical devices for the present invention include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE™ and ENDOTAK™, available from Guidant Corporation, Santa Clara, Calif.). The underlying structure of the device can be of virtually any design. In one embodiment, the underlying structure is made from a metallic material or an alloy. The device, for example, can be made of a metallic material or an alloy such as, but not limited to, cobalt chromium alloy (ELGILOY™), stainless steel (316L), high nitrogen stainless steel, e.g., BIODUR 108, cobalt chrome alloy L-605, "MP35N," "MP20N," ELASTINITE™ (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In another embodiment, the underlying structure is made of a biostable polymer, or a bioabsorbable, bioerodable or biodegradable polymer. The underlying structure, for example, can be made of a polymer such as, but not limited to, polyanhydrides such as poly(L-lactic acid), poly(D-lactic acid), poly(D,L-lactic acid), poly(L-lactic acid-co-L-aspartic acid), poly(D,L-lactic acid-co-L-aspartic acid) and poly(maleic acid-co-sebacic acid); poly(amino acid); polyesters such as poly(caprolactone), poly(glycolic acid), poly(hydroxybutyrate), poly(hydroxyvalerate), poly(hydroxybutyrate-valerate), poly(4-hydroxy-L-proline ester), and poly(1,10-decanediol-1,10-decanediol dilactide); polyorthoesters; polycyanoacrylates; and polyphosphazene.

In one embodiment, the device is a bioabsorbable stent which is intended to uphold luminal patency for a duration of time until the stent is partially or completely eliminated by the body. A bioabsorbable stent can include an agent in the body of the stent or can have a coating layer(s) as described herein. A bioabsorbable stent can be subjected to the thermal treatments of the invention.

Method of Use

In accordance with the above-described method, the active agent can be applied to a device, e.g., a stent, retained on the device during delivery and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating layers may then be expanded at the desired area of treatment. A post insertion angiogram may also be utilized to confirm appropriate positioning.

EXAMPLES

The embodiments of the present invention will be illustrated by the following set forth examples.

Example 1

Multi-Link™ stents (available from Guidant Corporation) were cleaned by placement in an ultrasonic bath of isopropyl alcohol solution for 10 minutes. The stents were dried and plasma cleaned in a plasma chamber. An ethylene vinyl alcohol copolymer solution was made. Ethylene vinyl alcohol copolymer (herein, "EVOH") is commonly known by the generic name EVOH or by the trade name EVAL®. The EVOH solution was made with 1 gram of EVOH and 7 grams of DMSO, making an EVOH:DMSO ratio of 1:7. The mixture was placed in a warm water shaker bath at 60° C. for 24 hours. The solution was cooled and vortexed. The cleaned Multi-Link™ stents were dipped in the EVOH solution and then passed over a hot plate, for about 3-5 seconds, with a temperature setting of about 60° C. The coated stents were heated for 6 hours in an air box and then placed in an oven at 60° C., under vacuum condition, and for 24 hours. The coated stents were expanded on a 4.0 mm angioplasty balloon. The coatings remained intact on the stents. The coatings were transparent giving the Multi-Link™ stents a glossy-like shine.

Example 2

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 4 grams of DMSO, making an EVOH:DMSO ratio of 1:4. Dexamethasone was added to the 1:4 EVOH:DMSO solution. Dexamethasone constituted 9% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box and then placed in a vacuum oven at 60° C. for 24 hours. The above-recited step was repeated twice. The average weight of the coating was 0.0003 gram, having an estimated dexamethasone content of 75 μg per stent. The coated stents were expanded on a 4.0 mm angioplasty balloon. The coatings remained intact on the stents. Verification of coverage and physical properties of the coatings were visualized using a scanning electron microscope. The coatings were transparent, giving the Multi-Link™ stents a glossy-like shine.

Example 3

Multi-Link Duet™ stents are cleaned by placement in an ultrasonic bath of isopropyl alcohol solution for 10 minutes. The stents are dried and plasma cleaned in a plasma chamber. The EVOH solution is made with 1 gram of EVOH and 4 grams of DMSO, making an EVOH:DMSO ratio of 1:4. Dexamethasone is added to the 1:4 EVOH:DMSO solution. Dexamethasone constitutes 9% by weight of the total weight of the solution. The solution is vortexed and placed in a tube. The cleaned Multi-Link™ stents are attached to mandrel wires and dipped into the solution. The coated stents are passed over a hot plate, for about 3-5 seconds, with a temperature setting of about 60° C. The coated stents are cured for 6 hours in an air box then placed in a vacuum oven at 60° C. for 24 hours. The single layered dexamethasone/EVOH coated stents are dipped into the 1:4 ratio EVOH:DMSO solution, free from dexamethasone. The stents are passed over the hot plate, cured, and placed in the oven as previously described. The top coating will provide a barrier layer for controlling the release of dexamethasone from the drug coated layer. The coated stents can be expanded on a 4.0 mm angioplasty balloon. It is predicted that the coatings will remain intact on the stents. The coatings will be transparent, giving the Multi-Link™ stents a glossy-like shine.

Example 4

Figure 7:
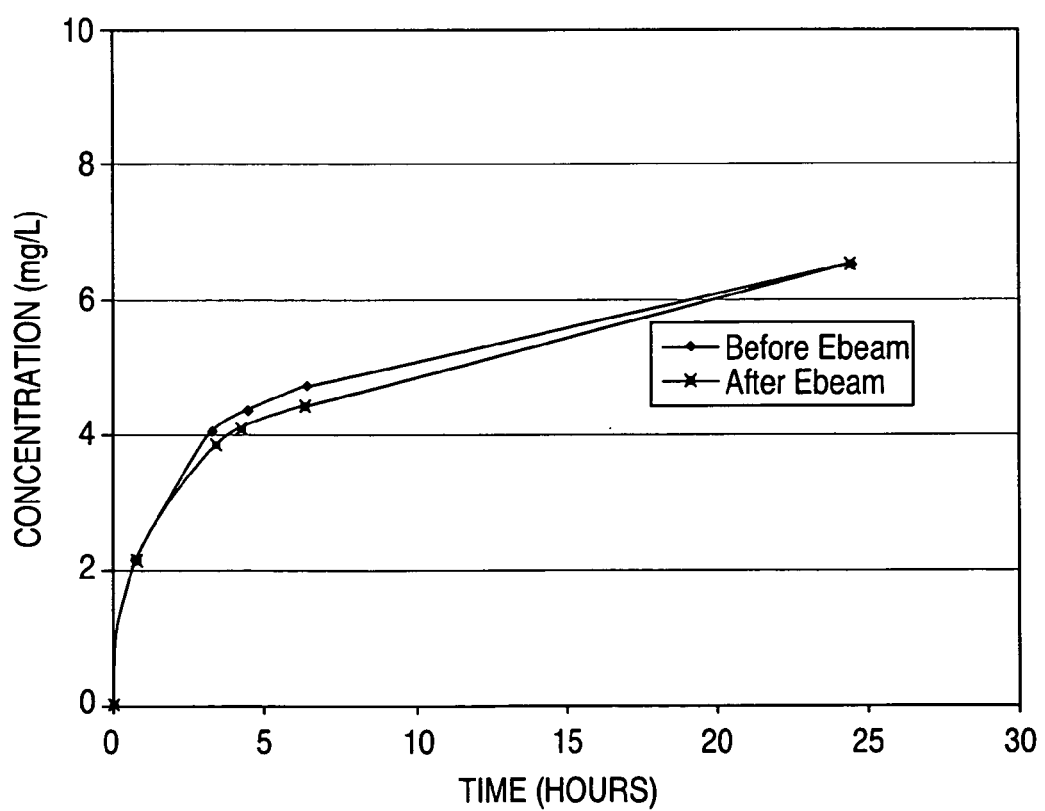
FIG. 7 graphically illustrates elution profiles for stents with a coating of ethylene vinyl alcohol copolymer impregnated with vinblastine made according to Example 4.

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Vinblastine was added to the 1:7 EVOH:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 gram, with an estimated vinblastine concentration of 12 microgram per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 7. The data indicates that electron beam radiation procedure does not interfere in the release of vinblastine from EVOH.

| Release Profile For Vinblastine - Unsterilized | | | |
|---|---|---|---|
| Time (Hours) | microgram Released | Total microgram Released | microgram Release per Hour |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |

-continued

| Release Profile For Vinblastine - Unsterilized | | | |
|---|---|---|---|
| 6 | 0.38 | 4.68 | 0.19 |
| 24 | 1.7 | 6.38 | 0.09 |

| Release Profile For Vinblastine - Sterilized | | | |
|---|---|---|---|
| Time (Hours) | µg Release | Total µg Released | µg Release per Hour |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 5

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Cephalotaxin was added to the 1:7 EVOH:DMSO solution. Cephalotaxin constituted 5% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00013 gram, with an estimated cephalotaxin concentration of 33 µg. The stents were sterilized by electron beam radiation. Cephalotaxin/EVOH coated stents and EVOH-coated control stents were implanted in the coronary arteries of 4 pigs, generally in accordance to the procedure set forth in "Restenosis After Balloon Angioplasty-A Practical Proliferative Model in Porcine Coronary Arteries" by Robert S. Schwartz, et al., Circulation 82(6):2190-2200, December 1990, and "Restenosis and the Proportional Neointimal Response to Coronary Artery Injury: Results in a Porcine Model" by Robert S. Schwartz et al, J Am Coll Cardiol; 19:267-74 February 1992. Results of the porcine artery study indicated that there was no significant difference between the uncoated, EVOH coated and cephalotaxin coated stents in the amount of neointimal proliferation resulting from arterial injury.

Example 6

Multi-Link Duet™ stents (available from Guidant Corporation) were cleaned by placement in an ultrasonic bath of isopropyl alcohol solution for 20 minutes, then air dried. An EVOH stock solution was made with 1 gram of EVOH and 7 grams of DMSO, making an EVOH:DMSO ratio of 1:7. The mixture was placed in a warm water shaker bath at 60° C. for 12 hours. The solution was mixed, then cooled to room temperature. A co-solvent was added to the EVOH solution to promote wetting of the struts of the Multi-Link Duet™ stents. One gram of tetrahydrofuran (THF) was mixed with 1.2 grams of the EVOH:DMSO solution. The cleaned Multi-Link Duet™ stents were attached to mandrel wires and dipped into the solution. The coated stents were passed over a hot plate, for about 3 to 5 seconds, with a temperature setting of about 60° C. The coated stents were then heated in a laboratory oven at 90° C. for 4 hours. The thin EVOH coating adhered to stainless steel without peeling or cracking. EVOH forms a superior primer base coat for other polymers that do not adhere well to stainless steel.

Example 7

Multi-Link Duet™ stents were cleaned in an ultrasonic bath of isopropyl alcohol for 20 minutes, then air dried. An EVOH solution was made with 1 gram of EVOH and 5 grams of DMSO, making an EVOH:DMSO ratio of 1:5. The mixture was placed in a warm water shaker bath at 60° C. for 12 hours. The solution was mixed, then cooled to room temperature. The dissolved EVOH:DMSO solution was mixed with 24.6 grams of THF and 19.56 grams of DMSO. The solution was mixed then placed in the reservoir of an air pressured atomizing sprayer. Multi-Link Duet™ stents were sprayed while the stents rotated between 30 to 120 rpm. The spray time was dependent upon the flow rate of the sprayer. A flow rate between 1 to 20 mg/second required a stent to be sprayed between 1 to 30 seconds. The polymer coated Multi-Link Duet™ stents were heated in a forced air convection oven for 12 hours. The coatings were transparent, giving the Multi-Link Duet™ stents a glossy-like shine.

Example 8

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. Various co-solvents were examined to determine which co-solvent would promote a thicker coating. These co-solvents were THF, DMF, 1-butanol, and n-butyl acetate. The formulation for the co-solvents was as follows. Three grams of dissolved EVOH:DMSO solution was mixed with 0.9 gram of THF; three grams of dissolved EVOH:DMSO solution was mixed with 0.39 gram of DMF; three grams of dissolved EVOH:DMSO solution was mixed with 0.5 gram of 1-butanol; and three grams of dissolved EVOH:DMSO solution was mixed with 0.68 gram of n-butyl acetate. The cleaned Multi-Link Duet™ stents, attached to mandrel wires, were dipped into the solutions. The coated stents were passed over a hot plate, for about 3 to 5 seconds, with a temperature setting of about 60° C. The coated stents were heated in a forced air convection oven for 24 hours. A second layer of coating was applied to coated Multi-Link Duet™ stents and the stents were heated in the same manner as above. No difference was seen between the stents coated with the various co-solvents (e.g., greater weight of coating or physical appearance). All coated stents were transparent, giving the Multi-Link Duet™ stents a glossy-like shine. No webbing or bridging of the coating was seen between the struts of the coated Multi-Link Duet™ stents. The weight of the coatings was between 0.2 to 0.27 mg/stent.

Example 9

Multi-Link Duet™ stents are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight dexamethasone solution is formulated as follows: 2.96 grams of the EVOH:DMSO solution is mixed with 0.29 gram of dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 10

Multi-Link Duet™ stents are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight dexamethasone solution is formulated as follows: 2.96 grams of the EVOH:DMSO solution is mixed with 0.29 gram of dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 11

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 4.75% by weight actinomycin D solution was formulated as follows: 600 milligrams of the EVOH:DMSO solution was mixed with 40 milligrams of actinomycin D, then 200 milligrams of THF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 12

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.60% by weight actinomycin D solution was formulated as follows: 600 milligrams of the EVOH:DMSO solution was mixed with 40 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 13

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.45% by weight actinomycin D solution was formulated as follows: 680 milligrams of the EVOH:DMSO solution was mixed with 80 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 14

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH:DMSO solution is mixed with 40 milligrams of actinomycin D, then 2000 milligrams of THF is added. The cleaned Multi-Link Duet™ stents can be sprayed upon by the above formulation. The coated stents are cured in a forced air convection oven for 2 hours. A second layer of coating is applied and cured in the above manner.

Example 15

Inhibition of SMC Proliferation with Actinomycin D

Figure 8:
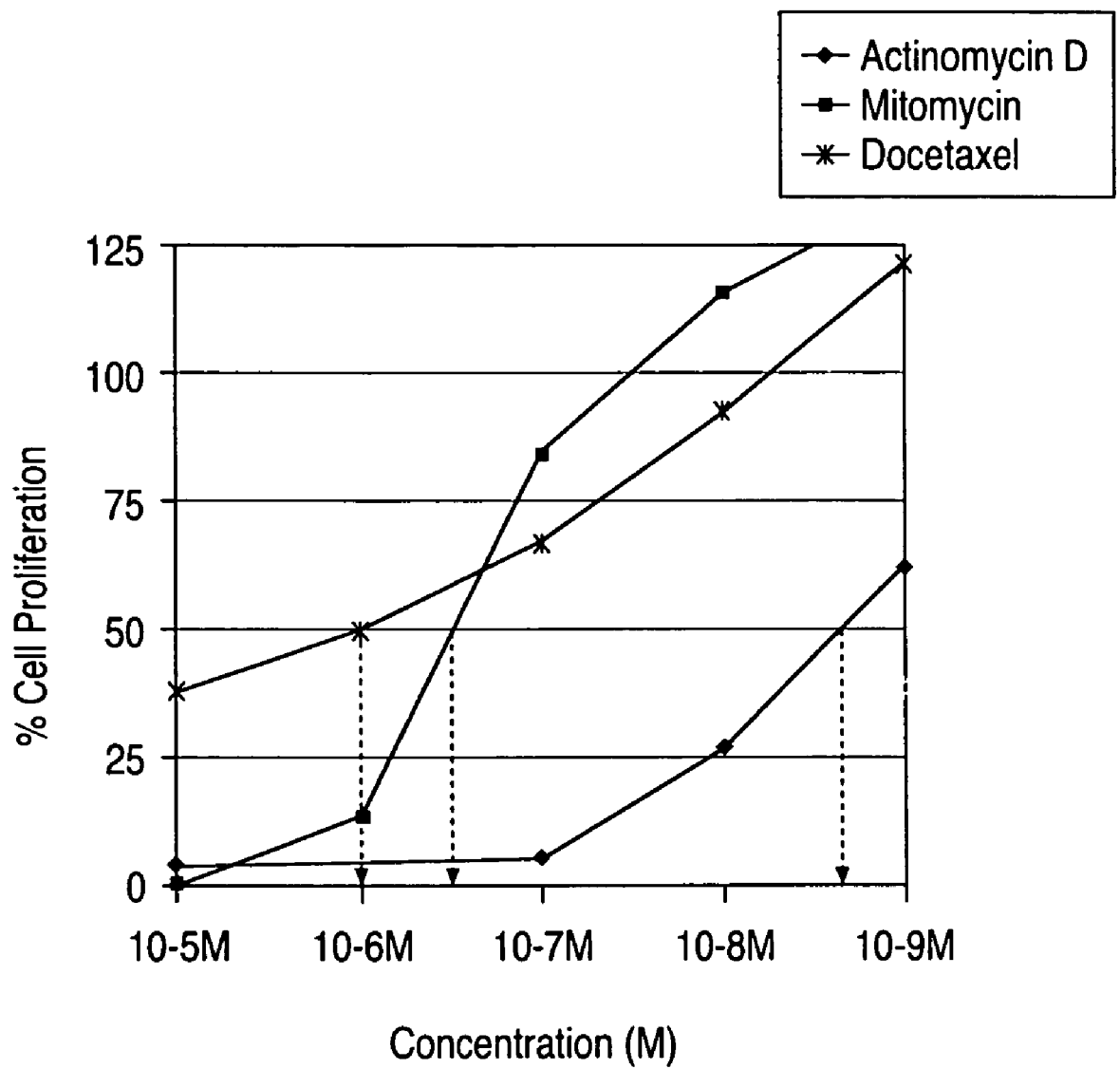
FIG. 8 graphically illustrates in vitro experimental data, in accordance with Example 15, showing affects of actinomycin D, mitomycin, and docetaxel on smooth muscle cell proliferation.

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3-4. SMC monolayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 8.

The $IC_{50}$ (concentration at which 50% of the cells stop proliferating) of actimomycin D was $10^{-9}$M as compared to $5 \times 10^{-5}$M for mitomycin and $10^{-6}$M for docetaxel. Actinomycin D was the most potent agent to prevent SMC proliferation as compared to other pharmaceutical agents.

Example 16

Reduction in Restenosis in the Porcine Coronary Artery Model

Porcine coronary models were used to assess the degree of the inhibition of neointimal formation in the coronary arteries of a porcine stent injury model by actinomycin D, delivered with a microporous balloon catheter ($1 \times 10^6$ pores/mm with sizes ranging from 0.2-0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. The drug was delivered to the denuded sites at 3.5 atm (3.61 Kg/sq cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100(IEL\ area - lumen\ area)/IEL\ area$$

where IEL is the internal elastic lamia.

The control group of animals received delivery of water instead of the drug. The test group of animals received actinomycin D in two different concentration of $10^{-5}$M and $10^{-4}$M. The results of the study are tabulated in Table 6. The percent stenosis in the treated groups (32.3+/−11.7) was significantly decreased as compared to the control groups (48.8+/−9.8). FIGS. 9A and 9B illustrate sample pictures of the histology slides of the coronary vessels from the control and the Dose 1 group, respectively.

TABLE 6

| | CONTROL 0 M | DOSE 1 1E-05 M | DOSE 2 1E-04 M | t test (significant if p < 0.05) | |
|---|---|---|---|---|---|
| | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |
| | CONTROL 0 M | DOSE 1 1E-05 M | DOSE 2 1E-04 M | t test (significant if p < 0.05) | |
| | (n = 27) | (n = 30) | (n = 21) | p~ | p* |
| HISTOMORPHOMETRIC DATA | | | | | |
| Percent Stenosis (IEL area-lumen area)/IEL area | 63.4 +/− 12.7 | 51.8 +/− 13.8 | 54.1 +/− 11.7 | 0.002 | 0.01 |
| Residual Lumen (Lumen area)/IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

Example 17

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved.

Example 18

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVOH:DMSO solution was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved.

Example 19

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

Example 20

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH:DMSO solution is mixed with 40 milligrams of actinomycin D, then 2000 milligrams of THF is added. The cleaned Multi-Link Duet™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

Example 21

A stainless steel stent can be spray coated with a formulation of EVOH and a drug, as previously described in any of the above examples. A diffusion barrier composition can be formulated with 2 grams of EVOH blended with 20 grams of dimethylsulfoxide. 2.2 grams of fumed silica can be added and dispersed with a high shear process. With constant agitation, 50 grams of tetrahydrofuran and 30 grams of dimethylformamide are admixed with the blend. The stent, having the EVOH coating, can be immersed in the diffusion barrier composition to form a layer.

Example 22

A stainless steel stent can be spray coated with a formulation of EVOH and a drug, as previously described in any of the above examples. A diffusion barrier formulation can be made by dissolving 8 grams of EVOH into 32 grams of dimethylsulfoxide. To this is added 14 grams of rutile titanium dioxide and 7 grams more of dimethylsulfoxide. The particles can be dispersed using a ball mill. The final solution is diluted with 39 grams of tetrahydrofuran, added slowly with constant agitation. It is predicted that the diffusion barrier will reduce the rate at which the drug is released from the stent.

Example 23

A stainless steel stent can be coated with a formulation of EVOH and a drug, as previously described in any of the above examples. A diffusion barrier formulation can be made by dissolving 8 grams of EVOH in 32 grams of dimethylsulfoxide. 10.5 grams of solution precipitated hydroxyapatite can be added to the blend. The particles can be dispersed using a rotor stator mixer. With constant agitation, 30 grams of tetrahydrofuran can be added. The stent can be coated by immersion followed by centrifugation.

Example 24

A stent can be coated with a formulation of EVOH and a drug, as previously described in any of the above examples. 8 grams of EVOH can be added 50 grams of dimethylsulfoxide and the polymer can be dissolved by agitation and heat. Four grams of lamp black can be added and dispersed in a ball mill. 60 grams of dimethyl sulfoxide and 110 grams of tetrahydrofuran are slowly added while stirring. The stent can be spray coated.

Example 25

A stent can be coated with a formulation of EVOH and a drug, as previously described in any of the above examples. Colloidal gold can be prepared by reduction of tetrachloroauric acid with sodium citrate in aqueous solution. The solution can be exchanged by rinsing with tetrahydrofuran. Eight grams of EVOH can be dissolved in 32 grams of dimethylsulfoxide. To this is added a solution of 77 grams of colloidal gold in 32 grams of tetrahydrofuran. The stent can be coated by a dip coating process.

Example 26

In vivo data is provided illustrated positive remodeling caused by the application of actinomycin D. Stents coated with EVOH impregnated with actinomycin D and a control group of stents coated with EVOH free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

| Condition | Mean Area | Std Dev |
|---|---|---|
| IEL | | |
| Drug coated (Act-D in EVOH) | 7.47 | 0.89 |
| Control (EVOH) | 6.6 | 0.61 |
| p value | 0.0002 | Statistical significant difference |
| EEL (external elastic lamia) | | |
| Drug coated (Act-D in EVOH) | 8.54 | 0.87 |
| Control (EVOH) | 7.94 | 0.73 |
| p value | 0.014 | Statistical significant difference |

EEL Area (mm$^2$)

| ID # | Control | ID # | Actinomycin D | ID # | EVOH |
|---|---|---|---|---|---|
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9926 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |
| 59 LCA d | 8.3054 | 68 LAD d | 8.7854 | 65 LCX d | 6.4638 |
| 59 LCX d | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 8.7630 |
| | | | | 70 LAD p | 8.2222 |
| AVG | 7.8402 | | 8.5425 | | 7.9475 |
| SD | 0.8046 | | 0.8755 | | 0.7349 |

| ActD vs EVOH | |
|---|---|
| p = | 0.014709 |
| AVG % EEL growth | 7.486304 |

IEL Area (mm2)

| ID # | Control | ID # | Actinomycin D | ID # | EVOH |
|---|---|---|---|---|---|
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |

-continued

| EEL Area (mm²) |  |  |  |  |  |
|---|---|---|---|---|---|
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
|  |  |  |  | 70 LAD p | 6.9032 |
| AVG | 6.6489 |  | 7.4727 |  | 6.6025 |
| SD | 0.7883 |  | 0.8972 |  | 0.6130 |

| ActD vs EVOH | |
|---|---|
| p = | 0.000283 |
| AVG % IEL growth | 13.17981 |

Figure 10B:
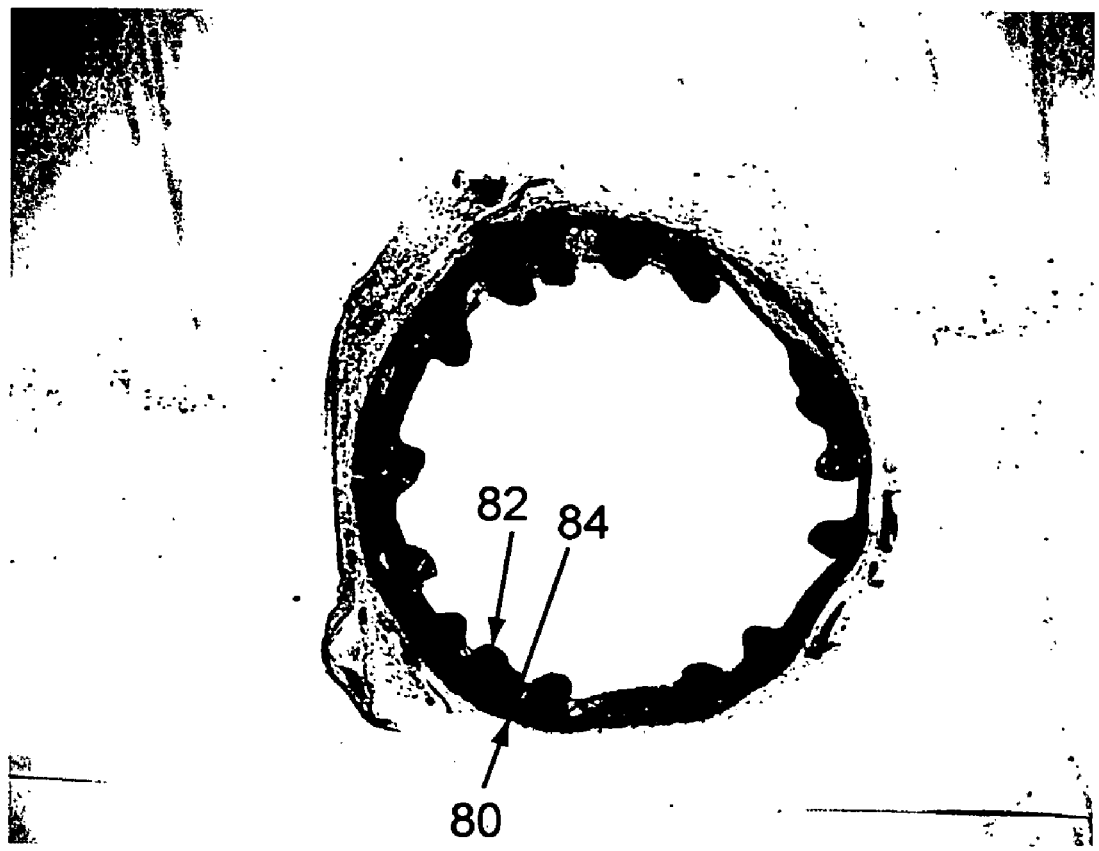
FIG. 10B is a picture of a histology slide of a coronary vessel from the actinomycin D group in accordance with Example 26.

FIGS. 10A and 10B illustrate sample pictures of the histology slides of the coronary vessels from the control group 64 RCA (Right Coronary Group) and the actinomycin D loaded stent group 68 LAD (Left Anterior Descending), respectively. The stent used was an Advanced Cardiovascular Systems Multi-Link Duet™ (stainless steel). As is illustrated by FIG. 10B, the positive remodeling of EEL 80, caused by the application of actinomycin D, creates a gap between stent struts 82 and EEL 80. Thrombus deposits, illustrated by reference number 84, are formed in the gap over time. The use of a self-expandable stent eliminates the formation of the gap as the stent self-expands in response to the positive remodeling of IEL. Thrombus deposits can be, accordingly, eliminated.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced.

Example 27

2 grams of an acrylate terminated urethane (Henkel 12892) can be added to 18 grams of ethyl acetate with 0.08 grams of benzophenone and 0.08 grams of 1-hydroxycyclohexyl phenyl ketone. After application, the stent can be cured for 5 minutes under medium pressure mercury lamp.

Example 28

For a thermoset system, 1.67 grams of Epon 828 (Shell) resin can be added to 98 grams of propylene glycol monomethyl ether and 0.33 grams of Jeffamine T-430 (Huntsman). After application, the stent can be baked for 2 hours at 80° C. and 2 hours at 160° C.

Example 29

A 0.25% (w/w) solution of tetra-n-butyl titanate can be made in anhydrous ethyl acetate. The solution can be applied by spraying to a surface of a stainless steel stent. The stent can be heated at 100° C. for two hours.

Example 30

Objective

Coated stents tested through simulated delivery to a target lesion for testing the mechanical integrity of the coating.

| Group | Quantity | Coating |
|---|---|---|
| A | 2 | Control: 2% EVOH in 1:1 THF:DMSO, 3:1 EVOH: Act-d; no primer |
| B | 2 | 2% EVOH in 5:3:2 THF:DMF:DMSO, 3:1 EVOH: Act-d; no primer |
| C | 2 | EVOH primer layer baked at 120 C./60 C. for 2/10 hrs + 2% EVOH in 1:1 THF:DMSO, 3:1 EVOH: Act-d; primer |
| D | 2 | EVOH primer layer baked at 140 C./60 C. for 2/2 hrs + 2% EVOH in 1:1 THF:DMSO, 3:1 EVOH: Act-d; primer |

Background

In this experiment four different treatment groups were tested through a simulated delivery and use. Number of peel defects at rings 3, 5, and 7, with a peel defect defined as a location on the stent where coating has been removed to expose bare stent or an underlying layer of coating, were observed.

Materials and Equipment
1. 8, 13 mm Solo stents (Available from Guidant Corporation);
2. 8, 3.0×30 mm Duet catheters;
3. 100% IPA;
4. Tominator Stent Crimper S/N 400;
5. 7F JL4 guiding catheter;
6. 0.014" Balance Middle Weight guide wire;
7. Rotating Hemostatic Valve;
8. SVS tortuosity tree (2.5 mm lumen tapering to 1.5 mm lumen).

Preparation
Crimped the stents onto the catheters using the Tominator crimper and the following conditions: 3 crimps, 65 psi, rotation between crimps.

Test Procedure
1. Performed simulation using heart model having a tortuosity and contained in a tub filled with water:

a. Inserted the stents through the following set-up: RHF, 7F JL4 guiding catheter, SVS tortuosity tree (2.5 mm lumen at entrance, 1.5 mm lumen at exit).
b. Once the stent passed through the distal opening of tortuosity, the balloon was cut from the catheter just distal to proximal marker.

2. Examined the stents under 100× magnification using Leica MZFLIII microscope in the clean environment room (CER).
3. Recorded number of peel defects at stent rings 3, 5, and 7. Only the OD was examined for peel defects.
4. All test samples were handled with personal protective equipment (PPE) appropriate for drug containing stents.

| Data Summary and Results | | |
|---|---|---|
| Group | # Peel Defects/Ring | Comments |
| A (THF) | 2.0 | — |
| B (DMF) | 5.3 | Began with poor coating finish. |
| C (140° C.) | 0.7 | — |
| D (120° C.) | 0 | — |

Discussion

The test was performed to observe the coating integrity after a simulated delivery to a tortuosity without a lesion. The primer layer improved coating adhesion to the stents that resulted in fewer defects after a simulated use. Group B had a number defects. Although the coating surface for Group B was poor to begin with, and the defects were not too severe.

Example 31

Objective

The adhesion of 0.67% actinomycin-D (in 5% EVAL 1:1 THF:DMSO solution) coating on stents with two different surface treatments was compared to control samples. The specific surface treatments consisted of: (1) argon plasma treatment; and (2) argon plasma treatment with a primer layer of 5% EVOH in 1:1 DMSO:DMF solution applied with the dip-spin process, i.e., centrifugation process, and followed by heat treatments at 120° C. for two hours and 60° C. for 10 hours. The test method used to test adhesion of coatings on stents was a wet flow test, expanding the stents in a TECOFLEX™ tubing at 37° C. of water or saline. Water or saline is then flushed through the stents for 18 hours to simulate blood flow through the stents. The stents were then removed from the TECOFLEX™ with a "stent catcher" and observed under optical microscope for defects.

| Group | Treatment | Flow Rate |
|---|---|---|
| A | None | 50 mL/min |
| B | Argon plasma | 50 mL/min |
| C | Argon plasma + 5% EVOH in 1:1 DMSO:DMF heated at 120° C. for two hours and 60° C. for 10 hours | 50 mL/min |
| D | None | 100 mL/min |
| E | Argon plasma | 100 mL/min |
| F | Argon plasma + 5% EVOH in 1:1 DMSO:DMF heated at 120° C. for two hours and 60° C. for 10 hours | 100 mL/min |

Materials and Equipment
1. 30, 13 mm coated Solo stents, cleaned ultrasonically in IPA for 15 minutes;
2. 30, balloon catheters or subassemblies to expand the stents (3.0×20 mm RX Rocket);
3. 0.67% Actinomycin-D in 5% EVOH with 1:1 THF:DMSO solution;
4. 5% EVOH in 1:1 DMF:DMSO;
5. 3.0 mm, thin walled TECOFLEX™ tubing;
6. Saline;
7. Lint Free Wipes SU 00126 or equivalent;
8. 100% IPA;
9. Oven;
10. Timer;
11. Centrifuge;
12. Plasma Machine (available from Advanced Plasma System);
13. Ultrasonic cleaner;
14. Mettler balance with 0.1 micrograms resolution; and
15. Spray Coater with Fan Air Cap and EFD dispenser (EFD Inc. East Providence R.I.).

Preparation
1. Sonicated the stents in IPA for 15 minutes;
2. Weighed each stent to the nearest microgram;
3. Prepared 5 stent samples:
   A. Groups A and D:
      i. Performed spray-coating process in CER under the following conditions: 3 passes, 3-second spray, no blowing.
      ii. Weighed each sample at the end of the last pass to the nearest microgram.
      iii. Baked the samples for 4 hrs at 60° C.
      iv. Placed the stents into the TECOFLEX™ tubing with a balloon catheter—submerged in 37° C. saline.
   B. Groups B and E:
      i. Placed the samples on a sample holder. Performed argon plasma treatment using plasma machine.
      ii. Performed spray-coating process in CER under the following conditions: 3 passes, 3-second spray, no blow.
      iii. Weighed each sample at the end of the last pass to the nearest microgram.
      iv. Baked the samples for 4 hrs at 60° C.
      v. Placed the stents into the TECOFLEX™ tubing with the balloon catheter—submerged in 37° C. saline.
   C. Groups C and F:
      i. Placed samples flat on a sample holder. Performed argon plasma treatment.
      ii. Used dip-spin process to apply 2% EVOH primer layer, 1:1 DMSO:DMF.
      iii. Baked the stents at 120° C. for two hours.
      iv. Baked the stents at 60° C. for ten hours.
      v. Performed spray-coating process in CER under the following conditions: 3 passes, 3-second spray, no blow.
      vi. Weighed each sample at the end of the last pass to the nearest microgram.
      vii. Baked the samples for 4 hrs at 60° C.
      viii. Placed the stents into the TECOFLEX™ tubing with a balloon catheter—submerged in 37° C. water.

Test Procedure
Tested three samples from each group. Wet Flow Testing:
1. Expanded the stents into the 3.0 mm TECOFLEX™ tubing in 37° C. saline.
2. Performed wet flow testing for 18 hrs.

3. Removed the stents from the TECOFLEX™ tubing with a stent catcher.

4. Count defects, based on the following categories: Defect type; defect size; defect location; and peel defects on rings 3, 5, and 7.

5. Stent weight could not be a measurable because of the loss of the drug and uptake of water.

6. All test samples were handled with PPE appropriate for drug containing stents.

Data Summary

| Group | Average # of Peel Defects/Stent (3 rings) After Flow Test | Average # Peel Defects/Ring After Flow Test |
| --- | --- | --- |
| A | 18.0 | 6.0 |
| B | 15.3 | 5.1 |
| C | 2.7 | 0.9 |
| D | 14.3 | 4.8 |
| E | 14.0 | 4.7 |
| F | 0.7 | 0.2 |

Discussion

Peel defects are defined as areas where the coating separated from the stent. The number of peel defects were counted on the stents' OD/sidewall on rings 3, 5, and 7. The flow field was on the ID of the stents' surface. Some of the damage to the OD surface could have been aggravated by the TECOFLEX™ tubing. The number of peel defects observed on groups C and F (EVOH primer) was clearly lower than the other two test groups, regardless of flow rate. The increased flow rate did not induce more peel defects.

Example 32

Objective

The objective of this experiment was to test the adhesive properties of an actinomycin-D containing coating on stainless steel stents having an EVOH primer layer. The coated stents were tested in a wet flow test condition of saline heated to 37° C. The number of "peel defects" on a select number of stent rings was observed. A "peel defect" is defined as a location on the stent surface devoid of coating, i.e., bare metal or underlying coating layer that is visible under optical magnification of less than 100×.

| Group | Treatment | Flow Rate |
| --- | --- | --- |
| A | Argon plasma treatment + EVOH primer layer (15% EVOH, 1:1 DMF: DMSO) baked at 140° C. for 2 hours and dried at 60° C. for 2 hours | 50 mL/min |
| B | Argon plasma treatment + EVOH primer layer (15% EVOH, 1:1 DMF: DMSO) baked at 120° C. for 2 hours and dried at 60° C. for 10 hours | 50 mL/min |

Materials and Equipment 1. 10, 13 mm Solo stents, cleaned ultrasonically in IPA for 15 minutes;
2. 10, balloon catheters or subassemblies to expand the stents;
3. 15% EVOH in 1:1 DMF:DMSO solution;
4. Actinomycin-D solution, 1:1 THF:DMSO with 3:1 EVOH: Act-D;
5. TECOFLEX™ tubing
6. Saline
7. Lint Free Wipes SU 00126 or equivalent
8. 100% IPA
9. Oven
10. Timer
11. Plasma Machine (Advanced Plasma System);
12. Ultrasonic cleaner; and
13. Mettler balance with 0.1 micrograms resolution.

Preparation

1. Sonicated the stents in IPA for 15 minutes.
2. Weighed each stent to the nearest microgram.
3. Prepared 5 stent samples for each group:
   A. Group A:
      i. Placed the samples flat on a sample holder. Performed argon plasma treatment.
      ii. Used dip-spin process, i.e., centrifugation at 6000 rpm for one minute, to apply the EVOH primer layer, 1:1 DMSO:DMF.
      iii. Baked the stents at 140° C. for two hours in the convection oven.
      iv. Took weight measurements of each stent to the nearest microgram.
      v. Baked the stents at 60° C. for two hours in vacuum oven.
      vi. Took weight measurements of each stent to the nearest microgram.
      vii. Performed spray-coating process in CER under the following conditions: 3 passes, 3-second spray, no blow.
      viii. Weighed each sample at the end of the last pass to the nearest microgram.
      ix. Baked samples for 4 hrs at 60° C.
      x. Took weight measurements of each stent to the nearest microgram.
      xi. Placed the stents into the TECOFLEX™ tubing with a balloon catheter—submerged in 37° C. water.
   B. Groups B:
      i. Placed samples flat on sample holder. Performed argon plasma treatment.
      ii. Used dip-spin process at 6000 rpm for one minute to apply EVOH primer layer, 1:1 DMSO:DMF.
      iii. Baked the stents at 120° C. for two hours in the convection oven.
      iv. Took weight measurements on each stent to the nearest microgram.
      v. Baked the stents at 60° C. for ten hours in vacuum oven.
      vi. Took weight measurements for each stent to the nearest microgram.
      vii. Performed spray-coating process in CER at the following conditions: 3 passes, 3-second spray, no blow.
      viii. Weighed each sample at the end of the last pass to the nearest microgram.
      ix. Baked the samples for 4 hrs at 60° C.
      x. Took weight measurements of each stent to the nearest microgram.
      xi. Placed the stents into the TECOFLEX™ tubing with a balloon catheter—submerged in 37° C. water.

Test Procedure

1. Performed wet flow testing overnight for about 18 hrs.
2. Removed the stents from the TECOFLEX™ tubing with a stent catcher.

3. Counted the defects based on the number of peel defects at rings 3, 5, and 7 on the stents' OD. Count the defects on the ID of the same rings.

4. The weight could not be measured because of the loss of the drug and uptake of water.

5. All test samples were handled with PPE appropriate for drug containing stents.

Data Summary and Results

| Group | # Peel Defects (OD) | Average # of Peel Defects/Ring (OD, rings 3, 5, 7) | # Peel Defects (ID) | Average # of Peel Defects/Ring (ID, rings 3, 5, 7) |
|---|---|---|---|---|
| A | 0 | 0 | 1 | 0.3 |
|   | 0 | 0 | 1 | 0.3 |
|   | 0 | 0 | 1* | 0.3 |
| B | 0 | 0 | 0 | 0 |
|   | 0 | 0 | 0 | 0 |
|   | 0 | 0 | 0 | 0 |

*Defect occurred at a location of a defect in the stent surface.

Example 33

Objective

The objective of this study was to test the adhesive properties of an actinomycin-D containing coating on stainless steel stents having an EVOH primer layer. The coated stents were tested under wet flow conditions of saline heated to 37° C. The number of "peel defects" on a select number of stent rings was observed. A "peel defect" is defined as a location on the stent surface devoid of coating, i.e., bare metal or an underlying coating layer that is visible under optical magnification of no more than 100×.

| Group | Treatment | Flow Rate |
|---|---|---|
| A Control | None | 50 mL/min |
| B | Argon plasma treatment + EVOH primer layer by dip-spin (2% EVOH, 1:1 DMF:DMSO) baked at 140° C. for 4 hours | 50 mL/min |
| C | EVOH primer layer by dip-spin (2% EVOH, 1:1 DMF:DMSO) baked at 140° C. for 4 hours | 50 mL/min |
| D | Argon plasma treatment + EVOH primer layer by spray (2% EVOH, 1:1 DMF:DMSO) baked at 140° C. for 4 hours | 50 mL/min |
| E | EVOH primer layer by spray (2% EVOH, 1:1 DMF:DMSO) baked at 140° C. for 4 hours | 50 mL/min |

Materials and Equipment 1. 25, 13 mm Solo stents, cleaned ultrasonically in IPA for 15 minutes;
2. 25, balloon catheters or subassemblies to expand the stents;
3. 2% EVOH in 1:1 DMF:DMSO solution;
4. Actinomycin-D solution, 1:1 THF:DMSO with 3:1 EVOH: Act-D;
5. 3.0 mm TECOFLEX™ tubing;
6. Saline;
7. Lint Free Wipes SU 00126 or equivalent;
8. 100% IPA;
9. Convection Oven
10. Timer;
11. Plasma Machine;
12. Ultrasonic cleaner; and
13. Mettler balance with 0.1 micrograms resolution.

Preparation

1. Sonicated the stents in IPA for 15 minutes.
2. Weighed each stent to the nearest microgram.
3. Prepared 5 stent samples for each group.
  A. Group A (Control):
    i. Performed spray-coating process in CER under the following conditions: 3 passes, 3-second spray, no blow.
    ii. Weighed each sample at the end of the last pass to the nearest microgram.
    iii. Baked the samples for 4 hrs at 60° C.
    iv. Took the weight measurements of each stent to the nearest microgram.
    v. Placed the stents into the TECOFLEX™ tubing with the balloon catheter—submerged in 37° C. water.
  B. Group B:
    i. Placed samples flat on sample holder. Performed argon plasma treatment.
    ii. Used dip-spin process to apply EVOH primer layer, 1:1 DMSO: DMF (6000 rpm for one minute).
    iii. Baked the stents at 140° C. for 4 hours in convection oven.
    iv. Took weight measurements on each stent to the nearest microgram.
    v. Performed spray-coating process in CER at the following conditions: 3 passes, 3-second spray, no blow.
    vi. Weighed each sample at the end of the last pass to the nearest microgram.
    vii. Baked the samples for 4 hrs at 60° C.
    viii. Took the weight measurements of each stent to the nearest microgram.
    ix. Placed the stents into the TECOFLEX™ tubing with a balloon catheter—submerged in 37° C. water.
  C. Group C:
    i. Used dip-spin process to apply EVOH primer layer, 1:1 DMSO:DMF (6000 rpm for one minute).
    ii. Baked the stents at 140° C. for four hours in convection oven.
    iii. Took weight measurements on each stent to the nearest microgram.
    iv. Performed spray-coating process in CER under the following conditions: 3 passes, 3-second spray, no blow.
    v. Weighed each sample at the end of the last pass to the nearest microgram.
    vi. Baked the samples for 4 hrs at 60° C.
    vii. Took weight measurements of each stent to the nearest microgram.
    viii. Placed stents into the TECOFLEX™ tubing with a balloon catheter—submerged in 37° C. water.
  D. Group D:
    i. Placed the samples flat on a sample holder. Perform argon plasma treatment.
    ii. Spray coated primer layer (2% EVOH, 1:1 DMF: DMSO) onto the stents. Used 1.5 sec. spray time, 1-2 passes to achieve 10-40 micrograms of coating.
    iii. Baked the stents at 140° C. for 4 hours in the convection oven.
    iv. Took weight measurements on each stent to the nearest microgram.
    v. Performed spray-coating process in CER at the following conditions: 3 passes, 3-second spray, no blow.

vi. Weighed each sample at the end of the last pass to the nearest microgram.
vii. Baked samples for 4 hrs at 60° C.
viii. Took weight measurements of each stent to the nearest microgram.
ix. Placed stents into the TECOFLEX™ tubing with a balloon catheter—submerged in 37° C. water.

E. Group E:
i. Spray coated primer layer (2% EVOH, 1:1 DMF:DMSO) onto the stents. Used 1.5 sec. spray time, 1-2 passes to achieve 10-40 micrograms of coating.
ii. Baked the stents at 140° C. for four hours in convection oven.
iii. Took weight measurements on each stent to the nearest microgram.
iv. Performed spray-coating process in CER at the following conditions: 3 passes, 3-second spray, no blow.
v. Weighed each sample at the end of the last pass to the nearest microgram.
vi. Baked the samples for 4 hrs at 60° C.
vii. Took weight measurements of each stent to the nearest microgram.
viii. Placed the stents into the TECOFLEX™ tubing with a balloon catheter—submerged in 37° C. water.

Test Procedure
1. Performed wet flow testing overnight for about 18 hrs.
2. Removed stents from the TECOFLEX™ tubing with a stent catcher.
3. Counted the defects based on the number of peel defects at rings 1, 3, 5, and 7 on the stents' OD. Count the defects on the ID of the same rings.
4. Stent weight could not be a measurable because of the loss of the drug and uptake of water.
5. All test samples were handled with PPE appropriate for drug containing stents.

| Data Summary and Results | | |
|---|---|---|
| Group | Defects/Ring (OD) | Defects/Ring (ID) |
| Control | 2.67 | 3.00 |
| Dip/Plasma | 0.67 | 0.47 |
| Dip/No Plasma | 0.87 | 0.80 |
| Spray/Plasma | 0.47 | 0.80 |
| Spray/No Plasma | 0.67 | 0.73 |

Discussion

Peel Defects of Primer Coated Stents vs. Untreated Controls

An improved adhesion, based on the number of peel defects, of the drug containing coating to the Tri-Star stent when an EVOH primer layer was applied is illustrated. All four treatment groups displayed significantly fewer peel defects per stent than the untreated control stents. Use of a spray-coated, 2% EVOH solution in 1:1 DMF:DMSO as a primer significantly improved adhesion of actinomycin-D containing coating to the Tri-Star stents vs. the controls. The spray-coated primer produced slightly higher peel defect counts compared to the dip-spin deposited primer.

Example 34

Objective

The objective of this experiment was to test the adhesive properties of an Actinomycin-D containing coating to stainless steel stents having an EVOH primer layer. More specifically, this experiment attempted to illustrate the effect of different bake times on the final result. The coated stents were tested under wet flow conditions of saline heated to 37° C. The number of "peel defects" on a select number of stent rings was observed.

| Group | Treatment | Flow Rate |
|---|---|---|
| A Control | none | 50 mL/min |
| B | Argon plasma treatment + EVOH primer layer by spray (2% EVOH, 1:1 DMF:DMSO) baked at 140° C. for 15 minutes | 50 mL/min |
| C | Argon plasma treatment + EVOH primer layer by spray (2% EVOH, 1:1 DMF:DMSO) baked at 140° C. for 30 minutes | 50 mL/min |
| D | Argon plasma treatment + EVOH primer layer by spray (2% EVOH, 1:1 DMF:DMSO) baked at 140° C. for 60 minutes | 50 mL/min |
| E | Argon plasma treatment + EVOH primer layer by spray (2% EVOH, 1:1 DMF:DMSO) baked at 140° C. for 120 minutes | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVOH in 1:1 DMF:DMSO solution;
4. Actinomycin-D solution, 1:1 THF:DMSO with 3:1 EVOH: Act-D;
5. 3.0 mm TECOFLEX™ tubing;
6. Saline;
7. Lint Free Wipes SU 00126 or equivalent;
8. 100% IPA;
9. Convection Oven;
10. Timer;
11. Plasma Machine;
12. Ultrasonic cleaner; and
13. Mettler balance with 0.1 micrograms resolution.

Preparation
1. Sonicated stents in IPA for 15 minutes.
2. Weighed each stent to the nearest microgram.
3. Prepared 5 stent samples for each group.
A. Group A (Control):
i. Performed spray-coating process in CER under the following conditions: 3 passes, 3-second spray, no blow.
ii. Weighed each sample at the end of the last pass to the nearest microgram.
iii. Baked the samples for 240 minutes at 50° C.
iv. Took weight measurements of each stent to the nearest microgram.
v. Placed the stents into the TECOFLEX™ tubing with a balloon catheter—submerged in 37° C. water.
B. Group B:
i. Placed samples flat on sample holder. Perform argon plasma treatment.
ii. Spray coated primer layer (2% EVOH, 1:1 DMF:DMSO) onto stents. Used 1.5 sec. spray time, 1-2 passes to achieve 10-40 micrograms of coating.
iii. Baked the stents at 140° C. for 15 minutes in the convection oven.
iv. Took weight measurements on each stent to the nearest microgram.

v. Performed spray-coating process in CER under the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed stents into the TECOFLEX™ tubing with a balloon catheter—submerged in 37° C. water.

C. Group C:
i. Placed the samples flat on sample holder. Perform argon plasma treatment.
ii. Spray coated primer layer (2% EVOH, 1:1 DMF: DMSO) onto stents. Used 1.5 sec. spray time, 1-2 passes to achieve 10-40 micrograms of coating.
iii. Baked the stents at 140° C. for 30 minutes in the convection oven.
iv. Took weight measurements on each stent to the nearest microgram.
v. Performed spray-coating process in CER under the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed stents into the TECOFLEX™ tubing with a balloon catheter—submerged in 37° C. water.

D. Group D:
i. Placed samples flat on sample holder. Perform argon plasma treatment.
ii. Spray coated primer layer (2% EVOH, 1:1 DMF: DMSO) onto stents. Used 1.5 sec. spray time, 1-2 passes to achieve 10-40 micrograms of coating.
iii. Baked the stents at 140° C. for 60 minutes in the convection oven.
iv. Took weight measurements on each stent to the nearest microgram.
v. Performed spray-coating process in CER under the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed stents into the TECOFLEX™ tubing with a balloon catheter—submerged in 37° C. water.

E. Group E:
i. Placed samples flat on sample holder. Perform argon plasma treatment.
ii. Spray coated primer layer (2% EVOH, 1:1 DMF: DMSO) onto stents. Used 1.5 sec. spray time, 1-2 passes to achieve 10-40 micrograms of coating.
iii. Baked the stents at 140° C. for 120 minutes in the convection oven.
iv. Took weight measurements on each stent to the nearest microgram.
v. Performed spray-coating process in CER at the following conditions: 3 passes, 3-second spray, no blow.
vi. Weighed each sample at the end of the last pass to the nearest microgram.
vii. Baked samples for 240 minutes at 50° C.
viii. Took weight measurements of each stent to the nearest microgram.
ix. Placed stent into the TECOFLEX™ tube with balloon catheter—submerged in 37° C. water.

Test Procedure
1. Performed wet flow testing overnight for about 18 hrs.
2. Removed the stents from the TECOFLEX™ tubing with a stent catcher.
3. Counted the defects based on the number of peel defects at rings 3, 5, and 7 on the stents' OD. Count the defects on the ID of the same rings.
4. Stent weight could not be a measurable because of the loss of the drug and uptake of water.
5. All test samples were handled with PPE appropriate for drug containing stents.

| Data Summary and Results | |
| --- | --- |
| Group | Total Defects per Stent |
| Control | 3.33 |
| 15 min bake | 1.00 |
| 30 min bake | 3.00 |
| 60 min bake | 1.67 |
| 120 min bake | 1.33 |

Discussion

The control group with no primer layer had significantly more peel defects as compared to the treatment groups with a primer layer. The groups with shorter baking times (15 and 30 minutes) had higher defect counts than the groups with longer baking times.

Example 35

Objective

The objective of this experiment was to test the adhesive properties of an actinomycin-D containing coating on stainless steel stents having an EVOH primer layer. More specifically, different solvent systems (e.g., THF and DMF) were evaluated. The coated stents were tested under wet flow conditions of saline heated to 37° C. The number of "peel defects" on a select number of stent rings was observed.

| Group | Treatment | Flow Rate |
| --- | --- | --- |
| A Control | none | 50 mL/min |
| B | Argon plasma treatment + EVOH primer layer by spray (2% EVOH, 1:1 DMF: DMSO) baked at 140° C. for 15 minutes | 50 mL/min |
| C | Argon plasma treatment + EVOH primer layer by spray (2% EVOH, 1:1 DMF: DMSO) baked at 140° C. for 60 minutes | 50 mL/min |
| D | Argon plasma treatment + EVOH primer layer by spray (2% EVOH, 1:1 DMF: DMSO) baked at 140° C. for 240 minutes | 50 mL/min |
| E | Argon plasma treatment + EVOH primer layer by spray (2% EVOH, 1:1 THF: DMSO) baked at 140° C. for 60 minutes | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVOH in 1:1 DMF:DMSO solution;

4. 2% EVOH in 1:1 THF:DMSO solution;
5. Actinomycin-D solution, 1:1 THF:DMSO with 3:1 EVOH: Act-D, 2% EVOH;
6. 3.0 mm TECOFLEX™ tubing;
7. Saline;
8. Lint Free Wipes SU 00126 or equivalent;
9. 100% IPA;
10. Convection Oven;
11. Timer;
12. Plasma Machine;
13. Ultrasonic cleaner; and
14. Mettler balance with 0.1 micrograms resolution.

Preparation

1. Sonicated stents in IPA for 15 minutes.
2. Weighed each stent to the nearest microgram.
3. Prepared 5 stent samples for each group.
   A. Group A (Control):
      i. Performed spray-coating process in CER under the following conditions: 3 passes, 3-second spray, no blow.
      ii. Weighed each sample at the end of the last pass to the nearest microgram.
      iii. Baked samples for 240 minutes at 50° C.
      iv. Took weight measurements of each stent to the nearest microgram.
      v. Placed the stents into the TECOFLEX™ tubing with a balloon catheter—submerged in 37° C. water.
   B. Group B:
      i. Placed samples flat on a sample holder. Performed argon plasma treatment.
      ii. Spray coated the primer layer (2% EVOH, 1:1 DMF:DMSO) onto the stents. Used 1.5 sec. spray time, 1-2 passes to achieve 10-40 micrograms of coating.
      iii. Baked the stents at 140° C. for 15 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the TECOFLEX™ tubing with a balloon catheter—submerged in 37° C. water.
   C. Group C:
      i. Placed samples flat on a sample holder. Performed argon plasma treatment.
      ii. Spray coated the primer layer (2% EVOH, 1:1 DMF:DMSO) onto the stents. Used 1.5 sec. spray time, 1-2 passes to achieve 10-40 micrograms of coating.
      iii. Baked the stents at 140° C. for 60 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the TECOFLEX™ tubing with a balloon catheter—submerged in 37° C. water.
   D. Group D:
      i. Placed samples on flat on a sample holder. Performed argon plasma treatment.
      ii. Spray coated the primer layer (2% EVOH, 1:1 DMF:DMSO) onto the stents. Used 1.5 sec. spray time, 1-2 passes to achieve 10-40 micrograms of coating.
      iii. Baked the stents at 140° C. for 240 minutes in the convection oven.
      iv. Took weight measurements of each stent to the nearest microgram.
      v. Performed spray-coating process in CER at the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the TECOFLEX™ tubing with a balloon catheter—submerged in 37° C. water.
   E. Group E:
      i. Placed samples flat on a sample holder. Perform argon plasma treatment.
      ii. Spray coated the primer layer (2% EVOH, 1:1 THF:DMSO) onto the stents. Used 1.5 sec. spray time, 1-2 passes to achieve 10-40 micrograms of coating.
      iii. Baked the stents at 140° C. for 60 minutes in the convection oven.
      iv. Took weight measurements of each stent to the nearest microgram.
      v. Performed spray-coating process in CER under the following conditions: 3 passes, 3 second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the TECOFLEX™ tubing with a balloon catheter—submerged in 37° C. water.

Test Procedure

1. Performed wet flow testing overnight for about 18 hrs.
2. Removed the stents from the TECOFLEX™ tubing with a stent catcher.
3. Counted the defects, based on the number of peel defects at rings 3, 5, and 7 on the stents' OD. Counted defects on the ID of the same rings.
4. The weight of the stents could not be a measurable because of the loss of the drug and uptake of water.
5. All test samples were handled with PPE appropriate for drug containing stents.

Data Summary and Results

| Group | Total Defects per Stent |
|---|---|
| No primer control | 0.00 |
| 15 min. bake | 0.00 |
| 60 min. bake | 0.33 |
| 240 min. bake | 0.00 |
| THF, 15 min. bake | 0.00 |

Example 36

Objective

The objective of this experiment was to test the adhesive properties of an actinomycin-D containing coating on stainless steel stents having an EVOH primer layer made from a DMSO:THF solution applied to the stents. The coated stents were tested under wet flow conditions of saline heated to 37° C. The number of "peel defects" on a select number of stent rings was observed.

| Group | Treatment | Drying Time (min.) |
|---|---|---|
| A | Arson plasma treatment + EVOH primer | 15 |
| B | Argon plasma treatment + EVOH primer | 30 |
| C | Argon plasma treatment + EVOH primer | 60 |
| D | Argon plasma treatment + EVOH primer | 90 |
| E | Argon plasma treatment + EVOH primer | 120 |

Materials and Equipment
1. 10, 13 mm SOLO stents, cleaned ultrasonically in IPA for 15 minutes;
2. 2% EVOH in 1:1 THF:DMSO solution;
3. 10 Balloon catheters or subassemblies to expand the stents;
4. Actinomycin-D solution, 1:1 THF:DMSO with 1:3 Act-D:EVOH, 2% EVOH;
5. 4.0 mm TECOFLEX™ tubing;
6. Saline;
7. Lint Free Wipes SU 00126 or equivalent;
8. 100% IPA;
9. Convection Oven;
10. Timer;
11. Plasma Machine;
12. Ultrasonic cleaner;
13. Mettler balance with 0.1 microgram resolution;
14. Spray/bake mandrels and tips;
15. Flow Meter, N1429;
16. Microscope, minimum magnification 50×;
17. EFD controller with spray apparatus without translational stage; and
18. EFD controller with spray apparatus with translational stage.

Preparation
1. Sonicated the stents in IPA for 15 minutes.
2. Weighed each stent to the nearest microgram.
3. Prepare the stent samples for each group.
   A. Primer Coat
      i. Placed samples on sample holder. Performed argon plasma treatment.
      ii. Sprayed the primer layer (2% EVOH, 1:1 THF:DMSO) onto the stents with translational spray coater. Used 1.5 sec. for the spray time and speed 7 to achieve 10-40 µg of coating.
      iii. Baked the stents at 140° C. for the specified time in the convection oven.
      iv. Weighed the stents and recorded measurements to the nearest microgram.
   B. Drug Coat
      i. Sprayed the stents with a 3:1, EVOH:Act-D, 2% EVOH, 1:1 DMSO:THF solution for three seconds per pass for three passes. After each spray pass, dried the stents in the convection oven for 15 minutes at 50° C.
      ii. Weighed the stents and recorded measurements. If the drug coat weight matched the target weight, the stents were returned to the oven for 240 minutes. If weight gain did not match, the stents were returned to the glove box for additional spray coat application. Spray time on subsequent passes was adjusted to achieve target weight.
4. Wet Flow Test Sample Preparation
   A. Crimped the stents onto the balloon catheters.
   B. Inflated the stents to 4.0 mm in the TECOFLEX™ tubing with the balloon catheters—submerged in 37° C. water.
   C. Disposed Act-D contaminated water as hazardous waste.

Test Method/Procedure
1. Set flow rate at 50 ml/min.
2. Performed wet flow testing overnight for about 18 hrs.
3. Removed the stents from the TECOFLEX™ tubing with a stent catcher.
4. Counted defects, based on the number of peel defects at rings 1, 3, 5, 7, and 10 on the stents' OD. Counted defects on the ID of the same rings.
5. All test samples were handled with PPE appropriate for drug containing stents.

| Data Summary and Results | | | |
|---|---|---|---|
| Drying Time (min.) | Total Defects per Stent | Total Defects per Stent (end rings) | Total Defects per Stent (middle rings) |
| 15 | 0.0 | 0.0 | 0.0 |
| 30 | 2.0 | 2.0 | 0.0 |
| 60 | 1.0 | 1.0 | 0.0 |
| 90 | 0.0 | 0.0 | 0.0 |
| 120 | 0.5 | 0.5 | 0.0 |

Example 37

35 13 mm PENTA stents (available from Guidant Corporation) were coated by spraying a 2% (w/w) solution of EVOH (44 mole % ethylene) in 98% (w/w) dimethylacetamide. The solvent was removed by baking at 140° C. for 2 hours. A solution of 1.9% (w/w) EVOH and 0.7% (w/w) 40-O-(2-hydroxy)ethyl-rapamycin in a mixture of 68.2% (w/w) dimethylacetamide and 29.2% (w/w) ethanol was spray coated onto the stents to a thickness with a target of 175 µg of 40-O-(2-hydroxy)ethyl-rapamycin on each stent. The stents were then baked at 50° C. for 2 hours. A barrier layer was formed by spraying the stents with a 4% (w/w) solution of EVOH in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 43±3 µg of polymer. For the reservoir layer, the target drug:polymer ratio was 1:2.857, the target dry weight for the entire reservoir coating was 675 µg and the average actual dry weight was 683±19 µg. Also for the reservoir layer, the average total drug content of the stent coatings was determined by the process described in Example 38. The average drug content was 133 µg or 152 µg/cm². For the barrier layer, the target dry weight of polymer was 300 µg and the measured average dry weight was 320±13 µg.

Example 38

A drug-coated stent was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The drug solution was the analyzed by HPLC. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard. The total drug content of the stent was then calculated.

Example 39

34 13 mm PENTA stents were coated by spraying a 2% (w/w) solution of EVOH and 98% (w/w) dimethylacetamide. The solvent was removed by baking at 140° C. for 2 hours. A solution of 1.9% (w/w) EVOH and 1.1% (w/w) 40-O-(2-hydroxy)ethyl-rapamycin in a mixture of 67.9% (w/w) dimethylacetamide and 29.1% (w/w) ethanol was spray coated onto the stents to a thickness with a target of 275 µg of 40-O-(2-hydroxy)ethyl-rapamycin on each stent. The stents were then baked at 50° C. for 2 hours. A barrier layer was formed by spraying the stents with a 4% (w/w) solution of EVOH in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 43±3 µg of polymer. For the reservoir layer, the target drug:polymer ratio was 1:1.75, the target dry weight for the entire reservoir coating was 757 µg and the average actual dry weight was 752±23 µg. Also for the reservoir layer, the average total drug content of the stent coatings was determined by the process described in Example 38. The average drug content was 205 µg or 235 µg/cm². For the barrier layer, the target dry weight of polymer was 200 µg and the measured average dry weight was 186±13 µg.

Example 40

24 13 mm PENTA stents were coated by spraying a 2% (w/w) solution of EVOH and 98% (w/w) dimethylacetamide. The solvent was removed by baking at 140° C. for 2 hours. A solution of 1.9% (w/w) EVOH and 1.2% (w/w) 40-O-(2-hydroxy)ethyl-rapamycin in a mixture of 67.8% (w/w) dimethylacetamide and 29.1% (w/w) ethanol was spray coated onto the stents to a thickness with a target of 325 µg of 40-O-(2-hydroxy)ethyl-rapamycin on each stent. The stents were then baked at 50° C. for 2 hours. A barrier layer was formed by spraying the stents with a 4% (w/w) solution of EVOH in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 41±2 µg of polymer. For the reservoir layer, the target drug:polymer ratio was 1:1.6, the target dry weight for the entire reservoir coating was 845 µg and the average actual dry weight was 861±16 µg. Also for the reservoir layer, the average total drug content of the stent coatings was determined by the process described in Example 38. The average drug content was 282 µg or 323 µg/cm². For the barrier layer, the target dry weight of polymer was 125 µg and the measured average dry weight was 131±9 µg.

Example 41

This Example 41 is referred to as the "Release Rate Profile Procedure." A drug-coated stent was placed on a stent holder of a Vankel Bio-Dis release rate tester (Vankel, Inc., Cary, N.C.). The stent was dipped into an artificial medium which stabilizes the 40-O-(2-hydroxy)ethyl-rapamycin in the testing solution, including a phosphate buffer saline solution (10 mM, pH 7.4) with 1% TRITON X-100 (Sigma Corporation), for a designated amount of time (e.g., 3 hours). Then the solution was analyzed for the amount of drug released from the stent coating using an HPLC process. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µm particle size), maintained at a temperature of 40° C. The mobile phase consisted of 75% acetonitrile and 25% 20 mMolar ammonium acetate. The flow rate was set on 1 ml/min. After the drug solution was analyzed by HPLC the results were quantified by comparing the release rate results with a reference standard.

If the experimental protocol required that the stent coating be subjected to experimental conditions for an additional time, the stent was then dipped in a fresh medium solution for the necessary amount of time (e.g., another 3 hours) and the drug released in the solution was analyzed again according to the HPLC procedure described above. The procedure was repeated according to the number of data points required. The release rate profile could then be generated by plotting cumulative drug released in the medium vs. time.

Example 42

The release rate of 40-O-(2-hydroxy)ethyl-rapamycin from the stents with coatings produced by the processes under Examples 37, 39 and 40 were tested using the in vitro HPLC process as described in Example 41. The solution for each stent underwent two HPLC runs, and the results were averaged.

The following Table 7 summarizes the results of the release rate procedure for two stents from Example 37:

TABLE 7

| | Time (hrs) | | | | | | |
|---|---|---|---|---|---|---|---|
| | 3 | 6 | 9 | 12 | 23 | 32 | 48 |
| Cumulative Release from Stent 1 (µg) | 3.72 | 5.62 | 7.12 | 8.43 | 12.28 | 15.31 | 20.28 |
| Cumulative Release from Stent 2 (µg) | 4.18 | 6.53 | 8.54 | 10.29 | 15.64 | 19.66 | 26.3 |

The following Table 8 summarizes the results of the release rate procedure for two stents from Example 39:

TABLE 8

|  | Time (hrs) | | | | | | |
| --- | --- | --- | --- | --- | --- | --- | --- |
|  | 3 | 6 | 9 | 12 | 23 | 32 | 48 |
| Cumulative Release from Stent 1 (μg) | 29.73 | 45.35 | 57.79 | 68.19 | 95.2 | 110.85 | 130.75 |
| Cumulative Release from Stent 2 (μg) | 26.36 | 41.2 | 53.5 | 63.99 | 93.93 | 112.31 | 135.7 |

The following Table 9 summarizes the results of the release rate procedure for two stents from Example 40:

TABLE 9

|  | Time (hrs) | | | | | | |
| --- | --- | --- | --- | --- | --- | --- | --- |
|  | 3 | 6 | 9 | 12 | 23 | 32 | 48 |
| Cumulative Release from Stent 1 (μg) | 46.24 | 67.4 | 82.79 | 94.92 | 124.72 | 141.96 | 165.12 |
| Cumulative Release from Stent 2 (μg) | 44.66 | 66.74 | 82.26 | 94.49 | 123.92 | 140.07 | 159.65 |

Figure 11:
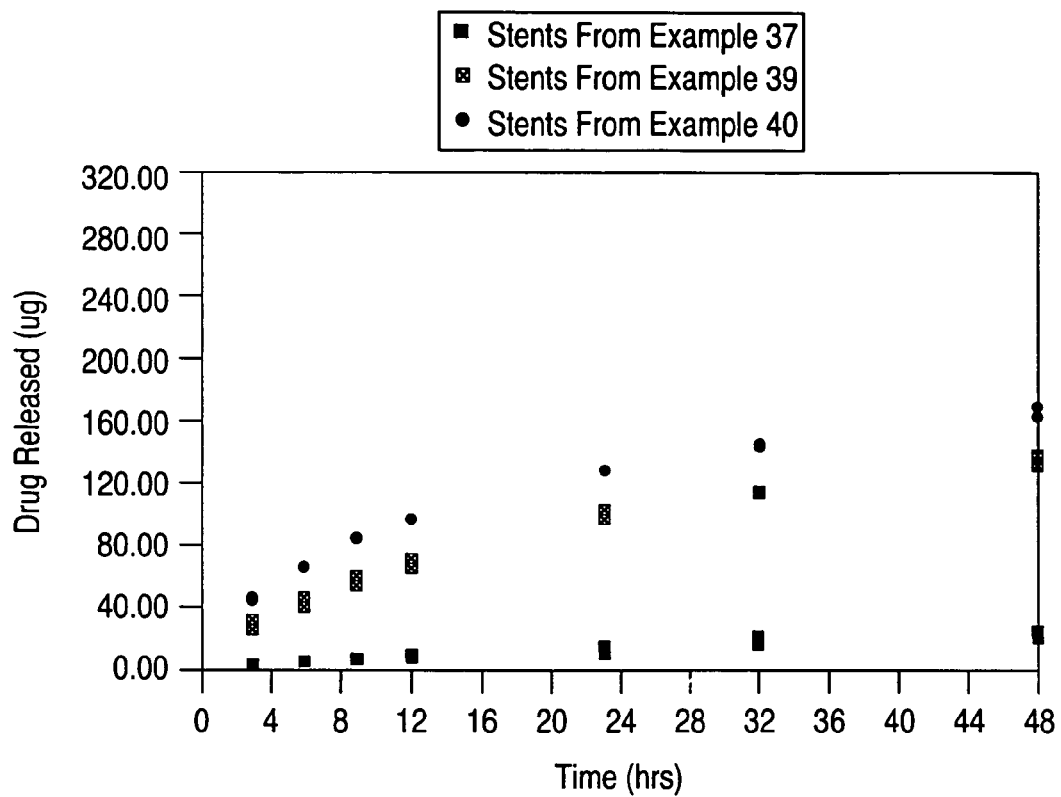
FIG. 11 is a graph showing the release rate of an active agent from stent coatings as referred to in Example 42.

A comparison of the release rates for the stents from Examples 37, 39 and 40 is graphically shown in FIG. 11.

Example 43

The following Example 43 is referred to as the "3 day In Vivo Release Rate Procedure" or the "9 day In Vivo Release Rate Procedure," depending on the number of days the stents are inserted into the experimental animal. The following are the materials used for this Example:

1. Experimental animal: One 30-45 kg Yorkshire cross pig;
2. BMW™ wires 0.014", 190 cm;
3. Guide wire 0.035", 190 cm;
4. Viking guide catheters, 7F;
5. Introducer sheaths (8-10F);
6. ACS 20/20 Indeflator™ Inflation Device;
7. Saline; solution with heparin;
8. Nitroglycerin, Lidocaine, other inotropic/chronotropic drugs;
9. Standard surgical equipment, anesthetic, and medications as necessary;
10. Respiratory and hemodynamic monitoring systems;
11. Positive pressure ventilator and associated breathing circuits;
12. ACT machine and accessories;
13. PTCA accessories;
14. Ambulatory defibrillator;
15. Fluoroscopy equipment; and
16. Non-ionic contrast agent.

The following was the procedure used for this Example:
A. Animal Preparation.
1. Administer Aspirin (325 mg PO) once daily starting one day prior to stent implantation.
2. Sedate the pig.
3. Intubate the trachea via an oral approach.
4. Deliver isoflurane (up to about 5%) to achieve and maintain an adequate plane of anesthesia.
5. Shave the sheath introduction area free of hair and scrub the surgical site with surgical soap and/or antiseptic solution.
6. Place a 7F introducer sheath into the right or left femoral artery.
7. Obtain an arterial blood sample for a baseline ACT.
8. Administer heparin 200 units/kg IV (not to exceed 100,000 units) and obtain a blood sample for measurement of ACT 5-10 minutes later.
9. Repeat heparin as needed to maintain ACT≧300 seconds.
10. Measure and record arterial blood pressure, heart rate and electrocardiogram (ECG).

B. Angiography for vessel selection.
1. Advance the guiding catheter over the guidewire into the aortic arch and cannulate the desired vessel.
2. Administer nitroglycerin (200 μg) intra-luminally prior to baseline angiography.
3. Perform baseline angiogram and record images on cine.
4. With the diameter of the guiding catheter as a reference, select vasculature that will allow a target stent to artery ratio of about 1.1:1.0.

C. Stent Preparation and Deployment.
1. Perform online QCA and measure baseline proximal, target, and distal reference sites.
2. Administer nitroglycerin (200 μg) intra-luminally prior to stent deployment, then as needed to control coronary artery vasospasm.
3. Inspect the stent delivery system. Ensure that the stent is correctly positioned on the balloon. Inspect the stent for any abnormalities.
4. Flush guidewire lumen with heparinized saline until fluid exits the guidewire notch.
5. Prepare Indeflator/syringe with diluted (approximately 50:50) contrast medium.
6. Attach syringe to test catheter inflation port; use standard techniques to fill the inflation lumen with diluted contrast.
7. Purge syringe and test catheter inflation lumen of all air.
8. Purge Indeflator of all air and attach to test catheter inflation port.
9. Position an appropriate guidewire in the distal bed of the target artery.
10. Insert the stent delivery system through the guiding catheter over the guidewire.
11. Advance the stent delivery system to the pre-selected arterial deployment site.
12. Position balloon for inflation.
13. Refer to IFU for inflation strategy. If no IFU available, inflate the balloon at a slow steady rate to a pressure that expands the stent to the desired diameter. Hold at this pressure for 30 seconds.
14. Record inflated balloon by pulling image on cine. Perform on-line QCA and measure the inflated balloon diameter.
15. Deflate balloon by pulling negative pressure. While withdrawing the system, observe tactually and fluoroscopically. Record any resistance.
16. Administer nitroglycerin (200 μg) intra-luminally.
17. Assess patency, deployment, and placement of stent via coronary angiography.
18. Assess TIMI angiographic low grade.
19. Record on cine and video.
20. Measure post-proximal, target, and distal MLD with QCA.

21. Repeat Section C with remaining stent delivery system.
22. Measure and record heart rate, arterial blood pressure and electrocardiogram (ECG).

D. Stent Procedure End.
1. Remove the guidewire, guiding catheter and introducer sheath.
2. Remove introducer sheath from the femoral artery.
3. Apply pressure to the femoral artery at the side of sheath entry.
4. Allow the animal to recover from anesthesia in an individual cage.
5. Give Buprenorphine (0.05 mg/kg) PRN as needed for pain.
6. Administer Ticlopidine (250 mg PO) and aspirin (325 mg PO) once daily until date of follow-up angiography.

E. Study End.
1. Euthanize the pig with an overdose of barbiturates and/or potassium chloride.
2. Excise the heart without flushing the vessels.
3. Harvest all stented arteries.
4. Remove the stent from all treated arteries and place them in dark colored amber vials for subsequent drug concentration analysis.
5. Snap freeze the arterial tissue in liquid nitrogen and store at −70° C. until subsequent analysis of tissue for drug concentrations as determined by HPLC.

The stents harvested from the experimental animals were tested using an HPLC procedure to determine how much drug remained on the stents. A drug-coated stent removed from the experimental animal was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard. The total drug released in vivo was the difference between the average drug loaded on the stents and the amount of drug remaining on the stents after the stent implantation into the experimental animal.

Example 44

The release rate of 40-O-(2-hydroxy)ethyl-rapamycin from the stents with coatings produced by the process under Example 37 were tested using a 3 day in vivo process as described in Example 43. In particular, stents from Example 37 were implanted into experimental animals and then the stents were tested by HPLC to determine how much 40-O-(2-hydroxy)ethyl-rapamycin diffused from the stent coating into the blood vessel. According to the HPLC analysis, 21.8 μg of the 40-O-(2-hydroxy)ethyl-rapamycin was released from the coating in 3 days, or 16.4% of the total drug content of the coating.

Example 45

The release rate of 40-O-(2-hydroxy)ethyl-rapamycin from the stents with coatings produced by the process under Example 39 were tested using a 3 day in vivo process as described in Example 43. In particular, stents from Example 39 were implanted into experimental animals and then the stents were tested by HPLC to determine how much 40-O-(2-hydroxy)ethyl-rapamycin diffused from the stent coating into the blood vessel. According to the HPLC analysis, 7.8 μg of the 40-O-(2-hydroxy)ethyl-rapamycin was released from the coating in 3 days, or 3.8% of the total drug content of the coating.

Example 46

The release rate of 40-O-(2-hydroxy)ethyl-rapamycin from the stents with coatings produced by the process under Example 40 were tested using a 3 day in vivo process as described in Example 43. In particular, stents from Example 40 were implanted into experimental animals and then the stents were tested by HPLC to determine how much 40-O-(2-hydroxy)ethyl-rapamycin diffused from the stent coating into the blood vessel. According to the HPLC analysis, 50.8 μg of the 40-O-(2-hydroxy)ethyl-rapamycin was released from the coating in 3 days, or 18% of the total drug content of the coating.

Example 47

The release rate of 40-O-(2-hydroxy)ethyl-rapamycin from the stents with coatings produced by the process under Example 39 were tested using a 9 day in vivo process as described in Example 43. In particular, stents from Example 39 were implanted into experimental animals and then the stents were tested by HPLC to determine how much 40-O-(2-hydroxy)ethyl-rapamycin diffused from the stent coating into the blood vessel. According to the HPLC analysis, 29.7% of the 40-O-(2-hydroxy)ethyl-rapamycin was released from the coating in 9 days.

Example 48

The release rate of 40-O-(2-hydroxy)ethyl-rapamycin from the stents with coatings produced by the process under Example 40 were tested using a 9 day in vivo process as described in Example 43. In particular, stents from Example 40 were implanted into experimental animals and then the stents were tested by HPLC to determine how much 40-O-(2-hydroxy)ethyl-rapamycin diffused from the stent coating into the blood vessel. According to the HPLC analysis, 39.4% of the 40-O-(2-hydroxy)ethyl-rapamycin was released from the coating in 9 days.

Example 49

A 13 mm PIXEL stent (available from Guidant Corporation) was coated. The stent had a yellowish-gold coating that included EVOH and actinomycin D. The ends of the stent were heated with a cauterizer tip for fifteen (15) seconds at a current setting of 2.2 Amps, which corresponded to a temperature of about 106° C. at a distance of about 0.006 inches from the stent.

After the stent was exposed to heat from the cauterizer tip, the stent was submerged in a 50% (w/w) methanol:water bath. After twenty-four (24) hours, the stent was observed to have drug present at the stent end rings as indicated by a yellowish hue. The middle section of the stent, however, was clear, indicating that the drug had been released through the polymer. This process was repeated on 40 stents yielding similar results for all the stents.

Example 50

13 mm PIXEL stents were coated. The stents had yellowish-gold coatings that included EVOH and actinomycin D. The stents were separated into three experimental groups, and the ends of the stents were heated with a cauterizer tip according to the parameters shown in Table 10 for each group. After the stents were exposed to heat from the cauterizer tip, the stent was submerged in a 50% (w/w) methanol:water bath. After twenty-four (24) hours, the stents were observed as summarized in Table 10.

TABLE 10

| Experimental Group | Current (Amps) | Exposure Time (Seconds) | Observation |
|---|---|---|---|
| 1 | 2.0 | 10 | Least gold coloration in the end sections compared to the stents from Experimental Groups 2 and 3, indicating the least amount of drug remaining in the stent coating. |
| 2 | 2.2 | 8 | Moderate gold coloration in the end sections. |
| 3 | 2.4 | 5 | Most gold coloration in the end sections compared to the stents from Experimental Groups 1 and 2 indicating the most amount of drug remaining in the stent coating. |

It was observed that the coating in the middle section of the stents, which did not have significant exposure to heat from the cauterizer tip, was clear. This indicates that the drug had been eluted from the stents. On the other hand, the end rings of the stents which had been exposed to heat from the cauterizer tip still appeared gold in color, indicating the presence of drug in the stent coating. The results above indicate that varying the amount of time and heat exposure can modify the elution rate of drug from the stent.

Example 51

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 26 μg of polymer, and a measured average dry weight of 28±3 μg of polymer. For the reservoir layer, the target drug:polymer ratio was 1:1.25, and the measured average drug content was 128 μg. For the barrier layer, the measured average dry weight was 84 μg.

Example 52

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 26 μg of polymer, and a measured average dry weight of 28±2 μg of polymer. For the reservoir layer, the target drug:polymer ratio was 1:1.5, and the measured average drug content was 130 μg. For the barrier layer, the measured average dry weight was 81 μg.

After the solvent had been substantially removed and the coatings had been formed, a select number of stents were then heat treated by exposing the stents to a heat of 80° C. for 2 hours.

Example 53

The release rate of 40-O-(2-hydroxy)ethyl-rapamycin from the stents with coatings produced by the processes under Examples 51 and 52 were tested using the process described in Example 41. The following Table 11 summarizes the results of the release rate procedure for three stents from Example 51:

TABLE 11

|  | Time (hrs) | | | | | | |
|---|---|---|---|---|---|---|---|
|  | 3 | 6 | 9 | 12 | 24 | 32 | 48 |
| Cumulative Release from Stent 1 (μg) | 15.44 | 24.63 | 32.20 | 38.43 | 56.04 | 64.81 | 77.36 |
| Cumulative Release from Stent 2 (μg) | 12.70 | 21.29 | 28.57 | 34.55 | 51.19 | 59.27 | 71.15 |
| Cumulative Release from Stent 3 (μg) | 13.00 | 21.92 | 29.31 | 35.40 | 52.55 | 60.48 | 72.05 |

The following Table 12 summarizes the results of the release rate procedure for three stents from Example 52:

TABLE 12

|  | Time (hrs) | | | | | | |
|---|---|---|---|---|---|---|---|
|  | 3 | 6 | 9 | 12 | 24 | 32 | 48 |
| Cumulative Release from Stent 1 (μg) | 5.52 | 9.37 | 12.73 | 15.71 | 24.33 | 29.20 | 38.02 |
| Cumulative Release from Stent 2 (μg) | 6.73 | 10.86 | 14.39 | 17.41 | 25.99 | 30.29 | 38.00 |
| Cumulative Release from Stent 3 (μg) | 5.76 | 9.14 | 12.02 | 14.50 | 21.21 | 24.61 | 31.23 |

Figure 12:
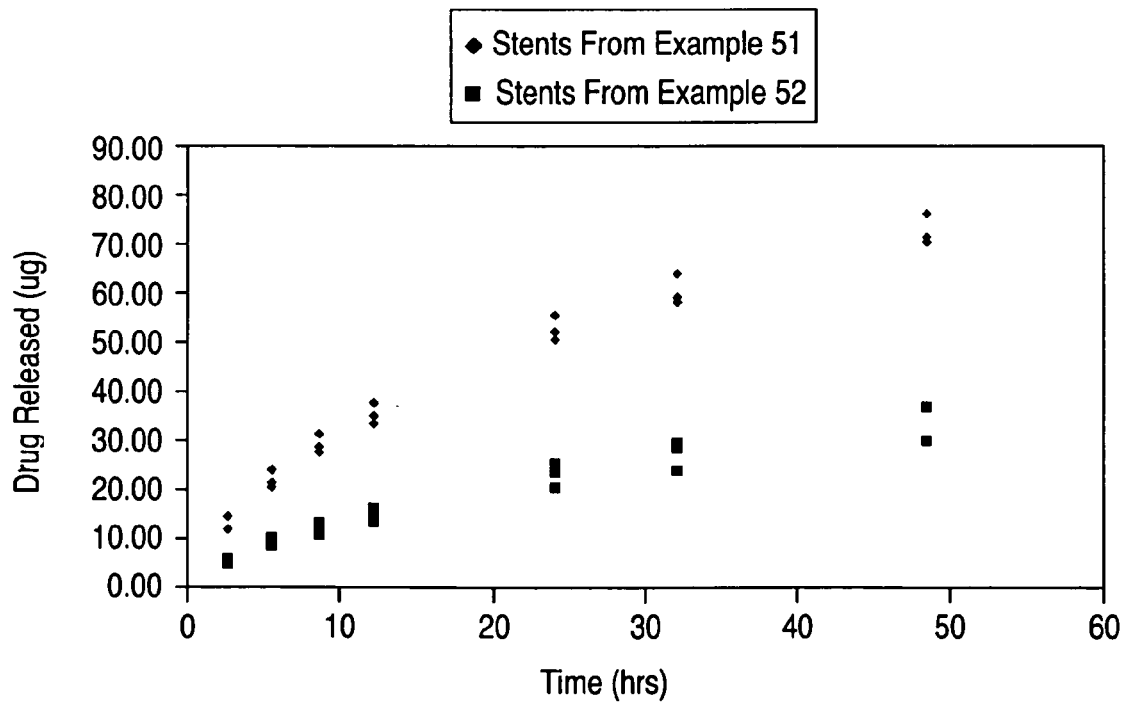
FIG. 12 is a graph showing the release rate of an active agent from stent coatings as referred to in Example 53.

A comparison of the release rates for the stents from Examples 51-52 is graphically shown in FIG. 12. The results unexpectedly show that the stent coatings that were exposed to thermal treatment in Example 52 have a significantly lower release rate than the stent coatings of Example 51.

Example 54

This Example 54 is referred to as the "Porcine Serum Release Rate Procedure." A drug-coated stent was placed on a stent holder of a Vankel Bio-Dis release rate tester. The stent was dipped into porcine serum, with 0.1% sodium azide added, for 24 hrs. The stent was removed from the porcine serum and the drug solution analyzed by an HPLC procedure to determine how much drug was released into the porcine serum. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard.

Example 55

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 45±1 μg of polymer. For the reservoir layer, the drug:polymer ratio was 1:1, and the measured average drug content was 151 μg as determined by Example 38. For the barrier layer, the measured average dry weight was 234 μg.

After the coatings were formed on the stents, a select number of stents were tested for the drug release rate from the coatings according to the procedure described in Example 54. It was determined that the average drug released in 24 hours was 32.6 μg, or 21.6% of the total.

Example 56

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 44±3 μg of polymer. For the reservoir layer, the drug:polymer ratio was 1:1.8, and the measured average drug content was 97 μg as determined by Example 38. For the barrier layer, the measured average dry weight was 184 μg.

After the coatings were formed on the stents, a select number of stents were tested for the drug release rate from the coatings according to the procedure described in Example 54. It was determined that the average drug released in 24 hours was 24.1 μg, or 24.8% of the total.

Example 57

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 4±1 μg of polymer. For the reservoir layer, the drug:polymer ratio was 1:1.8, and the measured average drug content was 227 μg as determined by Example 38. For the barrier layer, the measured average dry weight was 181 μg.

After the coatings were formed on the stents, a select number of stents were tested for the drug release rate from the coatings according to the procedure described in Example 54. It was determined that the average drug released in 24 hours was 27.5 μg, or 12.1% of the total.

Example 58

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. No barrier layer was applied for this Example.

A select number of stents were analyzed to quantify the coating components. For the primer layer, there was a target dry weight of 40 μg of polymer, and a measured average dry weight of 44±2 μg of polymer. For the reservoir layer, the drug:polymer ratio was 1:1.8, and the measured average drug content was 221 μg as determined by Example 38.

After the coatings were formed on the stents, a select number of stents were tested for the drug release rate from the coatings according to the procedure described in Example 54. It was determined that the average drug released in 24 hours was 129.4 μg, or 58.55% of the total.

Example 59

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 42 µg of polymer. For the reservoir layer, the drug:polymer ratio was 1:1.5, and the measured average drug content was 184 µg as determined by Example 38. For the barrier layer, the measured average dry weight was 81 µg.

After the coatings were formed on the stents, a select number of stents were tested for the drug release rate from the coatings according to the procedure described in Example 54. It was determined that the average drug released in 24 hours was 70.1 µg, or 38.1% of the total.

Example 60

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 45±1 µg of polymer. For the reservoir layer, the drug:polymer ratio was 1:1.75, and the measured average drug content was 200 µg as determined by Example 38. For the barrier layer, the measured average dry weight was 180 µg.

After the coatings were formed on the stents, a select number of stents were tested for the drug release rate from the coatings according to the procedure described in Example 54. It was determined that the average drug released in 24 hours was 39.0 µg, or 19.5% of the total.

Example 61

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 41±4 µg of polymer. For the reservoir layer, the drug:polymer ratio was 1:1, and the measured average drug content was 167 µg as determined by Example 38. For the barrier layer, the measured average dry weight was 184 µg.

After the coatings were formed on the stents, a select number of stents were tested for the drug release rate from the coatings according to the procedure described in Example 54. It was determined that the average drug released in 24 hours was 6.0 µg, or 3.6% of the total.

Example 62

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 26 µg of polymer, and a measured average dry weight of 24±2 µg of polymer. For the reservoir layer, the drug:polymer ratio was 1:1.25, and the measured average drug content was 120 µg as determined by Example 38. For the barrier layer, the measured average dry weight was 138 µg.

After the coatings were formed on the stents, a select number of stents were tested for the drug release rate from the coatings according to the procedure described in Example 54. It was determined that the average drug released in 24 hours was 11.0 µg, or 9.2% of the total.

Example 63

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) polybutylmethacrylate ("PBMA"), 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 40 µg of polymer, and a measured average dry weight of 44±4 µg of polymer. For the reservoir layer, the drug:polymer ratio was 1:1, and the measured average drug content was 183 µg as determined by Example 38. For the barrier layer, the measured average dry weight was 168 µg.

After the coatings were formed on the stents, a select number of stents were tested for the drug release rate from the coatings according to the procedure described in Example 54. It was determined that the average drug released in 24 hours was 21.6 µg, or 11.8% of the total.

Example 64

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) PBMA, 5.7% (w/w) acetone, 50% (w/w) xylene and 43.3% (w/w) HFE FLUX REMOVER. Another 2 hour bake at 50° C. was performed to remove the solvent.

A select number of stents were analyzed to quantify the coating components. For the primer layer, there was a target dry weight of 40 µg of polymer, and a measured average dry weight of 41±2 µg of polymer. For the reservoir layer, the drug:polymer ratio was 1:1.8, and the measured average drug content was 102 µg as determined by Example 38. For the barrier layer, the measured average dry weight was 97 µg.

After the coatings were formed on the stents, a select number of stents were tested for the drug release rate from the coatings according to the procedure described in Example 54. It was determined that the average drug released in 24 hours was 9.1 µg, or 8.9% of the total.

Example 65

8 mm PIXEL stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) PBMA, 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 26 µg of polymer, and a measured average dry weight of 27±2 µg of polymer. For the reservoir layer, the drug:polymer ratio was 1:1.25, and the measured average drug content was 120 µg as determined by Example 38. For the barrier layer, the measured average dry weight was 68 µg.

After the coatings were formed on the stents, a select number of stents were tested for the drug release rate from the coatings according to the procedure described in Example 54. It was determined that the average drug released in 24 hours was 22.0 µg, or 18.3% of the total.

Example 66

A select number of stents from Example 39 were tested for the drug release rate from the coatings according to the procedure described in Example 54. It was determined that the average drug released in 24 hours was 22.8 µg, or 11.1% of the total.

Example 67

A select number of stents from Example 40 were tested for the drug release rate from the coatings according to the procedure described in Example 54. It was determined that the average drug released in 24 hours was 57.0 µg, or 20.2% of the total.

Example 68

Two stents were coated by spraying a 2% (w/w) solution of EVOH and 98% (w/w) dimethylacetamide to form a primer layer. For the primer layer, there was a target dry weight of 100 µg of polymer, and the measured dry weights were 93 µg and 119 µg, respectively. The two stents were then coated with an EVOH-40-O-(2-hydroxy)ethyl-rapamycin blend at a drug:polymer ratio of 2:1 to produce a reservoir layer. After application, it was determined that the reservoir layers had weights of 610 µg and 590 µg, respectively. From the total weight of the reservoir layers and the drug:polymer ratio, it was estimated that the coatings contained about 407 µg and 393 µg of 40-O-(2-hydroxy)ethyl-rapamycin, respectively. Polymeric barrier layers were also applied to the stents and it was determined that the weights of the barrier layers were 279 µg and 377 µg, respectfully.

The stents from this Example were then sterilized using an ethylene oxide sterilization process. In particular, the stents were placed in a chamber and exposed to ethylene oxide gas for 6 hours at 130-140° F., with a relative humidity of 45-80%. The stents were then aerated for about 72 hours at 110-130° F.

Figure 13:
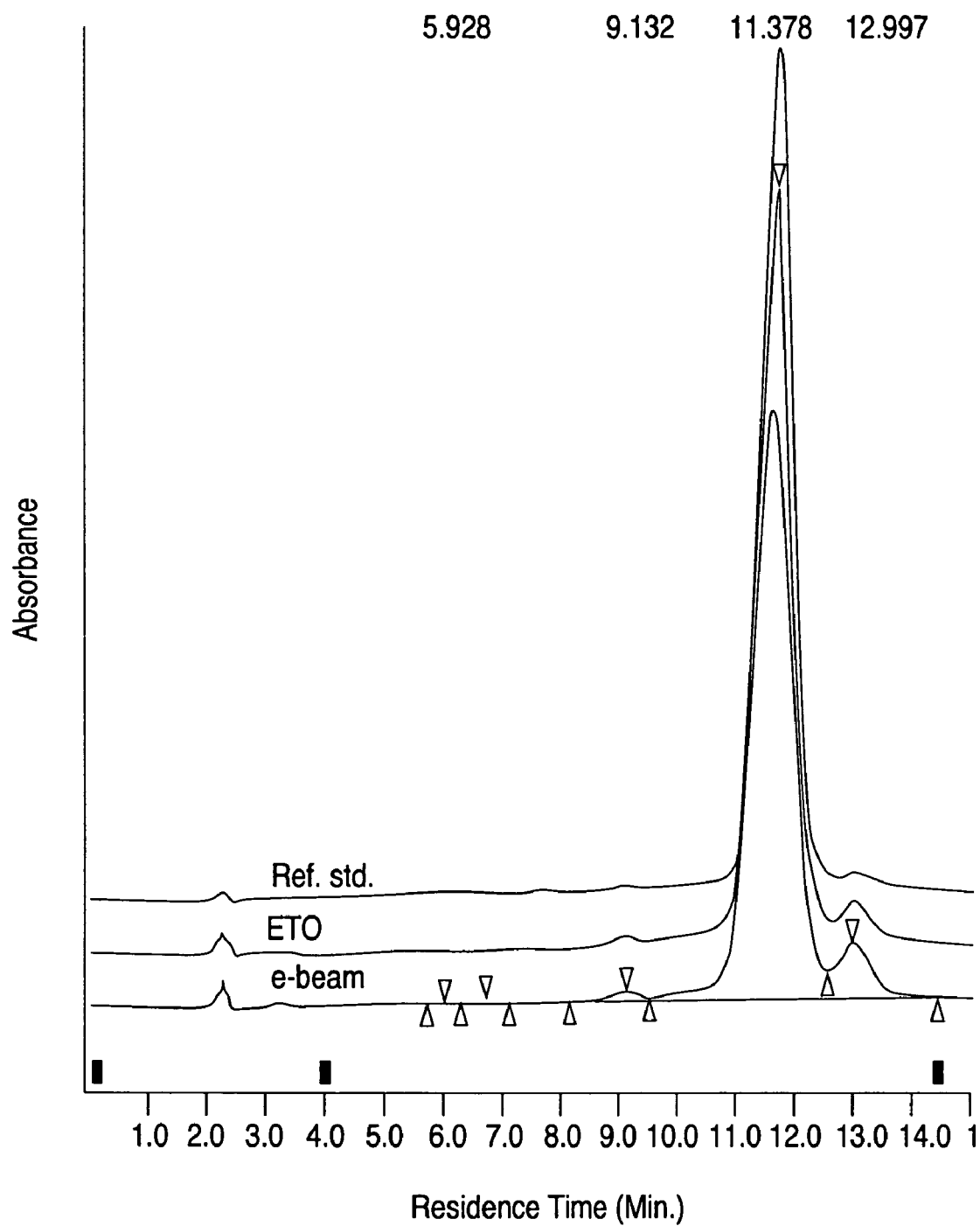
FIG. 13 is a chromatograph as referred to in Examples 68 and 69.

After sterilization, the coatings were then analyzed using an HPLC to determine the peak purity of the drug in the stent coatings. It was determined that the 40-O-(2-hydroxy)ethyl-rapamycin in the coatings had peak purities of about greater than 95%. FIG. 13 is a chromatograph showing the peak purity the 40-O-(2-hydroxy)ethyl-rapamycin in one of the coatings, labeled "ETO," as compared to a reference standard for 40-O-(2-hydroxy)ethyl-rapamycin, labeled "Ref. Std."

Example 69

Two stents were coated by spraying a 2% (w/w) solution of EVOH and 98% (w/w) dimethylacetamide to form a primer layer. For the primer layer, there was a target dry weight of 100 µg of polymer, and the measured dry weights were 99 µg and 94 µg, respectively. The two stents were then coated with an EVOH-40-O-(2-hydroxy)ethyl-rapamycin blend at a drug:polymer ratio of 2:1 to produce a reservoir layer. After application, it was determined that the reservoir layers had weights of 586 µg and 588 µg, respectively. From the total weight of the reservoir layers and the drug:polymer ratio, it was estimated that the coatings contained about 391 µg and 392 µg of 40-O-(2-hydroxy)ethyl-rapamycin, respectively. Polymeric barrier layers were also applied to the stents and it was determined that the weights of the barrier layers were 380 µg and 369 µg, respectfully.

The stents from this Example were then sterilized using an e-beam sterilization process. In particular, the stents were placed in a stent container which was run through an e-beam chamber. While moving through the e-beam chamber via a conveyor belt, the stent container was exposed to an e-beam with a constant energy level so that the stent container received between 33.11 and 46.24 Kgy. The stent therefore at any point along the length of the stent received at a minimum 25 Kgy.

After sterilization, the coating was then analyzed using an HPLC to determine the peak purity of the drug in the stent coating. It was determined that the 40-O-(2-hydroxy)ethyl-rapamycin in the coating had a peak purity of about greater than 95%. FIG. 13 is a chromatograph showing the peak purity the 40-O-(2-hydroxy)ethyl-rapamycin in one of the coatings, labeled "e-beam," as compared to a reference standard for 40-O-(2-hydroxy)ethyl-rapamycin, labeled "Ref. Std."

Example 70

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 44±3 μg of polymer. For the reservoir layer, the drug:polymer ratio was 1:2, and the measured average drug content was 245 μg as determined by Example 38. For the barrier layer, the measured average dry weight was 104 μg.

After the coatings were formed on the stents, a select number of stents were tested for the drug release rate from the coatings according to the procedure described in Example 54. It was determined that the average drug released in 24 hours was 23.5 μg, or 9.6% of the total.

Example 71

13 mm PENTA stents were coated by spraying a 2% (w/w) solution of EVOH and 98% (w/w) dimethylacetamide. The solvent was removed by baking at 140° C. for 2 hours. A solution of EVOH and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 45±3 μg of polymer. For the reservoir layer, the drug:polymer ratio was 1:1.5, and the measured average drug content was 337 μg as determined by Example 38. For the barrier layer, the measured average dry weight was 169 μg.

After the coatings were formed on the stents, a select number of stents were tested for the drug release rate from the coatings according to the procedure described in Example 54. It was determined that the average drug released in 24 hours was 37.1 μg, or 11.0% of the total.

Example 72

Figure 14:
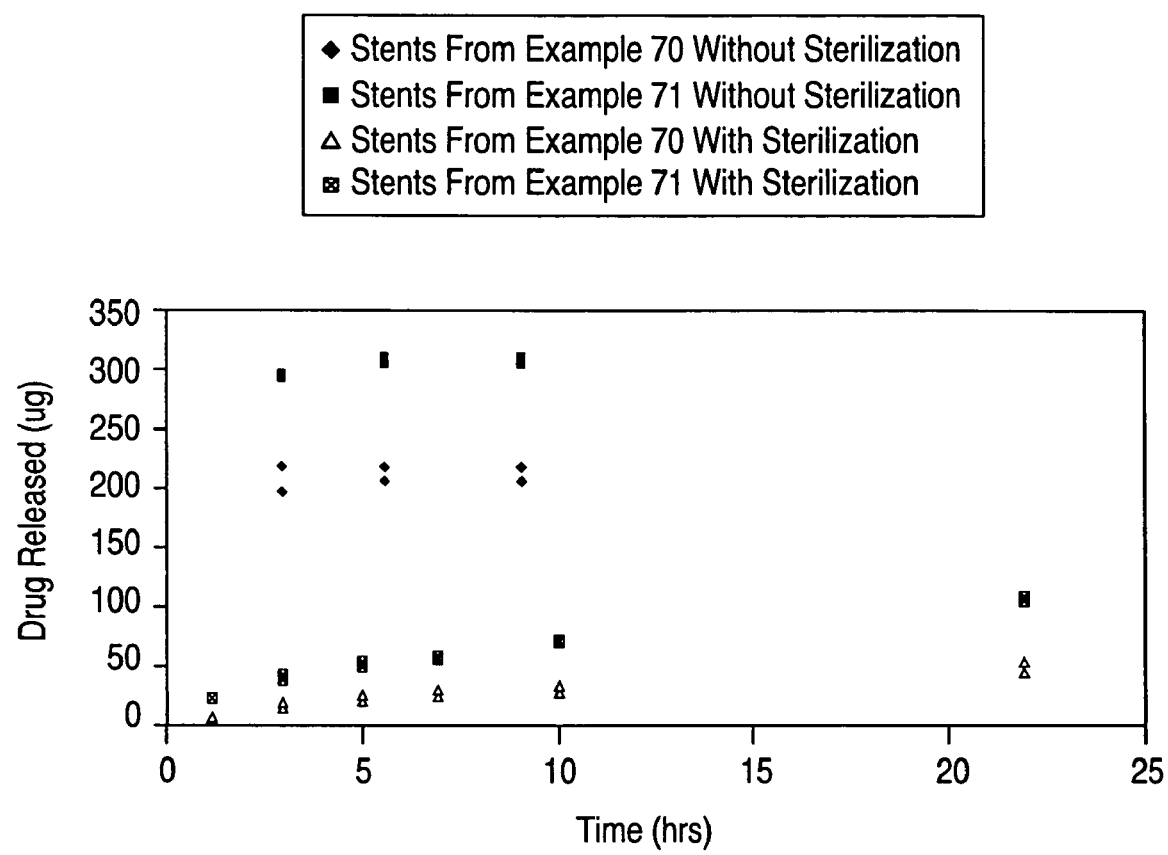
FIG. 14 is a graph showing the release rate of an active agent from stent coatings as referred to in Example 72.

Stents from Example 70 and stents from Example 71 were sterilized according to the process described in Example 68. The released rates of the drug in the stent coatings of sterilized stents and non-sterilized were then tested according to the process described in Example 41. The results of the release rate test are graphically shown in FIG. 14.

Example 73

A 13 mm PENTA stent can be coated by spraying a solution of EVOH, 40-O-(2-hydroxy)ethyl-rapamycin and ethanol onto the stent. The stent is then baked at 50° C. for 2 hours to yield a reservoir coating with 300 μg of EVOH and 300 μg of 40-O-(2-hydroxy)ethyl-rapamycin. A barrier layer can be formed by spraying the stent with a solution of EVOH and pentane. A second 2 hour bake at 50° C. can be performed to remove the solvent to yield a barrier coating with 320 μg of EVOH.

Example 74

A 13 mm PENTA stent can be coated by spraying a solution of EVOH and DMAC onto the stent. The solvent is removed by baking at 140° C. for 2 hours to yield a primer coating with 100 μg of EVOH. A reservoir layer can be applied by spraying a solution of EVOH, 40-O-(2-hydroxy)ethyl-rapamycin and ethanol onto the stent. The stent is then baked at 50° C. for 2 hours to yield a reservoir coating with 200 μg of EVOH and 400 μg of 40-O-(2-hydroxy)ethyl-rapamycin. A barrier layer can be formed by spraying the stent with a solution of EVOH and pentane. A second 2 hour bake at 50° C. is performed to remove the solvent to yield a barrier coating with 350 μg of EVOH.

Example 75

A 13 mm PENTA stent can be coated by spraying a solution of EVOH, 40-O-(2-hydroxy)ethyl-rapamycin and ethanol onto the stent. The stent is then baked at 50° C. for 2 hours to yield a reservoir coating with 500 μg of EVOH and 250 μg of 40-O-(2-hydroxy)ethyl-rapamycin. A barrier layer can be formed by spraying the stent with a solution of EVOH and pentane. A second 2 hour bake at 50° C. is performed to remove the solvent to yield a barrier coating with 300 μg of EVOH.

Example 76

A 13 mm PENTA stent can be coated by spraying a solution of EVOH, 40-O-(2-hydroxy)ethyl-rapamycin and ethanol onto the stent. The stent is then baked at 50° C. for 2 hours to yield a reservoir coating with 475 μg of EVOH and 175 μg of 40-O-(2-hydroxy)ethyl-rapamycin. A barrier layer can be formed by spraying the stent with a solution of EVOH and pentane. A second 2 hour bake at 50° C. is performed to remove the solvent to yield a barrier coating with 300 μg of EVOH.

Example 77

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 400 μg of EVOH and 200 μg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 300 μg of EVOH.

Example 78

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 400 μg of EVOH and 200 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 150 μg of PBMA.

Example 79

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 μg of EVOH and 200 μg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 200 μg of EVOH.

Example 80

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 µg of EVOH and 200 µg of 40-O-(2-hydroxy)ethyl-rapamycin. A barrier layer can formed by spraying the stent with a solution of PBMA and HFE FLUX REMOVER. A second 2 hour bake at 50° C. is performed to remove the solvent to yield a barrier coating with 150 µg of PBMA.

Example 81

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 µg of EVOH and 200 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 200 µg of EVOH.

Example 82

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 µg of EVOH and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 100 µg of PBMA.

Example 83

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 270 µg of EVOH and 150 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 150 µg of EVOH.

Example 84

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 170 µg of EVOH and 150 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 75 µg of PBMA.

Example 85

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 150 µg of EVOH and 150 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 200 µg of EVOH. A finishing layer can then applied by spraying the stent with a solution of EVOH, polyethylene oxide (molecular weight of 17.5 K) ("PEO") and dimethylacetamide. The stent is baked at 50° C. for 2 hours to remove the solvent to yield a finishing coating with 83 µg of EVOH and 17 µg of PEO.

Example 86

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 270 µg of EVOH and 150 µg of 40-O-(2-hydroxy)ethyl-rapamycin. A barrier layer can formed by spraying the stent with a solution of EVOH and a mixture of dimethylacetamide and pentane. A second 2 hour bake at 50° C. is performed to remove the solvent to yield a barrier coating with 150 µg of EVOH. A finishing layer can then applied by spraying the stent with a solution of EVOH, PEO and dimethylacetamide. The stent is baked at 50° C. for 2 hours to remove the solvent to yield a finishing coating with 83 µg of EVOH and 17 µg of PEO.

Example 87

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 µg of EVOH and 200 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 100 µg of EVOH.

Example 88

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 200 µg of EVOH and 200 µg of 40-O-(2-hydroxy)ethyl-rapamycin. A barrier layer can be formed by spraying the stent with a solution of EVOH, KYNAR and HFE FLUX REMOVER. A second 2 hour bake at 50° C. is performed to remove the solvent to yield a barrier coating with 50 µg of EVOH and 50 µg of KYNAR.

Example 89

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 350 µg of EVOH and 200 µg of 40-O-(2-hydroxy)ethyl-rapamycin. A barrier layer is formed by spraying the stent with a solution of EVOH and a mixture of dimethylacetamide and pentane. A second 2 hour bake at 50° C. is performed to remove the solvent to yield a barrier coating with 200 µg of EVOH.

Example 90

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 350 µg of EVOH and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 100 µg of PBMA.

Example 91

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 350 µg of EVOH and 200 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 200 µg of EVOH.

Example 92

An 8 mm PIXEL stent is coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 350 µg of EVOH and 200 µg of 40-O-(2-hydroxy)ethyl-rapamycin. A barrier layer can be formed by spraying the stent with a solution of EVOH and a mixture of dimethylacetamide and pentane. A second 2 hour bake at 50° C. is performed to remove the solvent to yield a barrier coating with 100 µg of EVOH. A finishing layer can then be applied by spraying the stent with a solution of EVOH, PEO and dimethylacetamide. The stent is baked at 50° C. for 2 hours to remove the solvent to yield a finishing coating with 83 µg of EVOH and 17 µg of PEO.

Example 93

An 8 mm PIXEL stent can be coated by spraying a solution of EVOH and 40-O-(2-hydroxy)ethyl-rapamycin in a mixture of dimethylacetamide and ethanol onto the stent. The stent is then baked at 50° C. for 2 hours to yield a reservoir coating with 350 µg of EVOH and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 75 µg of PBMA. A finishing layer can then be applied by spraying the stent with a solution of PBMA, PEO and dimethylacetamide. The stent is baked at 50° C. for 2 hours to remove the solvent to yield a finishing coating with 62.5 µg of PBMA and 12.5 µg of PEO.

Example 94

The purpose of this study was to evaluate 40-O-(2-hydroxy)ethyl-rapamycin in its ability to prevent excessive neointimal proliferation following stenting in a 28-day porcine coronary artery stent model. Specifically, two formulations of 40-O-(2-hydroxy)ethyl-rapamycin and EVOH were coated onto Multi-Link Penta™ stents. These two formulations of drug eluting stents were compared to a polymer control and a bare stent control in terms of safety and efficacy in a 28 day in vivo porcine model.

The following are the materials used for this Example:
1. Experimental animals: Thirteen 30-45 kg Yorkshire cross pigs, male or female.
2. Stents: MULTI-LINK PENTA™ (3.0×13 mm) with the following coatings:
 Six Bare stainless steel stents (Control Group).
 Nine True Coat™ stents (EVOH Polymer Control Group) have 800 µg of EVOH.
 Nine stents having a reservoir layer with 40-O-(2-hydroxy)ethyl-rapamycin (205 µg of drug, with a drug to polymer ratio of 1:1.75) and a 189 µg EVOH topcoat.
 Nine stents having a reservoir layer with 40-O-(2-hydroxy)ethyl-rapamycin (282 µg of drug, with a drug to polymer ratio of 1:1.6) and a 130 µg EVOH topcoat.
3. BMW™ wires 0.014", 190 cm.
4. Guide wire 0.035", 190 cm.
5. Viking guide catheters, 7F.
6. Introducer sheaths (8-10F).
7. ACS 20/20 Indeflator™ Inflation Device.
8. Heparinized saline.
9. Nitroglycerin, Lidocaine, other inotropic/chronotropic drugs.
10. Standard surgical equipment, anesthetic, and medications as necessary.
11. Respiratory and hemodynamic monitoring systems.
12. Positive pressure ventilator and associated breathing circuits.
13. ACT machine and accessories.
14. PTCA accessories.
15. Ambulatory defibrillator.
16. Fluoroscopy equipment.
17. Non-ionic contrast agent.

Thirteen (13) pigs were evaluated in this study. Eleven (11) pigs were used for the 28-day chronic study in order to evaluate the vascular response to the drug eluting stents. Three stents were implanted in each animal. Stents were deployed in the right coronary artery (RCA), the left anterior descending artery (LAD), and the left circumflex coronary artery (LCX) for the 28-day duration. All stents were deployed at a 1.1:1 stent: artery ratio allowing slight to moderate injury in order to assess the drugs ability to prevent excessive neointimal proliferation following stenting. Each stented vessel underwent follow up angiography and histo-pathological evaluation in order to assess the chronic vascular cellular response and to assess if the drug has any effect in reducing neointimal proliferation compared to controls.

Pre-clinical animal testing was performed in accordance with the NIH Guide for the Care and Use of Laboratory Animals. The animals were housed at an animal facility. Animals were shipped off-site for chronic housing once fully recovered from the procedure. All animal care, husbandry, and veterinary issues fell under the responsibility of the institutional veterinarian.

All animals received aspirin (325 mg PO) and Ticlopidine (500 mg PO) once daily for three days prior to undergoing stent placement. All stent placement procedures were performed on anesthetized pigs using aseptic technique. A baseline angiogram was obtained and three target sites (1 per coronary vessel) were selected with 2.7-3.2 mm vessel diameter. Vessel size was determined by using the guiding catheter as a reference or with on line Quantitative Coronary Angiographic analysis (QCA). After selection of a target site, the appropriate products was prepared for use and stents were deployed in such a manner as to achieve a 1.1:1.0 overstretch of the vessel. After recovery from anesthesia, each pig was treated with Ticlopidine (500 mg PO) once daily for the duration of the study and Aspirin (325 mg PO) once daily for the duration of the study.

After 28 days each animal underwent a follow-up angiography in order to re-assess patency, deployment and placement of stents. Additionally, online QCA measurements were made to provide angiographic estimates of the minimal luminal diameters (MLD) and percentage of vessel lumen restenosis. All follow-up angiography procedures were performed on anesthetized pigs using clean technique. Aseptic technique was not necessary as this is an acute procedure.

The pigs were euthanized immediately following the follow-up angiography. The hearts were removed, perfused with saline and pressure perfusion fixed with formalin before being placed into a labeled container with formalin and submitted for pathological evaluation. Sections of the treated coronary arteries were sent to a contracted pathology site. Five cross sections of the stented vessel were prepared including one section of each vessel ends and three sections of the stented area. The tissue was stained with haemoatoxylin and eosin and with an elastin stain. A morphometric analysis of the stented arteries was performed which included an assessment of stent strut position and determination of vessel/lumen areas, percent stenosis, injury scores, intimal and medial areas and intima/media ratios.

The following is a list of the general procedure used for this Example:

A. Animal Preparation
1. Administer Aspirin (325 mg PO) and Ticlopidine (500 mg PO) once daily starting 3 days prior to stent implantation.
2. Sedate the pigs according to the institutional standard operating procedure.
3. Intubate the trachea via an oral approach.
4. Deliver isoflurane (up to 5%) to achieve and maintain an adequate plane of anesthesia.
5. Shave the sheath introduction area free of hair and scrub the surgical site with surgical soap and/or antiseptic solution.
6. Place a 8-10F introducer sheath into the right or left femoral artery.
7. Obtain an arterial blood sample for a baseline ACT.
8. Record rectal temperature.
9. Administer heparin 200 units/kg IV (not to exceed 100,000 units) and obtain a blood sample for measurement of ACT 5-10 minutes later.
10. Repeat heparin as needed to maintain ACT≧300 seconds.
11. Measure and record arterial blood pressure, heart rate and electrocardiogram (ECG).

B. Angiography for vessel selection
1. Advance the guiding catheter over the guidewire into the aortic arch and cannulate the desired vessel.
2. Administer nitroglycerin 200 µg intra-luminally prior to baseline angiography.
3. Perform baseline angiogram and record images on cine.
4. With the diameter of the guiding catheter as a reference, select vasculature that will allow a target stent to artery ratio of 1.1:1.0.

C. Stent Preparation and Deployment
1. Perform online QCA and measure baseline proximal, target, and distal reference sites.
2. Administer nitroglycerin (200 µg) intra-luminally prior to stent deployment, then as needed to control coronary artery vasospasm.
3. Inspect the stent delivery system. Ensure that the stent is correctly positioned on the balloon. Inspect the stent for any abnormalities.
4. Flush guidewire lumen with heparinized saline until fluid exits the guidewire notch.
5. Prepare Indeflator/syringe with diluted (approximately 50:50) contrast medium.
6. Attach syringe to test catheter inflation port; use standard techniques to fill the inflation lumen with diluted contrast.
7. Purge syringe and test catheter inflation lumen of all air.
8. Purge Indeflator of all air and attach to test catheter inflation port.
9. Position an appropriate guidewire in the distal bed of the target artery.
10. Insert the stent delivery system through the guiding catheter over the guidewire.
11. Advance the stent delivery system to the pre-selected arterial deployment site.
12. Position balloon for inflation.
13. Refer to IFU for inflation strategy. If no IFU available, inflate the balloon at a slow steady rate to a pressure that expands the stent to the desired diameter. Hold at this pressure for 30 seconds.
14. Record inflated balloon by pulling image on cine. Perform on-line QCA and measure the inflated balloon diameter.
15. Deflate balloon by pulling negative pressure. While withdrawing the system, observe tactually and fluoroscopically. Record any resistance.
16. Administer nitroglycerin (200 µg) intra-luminally.
17. Assess patency, deployment, and placement of stent via coronary angiography.
18. Assess TIMI angiographic low grade.
19. Record on cine and video.
20. Measure post-proximal, target, and distal MLD with QCA.
21. Repeat Section C with remaining stent delivery systems.
22. Measure and record heart rate, arterial blood pressure and electrocardiogram (ECG).

D. Stent Procedure End
1. Remove the guidewire, guiding catheter and introducer sheath.
2. Remove introducer sheath from the femoral artery.
3. Ligate the artery with 3-0 suture material at the side of sheath entry.
4. Appose the muscular and subcutaneous tissue layer using suture material.
5. Allow the animal to recover from anesthesia in an individual cage.
6. Give Buprenorphine (0.05 mg/kg) PRN as needed for pain.
7. Administer Ticlopidine (250 mg PO) and aspirin (325 mg PO) once daily until date of follow-up angiography.

E. Follow-up Angiography for 28-day study pigs
1. Following an overnight fast, sedate the pigs according to the institutional standard operating procedure.
2. Intubate the trachea via an oral approach.
3. Deliver isoflurane at a concentration up to 5% as needed to maintain surgical plane of anesthesia.
4. Shave the cut-down area free of hair and scrub the surgical site with surgical soap and/or antiseptic solution.

5. Measure and record arterial blood pressure, heart rate and electrocardiogram (ECG).
6. Record animal number and study identification tag on cine.
7. Advance the guiding catheter over a guidewire to cannulate the ascending aorta to appropriate vessel.
8. Administer nitroglycerine (200 µg IC) prior to angiography.
9. Perform an angiogram. Record images on cine and video (if available).
10. Assess patency, deployment and placement of stents via angiography.
11. Obtain online QCA measurements to record the proximal and distal reference vessel diameters and the minimal luminal diameters (MLD).
12. Give TIMI scores.

F. Procedure End

1. Remove the guiding catheter and introducer sheath.
2. Euthanize the animal with an overdose of barbiturates and/or potassium chloride.
3. Remove the heart and all arteries containing the implanted stents.
4. Perfusion fix the heart and other implanted vessels by infusing 250 ml of Lactated Ringers solution or physiologic saline followed by approximately 0.5-1.0 liters of formalin under a pressure of approximately 100 mmHg.
5. Place heart into labeled container with formalin solution for gross and microscopic examination of heart and implanted vasculature.

The percent mean stenosis and percent mean neointimal area for the different groups were calculated. The following Table 13 demonstrates that both of the formulations of the drug eluting stents having 40-O-(2-hydroxy)ethyl-rapamycin significantly reduced the percent stenosis and percent mean neointimal area as compared to the control groups.

TABLE 13

| Treatment Group | Percent Mean Stenosis | Standard Deviation | Percent Mean Neointimal Area | Standard Deviation |
|---|---|---|---|---|
| Bare Stent | 29.54 | 14.86 | 2.37 | 1.06 |
| EVOH Control | 37.54 | 10.62 | 3.00 | 0.64 |
| Formulation 1 | 20.67 | 4.79 | 1.64 | 0.35 |
| Formulation 2 | 24.29 | 9.75 | 1.85 | 0.38 |

Example 95

13 mm PIXEL-D stents were coated by spraying a 2% (w/w) solution of EVOH and 98% (w/w) dimethylacetamide. The solvent was removed by baking at 140° C. for 2 hours. The target primer layer weight was 58.2 µg. For the reservoir layer, a solution of EVOH and actinomycin D in a mixture of 75% (w/w) dimethylacetamide and 25% (w/w) ethanol was spray coated onto the stents. The ratio of EVOH to actinomycin D was 9 to 1. The stents were then baked at 50° C. for 2 hours. The target weight for the reservoir layer was 90 µg. A barrier layer was formed by spraying the stents with a solution of EVOH in a mixture of 80% (w/w) dimethylacetamide and 20% (w/w) pentane. Another 2 hour bake at 50° C. was performed to remove the solvent. The target weight for the barrier layer was 218 µg.

After the solvent had been substantially removed and the coatings had been formed, a select number of stents were then subjected to a standard grip process in order to mount the stent onto a catheter. The stents were separated into four test groups. Group 1 served as the control group and were mounted at room temperature; Group 2 was exposed to a temperature of about 82.2° C. (180° F.) for about 2 minutes; Group 3 was exposed to a temperature of about 93.3° C. (200° F.) for about 2 minutes; and Group 4 was exposed to a temperature of about 121.1° C. (250° F.) for about 2 minutes.

Five stents from each group were tested to determine if the total content of the active agent was affected by the thermal treatment. The results demonstrated that the thermal treatment process did not affect the total content. The results for the total drug content test are shown in Table 14.

TABLE 14

| | Mean Total Content (µg) | Standard Deviation (µg) |
|---|---|---|
| Control | 104 | 3.4 |
| Group 1 (82.2° C.) | 105 | 10.1 |
| Group 2 (93.3° C.) | 105 | 7.2 |
| Group 3 (121.1° C.) | 107 | 2.7 |

Ten stents from each group were then tested to determine the release rate of the active agent in a 24 hour period. The results demonstrated that the thermal treatment process decreased the mean release rate for a 24 hour period. Additionally, the thermal treatment process decreased the standard deviation. The results for the release rate test are shown in Table 15.

TABLE 15

| | Mean Release Rate (µg/24 hours) | Standard Deviation (µg) |
|---|---|---|
| Control | 33.1 | 12.4 |
| Group 1 (82.2° C.) | 28.5 | 7.3 |
| Group 2 (93.3° C.) | 19.2 | 9.6 |
| Group 3 (121.1° C.) | 21.9 | 4.0 |

Example 96

13 mm PIXEL-D stents were coated by spraying a 2% (w/w) solution of EVOH and 98% (w/w) dimethylacetamide. The solvent was removed by baking at 140° C. for 2 hours. The target primer layer weight was 40 µg. For the reservoir layer, a solution of EVOH and actinomycin D in a mixture of 75% (w/w) dimethylacetamide and 25% (w/w) ethanol was spray coated onto the stents. The ratio of EVOH to actinomycin D was 9 to 1, and a target total dose of 7.9 µg. The stents were then baked at 50° C. for 2 hours. The target weight for the reservoir layer was 79 µg. A barrier layer was formed by spraying the stents with a solution of EVOH in a mixture of 80% (w/w) dimethylacetamide and 20% (w/w) pentane. Another 2 hour bake at 50° C. was performed to remove the solvent. The target weight for the barrier layer was 135 µg.

After the solvent had been substantially removed and the coatings had been formed, a select number of stents were then subjected to different thermal treatment processes. One process included subjecting stents to a two hour thermal treatment before the mounting process. In particular, a select number of coated stents were placed in a convection oven and subjected to a temperature of about 80° C. for about 2 hours. The other process included subjecting stents to a two minute thermal treatment during the mounting procedure. In particular, Group 1 was the control group and was mounted at room temperature; Group 2 was exposed to a temperature of about 82.2° C. (180° F.) for about 2 minutes; and Group 3 was exposed to a temperature of about 121.1° C. (250° F.) for about 2 minutes. Table 16 shows the number of stents used in each of the test groups.

TABLE 16

| Temperature during Stent Mounting Process | Two Hour Thermal Treatment Process | Without Two Hour Thermal Treatment Process |
|---|---|---|
| Control (Room Temperature) | 10 | 10 |
| Group 1 (82.2° C.) | 10 | 10 |
| Group 2 (121.1° C.) | 15 | 15 |

Stents from Group 2, including stents from the two hour treatment group and the non-two hour treatment group, were tested to determine if the total content of the active agent was affected by the two hour thermal treatment process. The results demonstrated that the thermal treatment process did not affect the total content. In particular, the average total content for the stents that were subjected to the two hour treatment was 9.3 µg/cm$^2$±0.6, whereas the average total content for the stents that were not subjected to the two hour treatment was 8.8 µg/cm$^2$±0.6.

A select number of stents from each group were then tested to determine the release rate of the active agent in a 24 hour period. The results demonstrated that both thermal treatment processes decreased the mean release rate for a 24 hour period. The results for the release rate tests are shown in Table 17.

TABLE 17

| | Mean Release Rate (µg/24 hours) and Standard Deviation | |
|---|---|---|
| Temperature during Stent Mounting Process | Two Hour Thermal Treatment Process | Without Two Hour Thermal Treatment Process |
| Control (Room Temperature) | 17.8 ± 4.8 | 37.0 ± 11.2 |
| Group 1 (82.2° C.) | 21.2 ± 9.0 | 28.1 ± 9.0 |
| Group 2 (121.1° C.) | 9.0 ± 2.7 | 10.2 ± 1.9 |

Example 97

13 mm PIXEL-D stents were coated by spraying a 2% (w/w) solution of EVOH and 98% (w/w) dimethylacetamide. The solvent was removed by baking at 140° C. for 2 hours. For the reservoir layer, a solution of EVOH and actinomycin D in a mixture of 75% (w/w) dimethylacetamide and 25% (w/w) ethanol was spray coated onto the stents. The ratio of EVOH to actinomycin D was 9 to 1. The stents were then baked at 50° C. for 2 hours. A barrier layer was formed by spraying the stents with a solution of EVOH in a mixture of 80% (w/w) dimethylacetamide and 20% (w/w) pentane. Another 2 hour bake at 50° C. was performed to remove the solvent.

After the solvent had been substantially removed and the coatings had been formed, the stents were then subjected to various thermal treatment and storage conditions. In particular, test groups were subjected to different conditions to study the effect of (1) exposure temperatures (40° C., 50° C. or 80° C.); (2) exposure time (2 or 7 hours); and (3) storage time (0 or 30 days). Table 18 summarizes the different test parameters.

TABLE 18

| Group | Exposure Temperature (° C.) | Exposure Time (Hours) | Storage Time at 25° C. (Days) |
|---|---|---|---|
| A0 | Room Temperature | N/A | 0 |
| A1 | 40 | 2 | 0 |
| A2 | 40 | 7 | 0 |
| A3 | 50 | 2 | 0 |
| A4 | 50 | 7 | 0 |
| A5 | 80 | 2 | 0 |
| A6 | 80 | 7 | 0 |
| B1 | 50 | 2 | 30 |
| B2 | 50 | 7 | 30 |
| B3 | 80 | 2 | 30 |
| B4 | 80 | 7 | 30 |

After the stents were exposed to the thermal treatment, the stents were sterilized using an e-beam process. During the e-beam process, the stents were exposed to 35 kGy of radiation using a one pass process.

Five stents from each group were tested to determine if the total content of the active agent was affected by the thermal treatment. Ten stents from each group were then tested to determine the release rate of the active agent in a 24 hour period. The results demonstrated that the thermal treatment process did not affect the total content. The results also demonstrated that the thermal treatment process decreased the mean release rate for a 24 hour period. The results for the total content and release rate test are shown in Table 19.

TABLE 19

| Group | Exposure Temperature (° C.) | Exposure Time (hours) | Storage Time at 25° C. (Days) | Release Rate (%/24 hours) | Total Content (% of target concentration) |
|---|---|---|---|---|---|
| A0 | | Control | | 16.2 ± 2.0 | 91.2 ± 1.9 |
| A1 | 40 | 2 | 0 | 14.9 ± 4.6 | 96.6 ± 5.5 |
| A2 | 40 | 7 | 0 | 15.0 ± 6.0 | 83.6 ± 6.9 |
| A3 | 50 | 2 | 0 | 15.5 ± 3.4 | 89.2 ± 8.2 |
| A4 | 50 | 7 | 0 | 19.3 ± 4.1 | 87.2 ± 6.1 |
| A5 | 80 | 2 | 0 | 9.1 ± 2.9 | 87.7 ± 12.8 |
| A6 | 80 | 7 | 0 | 7.6 ± 1.1 | 96.9 ± 8.7 |
| B1 | 50 | 2 | 30 | 20.4 ± 3.0 | 94.4 ± 8.3 |
| B2 | 50 | 7 | 30 | 19.7 ± 4.2 | 87.6 ± 2.3 |

TABLE 19-continued

| Group | Exposure Temperature (° C.) | Exposure Time (hours) | Storage Time at 25° C. (Days) | Release Rate (%/24 hours) | Total Content (% of target concentration) |
|---|---|---|---|---|---|
| B3 | 80 | 2 | 30 | 11.5 ± 1.8 | 78.7 ± 8.0 |
| B4 | 80 | 7 | 30 | 10.1 ± 2.2 | 89.9 ± 3.5 |

Example 98

DLPLA for this Example was provided by Birmingham Polymers, Inc., 756 Tom Martin Drive, Birmingham, Ala. 35211-4467 (Manufacture Lot # DO1O78). According to the manufacture, the DLPLA has an inherent viscosity of 0.55-0.75, a $T_g$ of 55° C.-60° C., and lacks a $T_m$ (i.e., is amorphous). The viscosity was tested and was determined to be 0.67 dL/g in $CHCl_3$.

13 mm Penta stents (available from Guidant) were coated by spraying a solution having 1% (w/w) DLPLA, 1% (w/w) everolimus, 78.4% (w/w) 1,1,2-trichloroethane and 19.6% (w/w) chloroform. The apparatus used to coat the stents for this Example and Examples 99-102 was an EFD 780S spray device with VALVEMATE 7040 control system (manufactured by EFD Inc., East Providence, R.I.). The solvent was removed by baking at about 120° C. for about 1 hour. The target drug coating weight after removal of the solvent was 300 μg. The stents were then sterilized using an e-beam process set at 35 KGy.

Example 99

13 mm Penta stents were coated by spraying a 2% (w/v) solution of DLPLA (0.36 dL/g in $CHCl_3$), 76.8% (w/w) 1,1,2-trichloroethane and 19.2% (w/w) chloroform. The solvent was removed and the coating was heat treated by baking at about 120° C. for about 1 hour. It is estimated that the solvent was removed from the composition at this temperature after about 30 minutes of exposure. The temperature for the thermal treatment for this Example and for Examples 100-102 was selected to be above the $T_m$ of any blocks of DPLA or LPLA existing in the primer polymer. The target primer layer weight after removal of the solvent was 100 μg.

For the reservoir layer, a solution of 1% (w/w) DLPLA (0.67 dL/g in $CHCl_3$), 1% (w/w) everolimus, 76.8% (w/w) 1,1,2-trichloroethane and 19.2% (w/w) chloroform was spray coated onto the stents. The stents were then baked at about 50° C. for about 1 hour. The target weight for the reservoir layer after removal of the solvent was 300 μg. The stents were then sterilized using an e-beam process set at 35 KGy.

Example 100

13 mm Penta stents were coated by spraying a 2% (w/w) solution of DLPLA (0.36 dL/g in $CHCl_3$) and 78.4% (w/w) 1,1,2-trichloroethane and 19.6% (w/w) chloroform. The solvent was removed and the coating was heat treated by baking at about 120° C. for about 1 hour. The target primer layer weight after removal of the solvent was 100 μg.

For the reservoir layer, a solution of 1% (w/w) DLPLA (0.67 dL/g in $CHCl_3$), 1% (w/w) everolimus, 76.8% (w/w) 1,1,2-trichloroethane and 19.2% (w/w) chloroform was spray coated onto the stents. The stents were then baked at about 50° C. for about 1 hour. The target weight for the reservoir layer after removal of the solvent was 300 μg.

A barrier layer was formed by spraying the stents with a solution of 2% (w/w) POLYACTIVE in a mixture of 78.4% (w/w) 1,1,2-trichloroethane and 19.6% (w/w) chloroform. POLYACTIVE is a trade name of a family of poly(ethylene glycol)-block-poly(butyleneterephthalate)-block poly(ethylene glycol) copolymers (PEG-PBT-PEG) and is available from IsoTis Corp. of Holland As indicated by the manufacturer, the grade of POLYACTIVE used for this Example and Example 102 had about 45 molar % units derived from PBT and about 55 molar % units derived from PEG. The molecular weight of the PEG units was indicated to be about 300 Daltons. A 1 hour bake at 50° C. was performed to remove the solvent. The target weight for the barrier layer after removal of the solvent was 150 μg. The stents were then sterilized using an e-beam process set at 35 KGy.

Example 101

13 mm Penta stents were coated by spraying a 2% (w/w) solution of DLPLA (0.67 dL/g in $CHCl_3$) and 78.4% (w/w) 1,1,2-trichloroethane and 19.6% (w/w) chloroform. The solvent was removed and the coating was heat treated by baking at about 120° C. for about 1 hour. The target primer layer weight after removal of the solvent was 100 μg.

For the reservoir layer, a solution of 1% (w/w) DLPLA (0.67 dL/g in $CHCl_3$), 1% (w/w) everolimus, 76.8% (w/w) 1,1,2-trichloroethane, and 19.2% (w/w) chloroform was spray coated onto the stents. The stents were then baked at about 50° C. for about 1 hour. The target weight for the reservoir layer after removal of the solvent was 300 μg. The stents were then sterilized using an e-beam process set at 35 KGy.

Example 102

13 mm Penta stents were coated by spraying a 2% (w/w) solution of DLPLA (0.67 dL/g in $CHCl_3$) and 78.4% (w/w) 1,1,2-trichloroethane and 19.6% (w/w) chloroform. The solvent was removed and the coating was heat treated by baking at about 120° C. for about 1 hour. The target primer layer weight after removal of the solvent was 100 μg.

For the reservoir layer, a solution of 1% (w/w) DLPLA (0.67 dL/g in $CHCl_3$), 1% everolimus, 76.8% (w/w) 1,1,2-trichloroethane and 19.2% (w/w) chloroform was spray coated onto the stents. The stents were then baked at about 50° C. for about 1 hour. The target weight for the reservoir layer after removal of the solvent was 300 μg.

A barrier layer was formed by spraying the stents with a solution of 2% (w/w) POLYACTIVE in a mixture of 78.4% (w/w) 1,1,2-trichloroethane and 19.6% (w/w) chloroform. Another 1 hour bake at 50° C. was performed to remove the solvent. The target weight for the barrier layer after removal of the solvent was 150 μg. The stents were then sterilized using an e-beam process set at 35 KGy.

Example 103

Sample stents from Examples 98-102 were subjected to a wet expansion test to determine the mechanical integrity of the coatings. The following procedure was used to determine the mechanical integrity of the coatings for each stent.

The stent was mounted on a balloon catheter. The stent and the balloon were placed in a beaker containing de-ionized water at about 37° C. To deploy the stent, a pressure of about 8 atm was applied to a balloon for about 1 minute. The stent-catheter assembly was then taken out from the beaker, followed by deflating of the balloon and the retraction of the catheter. After the catheter was retracted, the stent was detached from the catheter and dried in air at room temperature for at least eight hours (i.e., over night) before the coating was studied for defects. The stent coating was observed by using a scanning electron microscope (SEM).

Figure 15:
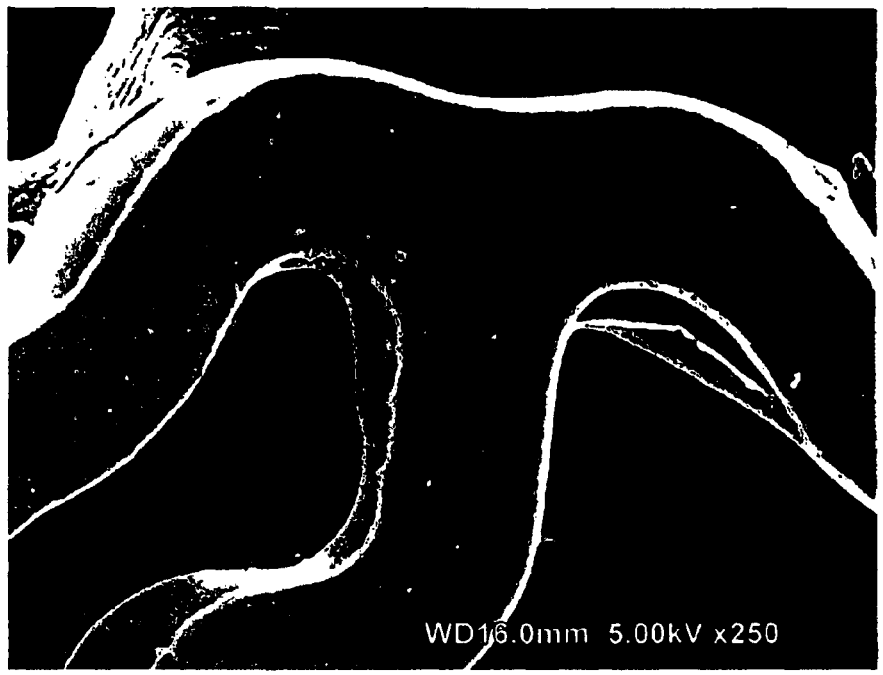
FIGS. 15-19 are photographs as referred to in Example 103.
Figure 16:
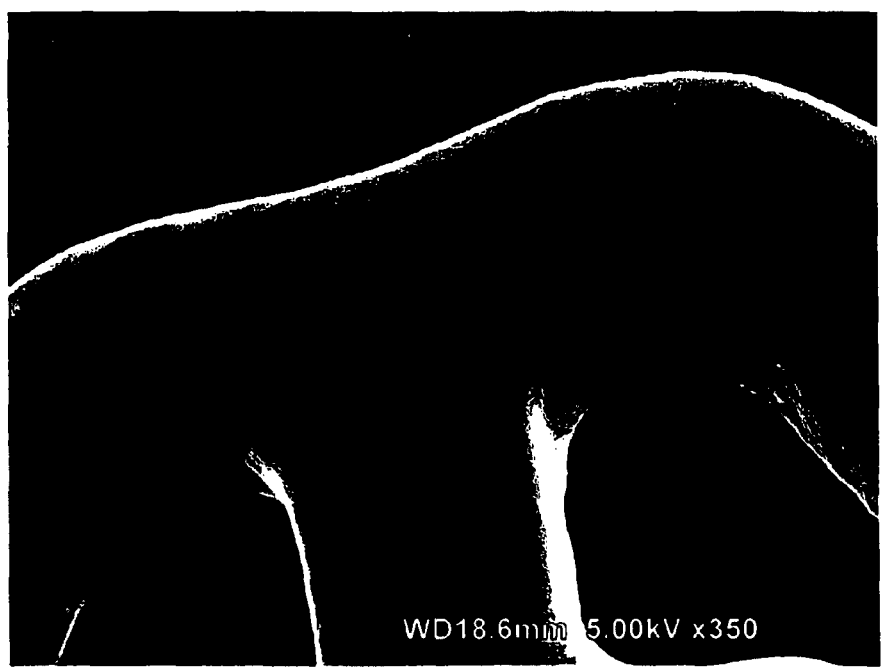
Figure 17:
Figure 18:
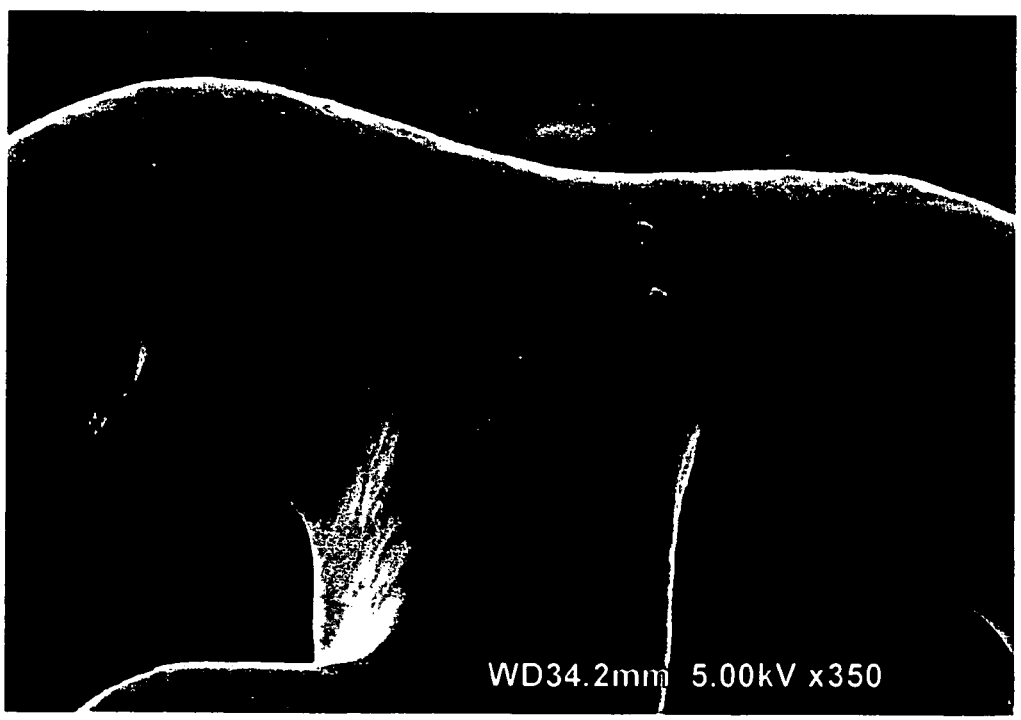
Figure 19:
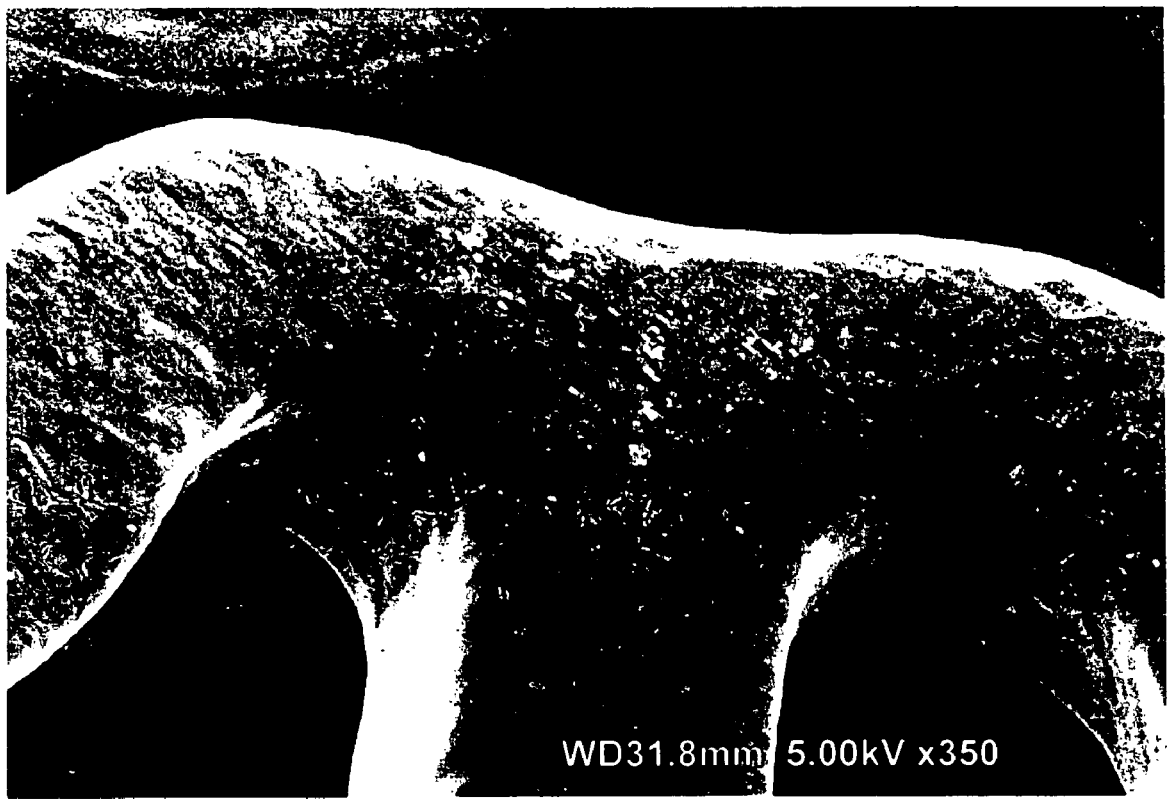

FIGS. 15-19 are SEM photographs of representative stent coatings. FIG. 15 provides illustrative results from the stents of Example 98, and shows polymer peeling at the high strain area of the stent structure. FIG. 16 provides illustrative results from the stents of Example 99, and shows a smooth surface with no cracking or other damage at the high strain area of the stent structure. FIG. 17 provides illustrative results from the stents of Example 100, and shows a smooth surface with no cracking or other damage at the high strain area of the stent structure. FIG. 18 provides illustrative results from the stents of Example 101, and shows a smooth surface with no cracking or other damage at the high strain area of the stent structure. FIG. 19 provides illustrative results from the stents of Example 102, and shows a smooth surface with no cracking or other damage at the high strain area of the stent structure.

It was found that the combination of a primer and a thermal treatment process improved the mechanical properties of the stent coatings. For example, comparing FIG. 15 with FIGS. 16-19 shows that the thermal treatment process improve the adhesion of the coatings to the surface of the stent.

Example 104

A solution containing DLPLA and acetone was applied to stainless steel stents using a controlled deposition system. After the solution was applied, the stents were allowed to dry at room temperature. The target weight for the coating after removal of the solvent was 200 μg. The stents were then sterilized using an e-beam process set at 25 KGy.

Example 105

A solution containing everolimus/DLPLA (1:1) was applied to stainless steel stents using a controlled deposition system. After the solution was applied, the stents were allowed to dry at room temperature. The target weight for the drug coating after removal of the solvent was 400 μg. The stents were then sterilized using an e-beam process set at 25 KGy.

Example 106

A solution containing DLPLA and acetone was applied to Vision™ stents (available from Guidant) using a spray coating system. After the solution was applied, the stents were heat treated at 50° C. for 2 hours. The target weight for the coating after removal of the solvent was 200 μg. The stents were then sterilized using an e-beam process set at 25 KGy.

Example 107

A solution containing everolimus/DLPLA (1:1) and acetone was applied to Vision™ stents using a spray coating system. After the solution was applied, the stents were heat treated at 50° C. for 2 hours. The target weight for the drug coating after removal of the solvent was 400 μg. The stents were then sterilized using an e-beam process set at 25 KGy.

Example 108

Stents from Examples 104-107 were subjected to dry expanded, wet expanded or simulated use testing. It was found that the coatings of Examples 106 and 107 had fewer coating defects than Examples 104 and 105. This finding indicates that the thermal treatment of the coatings improved the mechanical properties of the coatings.

Example 109

A DSC apparatus was used to study the thermal properties of DLPLA pellets and polymeric coatings that included DLPLA. In particular, a Mettler-Toledo 822e DSC equipped with an Intracooler (−70° C.) and STARe software with ISOStep (modulated DSC) was used for this Example. For the experiments on polymeric coatings (as disposed on stents), the stents were flattened longitudinally and folded into a zigzag pattern in order for the expanded stents to fit into the DSC pans.

Figure 20:
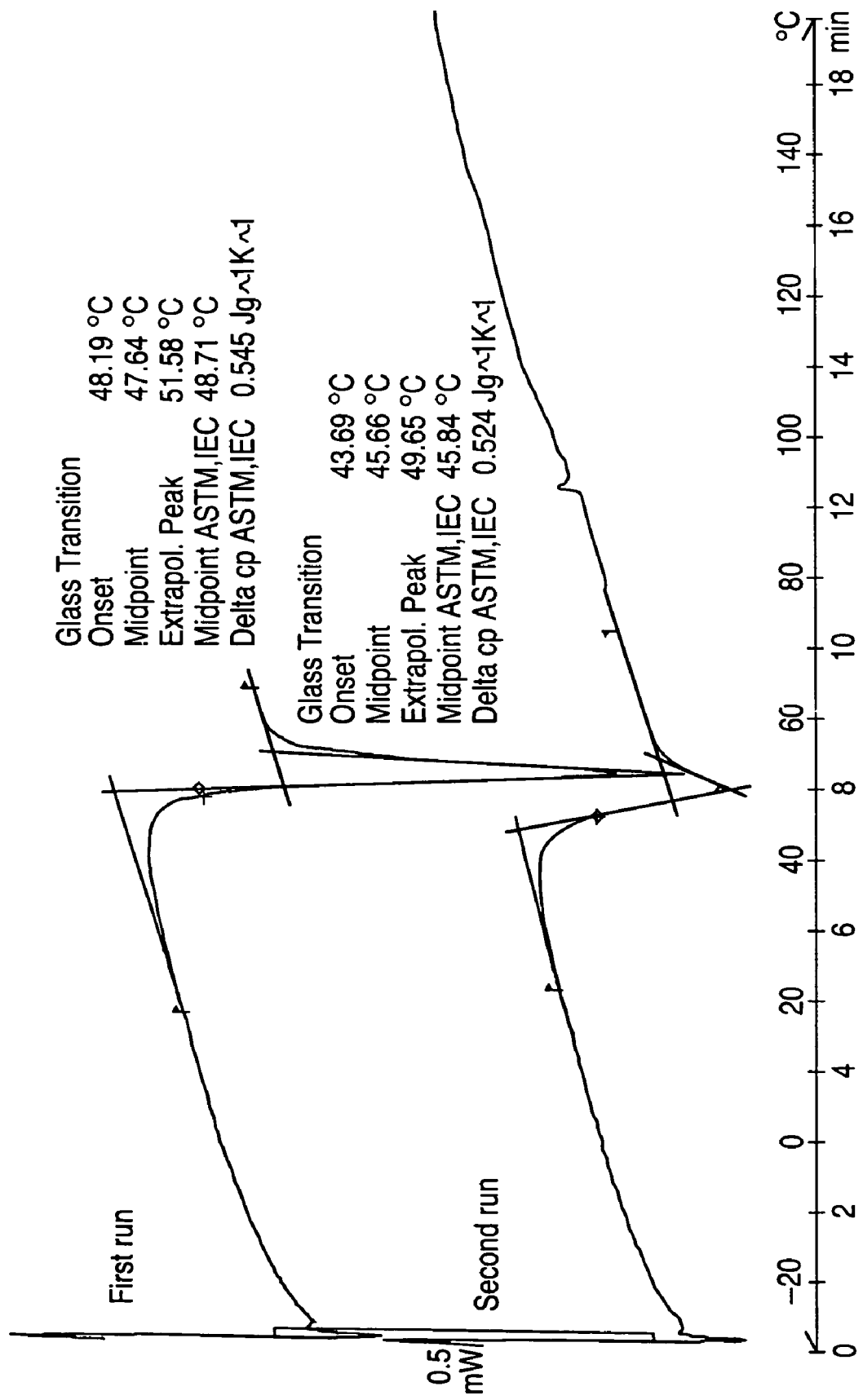
FIGS. 20-24 are graphs as referred to in Example 109.

First, the thermal properties of DLPLA pellets were studied using the above mentioned DSC for two runs. As illustrated in FIG. 20, the pellets exhibited a $T_g$ of about 46° C.

A stainless steel stent was provided ("Stent A"). A coating was formed on a stainless steel stent by applying a DLPLA and acetone solution to the stent using a controlled deposition system ("Stent B"). The solution was allowed to dry at room temperature for 48 to 96 hours.

A coating was formed on another stainless steel stent by applying an everolimus/DLPLA and acetone solution to the stent using a controlled deposition system ("Stent C"). The solution was allowed to dry at room temperature for 48 to 96 hours.

Figure 21:
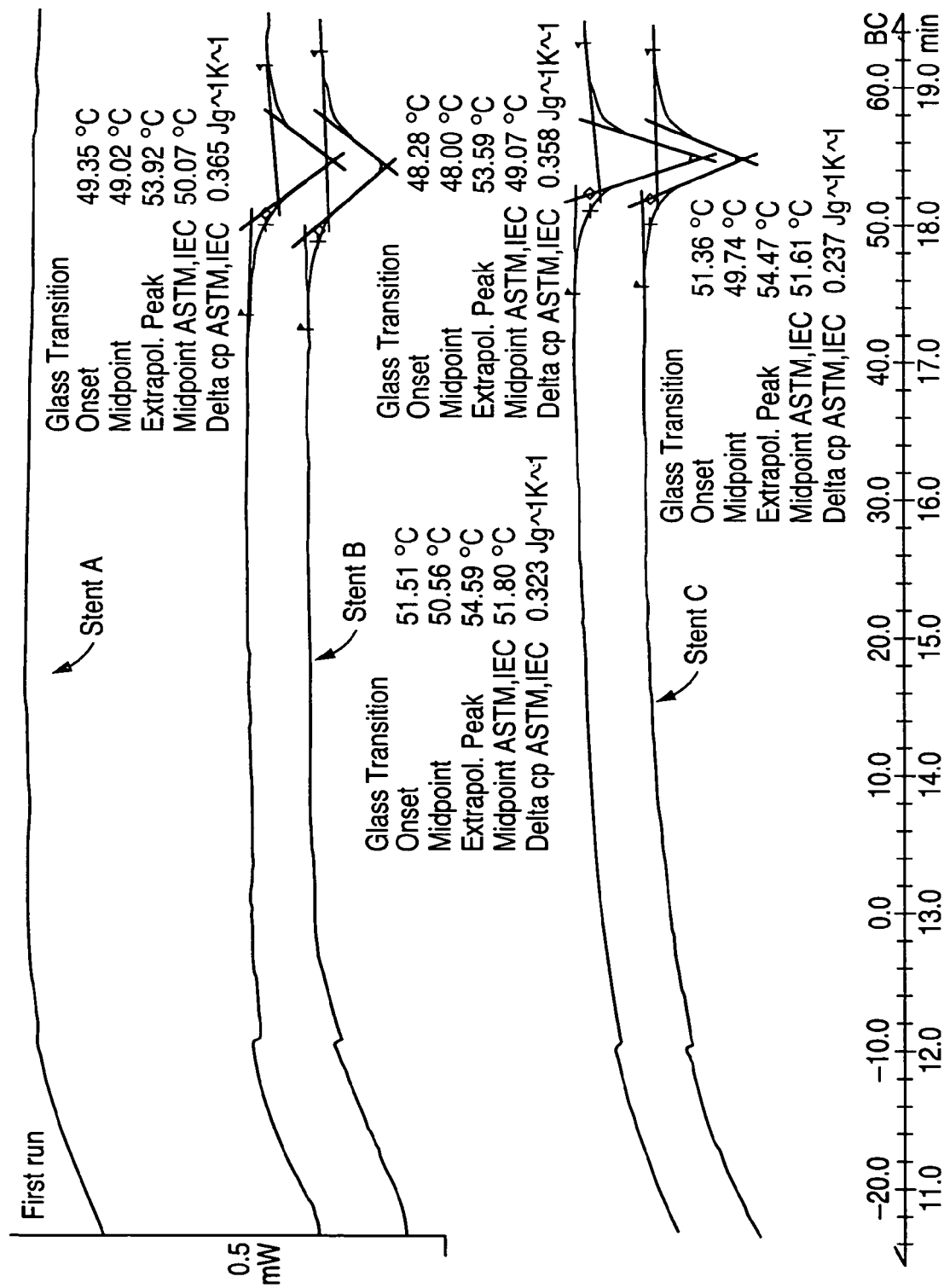
Figure 22:
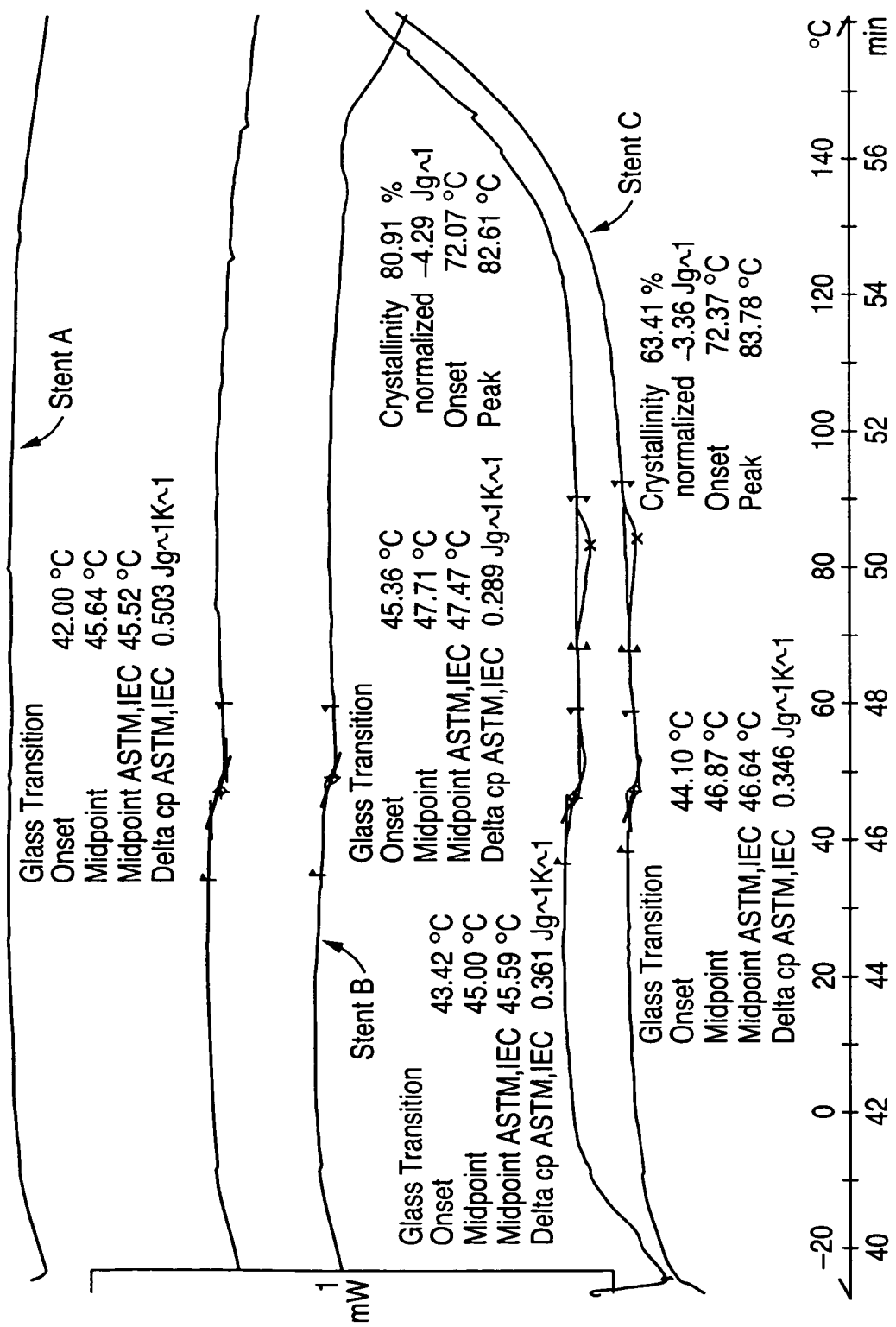

Stents A, B and C were studied using the above mentioned DSC for two runs. During the first run, the samples were heated slightly above the $T_g$ of the polymeric component to remove the relaxation peak. The results from the first run are illustrated in FIG. 21. During the second run, as shown illustrated in FIG. 22, the polymeric coatings of both Stent B and Stent C exhibited a $T_g$ for the polymer at about 46° C. The $T_m$ of the drug was shown to be about 83° C.

Figure 23:
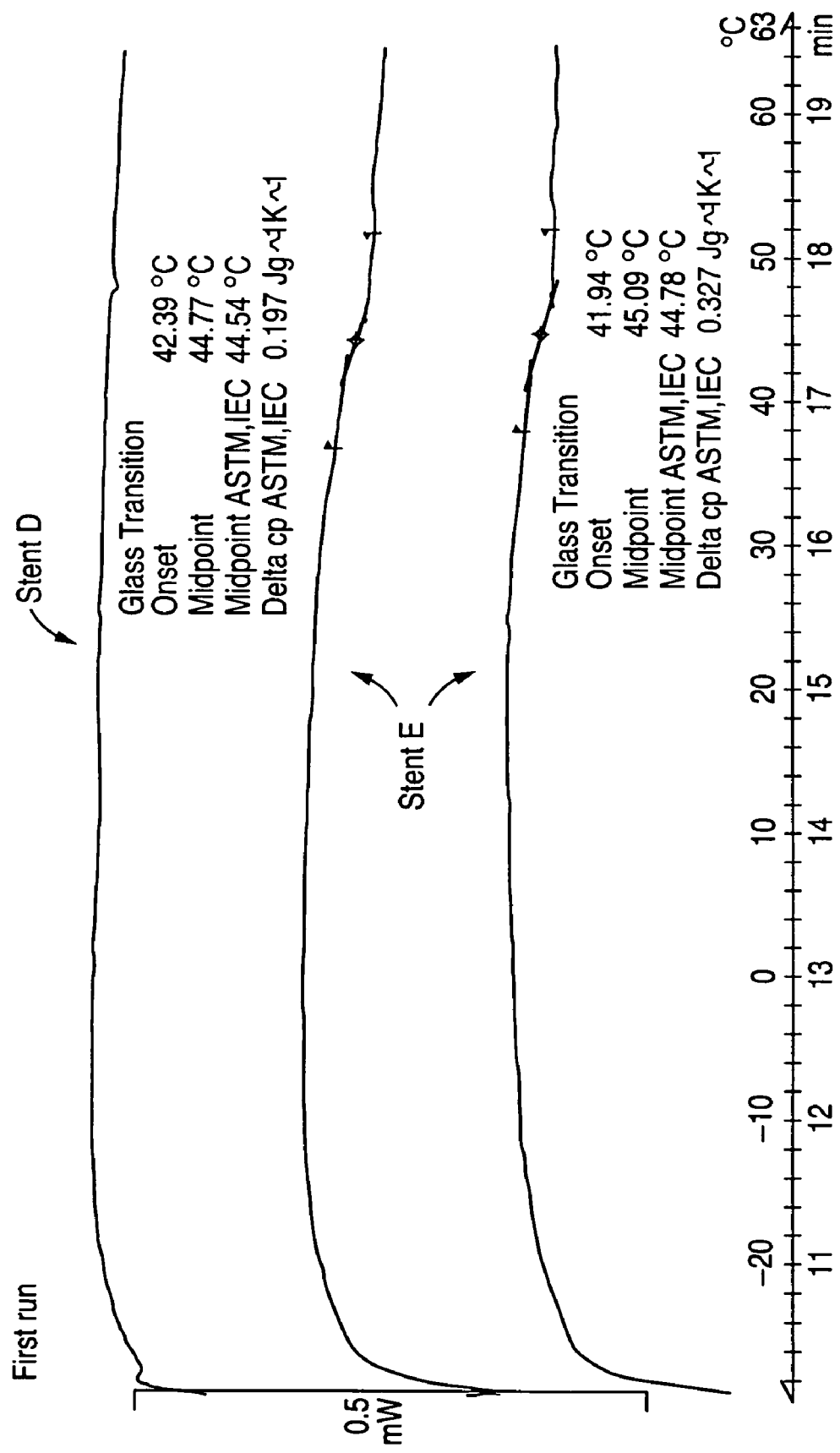
Figure 24:
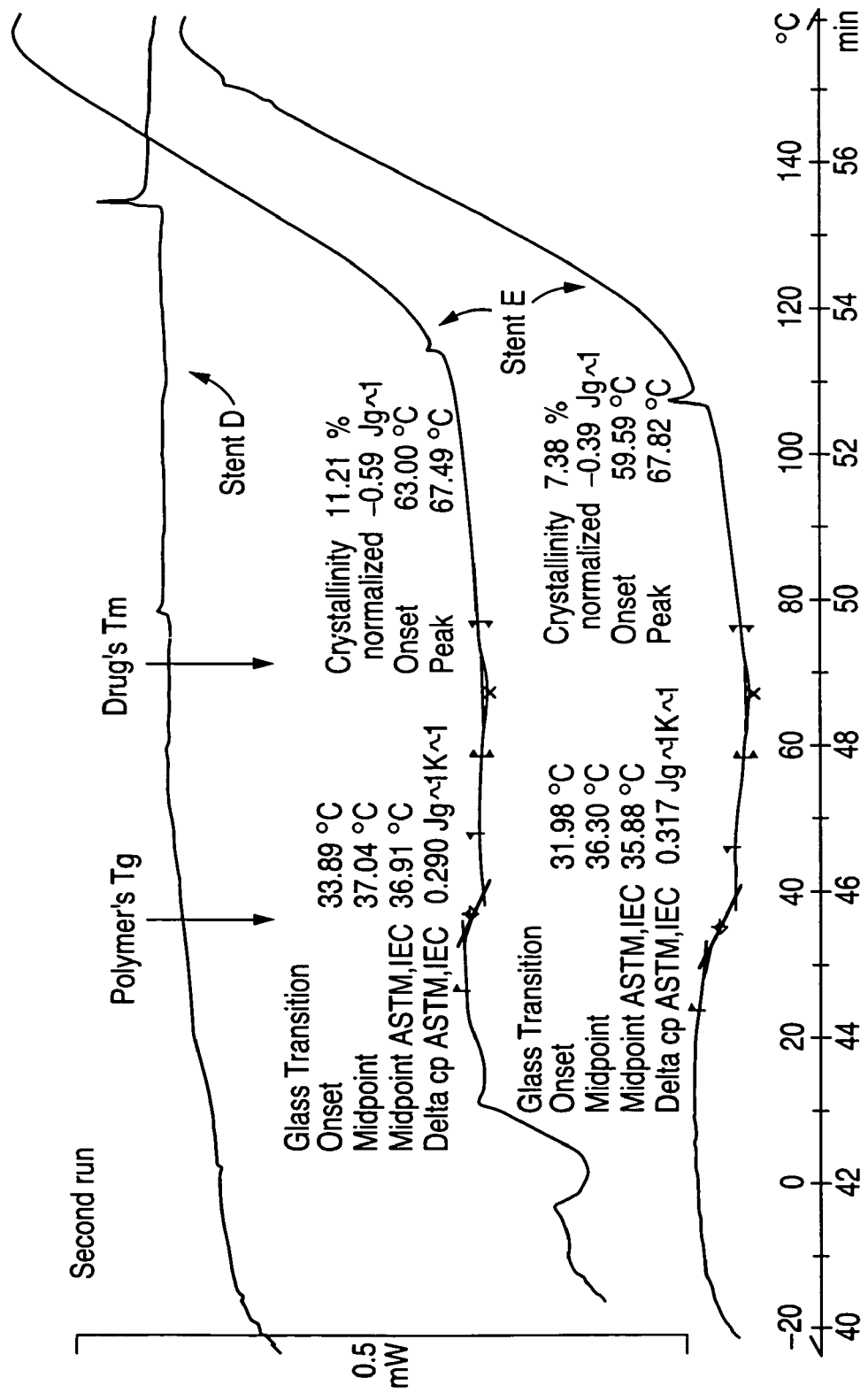

A Vision™ stent was provided ("Stent D"). A coating was formed on a Vision™ stent to include everolimus/DLPLA ("Stent E"). Stents D and E were studied using the above mentioned DSC for two runs. During the first run, the samples were heated slightly above the $T_g$ of the polymeric component to remove the relaxation peak. The results from the first run are illustrated in FIG. 23. During the second run, as shown illustrated in FIG. 24, the polymeric coating of Stent E exhibited a $T_g$ for the polymer at about 36° C. The $T_m$ of the drug was shown to be about 67° C.

While particular embodiments of the present invention have been shown and described, it will be obvious to those skilled in the art that changes and modifications can be made without departing from this invention in its broader aspects.

Therefore, the appended claims are to encompass within their scope all such changes and modifications as fall within the true spirit and scope of this invention.

What is claimed is:

1. A method of manufacturing an implantable medical device, comprising:
   applying a semicrystalline polymer to the implantable medical device; and
   exposing the polymer to a temperature equal to the crystallization temperature of the polymer for a duration of time.

2. The method of claim 1, wherein the polymer comprises poly(lactic acid).

3. The method of claim 1, wherein the polymer comprises a block copolymer or a graft copolymer, and wherein a moiety of the block copolymer or the graft copolymer is poly(lactic acid).

4. A method of applying a polymeric coating to an implantable medical device, comprising:
   applying to the implantable medical device a composition comprising a polymer and a solvent to form the polymeric coating on the implantable medical device, and
   exposing the device to a temperature equal to or greater than the glass transition temperature of the polymer and less than the melting temperature of the polymer for a duration of time, wherein the temperature is
   (a) equal to the glass transition temperature of the polymer plus the melting temperature of the polymer, divided by 2;
   (b) equal to 0.9 times the melting temperature of the polymer, wherein the melting temperature of the polymer is expressed in Kelvin;
   (c) equal to or greater than the crystallization temperature of the polymer; or
   (d) equal to the glass transition temperature of the polymer.

5. A method of applying a polymeric coating to an implantable medical device, comprising:
   applying to the implantable medical device a composition comprising a polymer and a solvent to form the polymeric coating on the implantable medical device, and
   exposing the device to a temperature equal to or greater than the glass transition temperature of the polymer and less than the melting temperature of the polymer for a duration of time, wherein the polymer comprises a block copolymer or a graft copolymer;
   wherein a moiety of the block copolymer or the graft copolymer is poly(lactic acid);
   and wherein the glass transition temperature is above room temperature.

6. A method of applying a polymeric coating to an implantable medical device, comprising:
   applying to the implantable medical device a composition comprising a polymer and a solvent to form the polymeric coating on the implantable medical device, and
   exposing the device to a temperature equal to the glass transition temperature of the polymer for a duration of time, wherein the device is a stent and wherein the act of exposing the device to the temperature is done concurrently with or subsequent to securing the stent onto a patient delivery device.

7. A method of applying a polymeric coating to an implantable medical device, comprising:
   applying to the implantable medical device a composition comprising a polymer and a solvent to form the polymeric coating on the implantable medical device, and
   exposing the device to a temperature equal to the glass transition temperature of the polymer for a duration of time, wherein the device is a stent and wherein the act of exposing the device to the temperature is done concurrently with crimping of the stent onto a catheter.

8. A method of applying a polymeric coating to an implantable medical device, comprising:
   applying to the implantable medical device a composition comprising a polymer and a solvent to form the polymeric coating on the implantable medical device, and
   exposing the device to a temperature equal to or greater than the glass transition temperature of the polymer and less than the melting temperature of the polymer for a duration of time, wherein during the act of exposing the device to the temperature, the temperature is changed to another temperature between the glass transition temperature and the melting temperature.

9. The method of claim 8, wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), random and block copolymers of α-methylstyrene and vinyl acetate, random and block copolymers of α-methylstyrene and vinyl chloride, random and block copolymers of α-methylstyrene and styrene, random and block copolymers of styrene and butyl methacrylate, random and block copolymers of styrene and methyl methacrylate, random and block copolymers of styrene and ethylene oxide, random and block copolymers of styrene and isoprene, random and block copolymers of styrene and isobutylene, random and block copolymers of methyl methacrylate and ethyl acrylate, random and block copolymers of methyl methacrylate and vinyl acetate, random and block copolymers of methyl methacrylate and ethyl methacrylate, and any combination thereof.

10. The method of claim 9, wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), and any combination thereof.

11. The method of claim 8, wherein the polymer exhibits more than one glass transition temperature, and the exposure temperature is above the lowest of the glass transition temperatures.

12. The method of claim 8, wherein the polymer exhibits more than one glass transition temperature, and the exposure temperature is above the highest of the glass transition temperatures.

13. The method of claim 8, wherein the composition additionally comprises a second polymer such that the coating formed comprises a polymer blend, and the exposure temperature is above the lowest of the glass transition temperatures if the polymer blend exhibits more than one glass transition temperature.

14. The method of claim 13, wherein the exposure temperature is less than the lowest melting temperature if the polymer blend exhibits more than one melting temperature.

15. The method of claim 8, wherein the composition additionally comprises a second polymer such that the coating formed comprises a polymer blend, and the exposure temperature is above the highest of the glass transition temperatures if the polymer blend exhibits more than one glass transition temperature.

16. The method of claim 15, wherein the exposure temperature is less than the lowest melting temperature if the polymer blend exhibits more than one melting temperature.

17. The method of claim 8, wherein the duration of time is sufficient to improve the mechanical properties of the coating.

18. The method of claim 8, wherein the polymeric coating is free from any active agents and the polymeric coating comprises a primer layer.

19. The method of claim 18, wherein the implantable medical device is made of a metal, a metallic material, or a metal alloy.

20. The method of claim 19, wherein the duration of time is sufficient to improve the mechanical properties of the primer layer.

21. A method of coating an implantable medical device, comprising:
    applying a first layer to the device comprising a first polymer having a first glass transition temperature;
    applying a second layer over the first layer, the second layer comprising a second polymer having a second glass transition temperature; and
    exposing the device to a temperature between the first glass transition temperature and the second glass transition temperature.

22. The method of claim 21, wherein the first glass transition temperature is higher than the second glass transition temperature.

23. The method of claim 21, wherein the first glass transition temperature is lower than the second glass transition temperature.

24. The method of claim 21, wherein at least one of the layers comprises a drug.

25. The method of claim 21, wherein the first and the second polymers are selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), random and block copolymers of α-methylstyrene and vinyl acetate, random and block copolymers of α-methylstyrene and vinyl chloride, random and block copolymers of α-methylstyrene and styrene, random and block copolymers of styrene and butyl methacrylate, random and block copolymers of styrene and methyl methacrylate, random and block copolymers of styrene and ethylene oxide, random and block copolymers of styrene and isoprene, random and block copolymers of styrene and isobutylene, random and block copolymers of methyl methacrylate and thyl acetate, random and block copolymers of methyl methacrylate and vinyl acetate, random and block copolymers of methyl methacrylate and ethyl methacrylate, and any combination thereof.

26. The method of claim 24, wherein at least one of the first and the second polymers is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), and any combination thereof.

27. The method of claim 21, wherein both the first and second glass transition temperatures are above room temperature.

28. A method of coating an implantable medical device, comprising:
    applying a coating to the device, the coating comprising a polymer; and
    exposing the coating to a temperature treatment so as to modify % crystallinity of the polymer such that the shallower regions of the coating will have a higher % of crystallinity than the deeper regions of the coating.

29. A method of applying a polymeric coating to an implantable medical device, comprising:
    applying to the implantable medical device a composition comprising a polymer and a solvent to form the polymeric coating on the implantable medical device, and
    exposing the device to a temperature equal to the glass transition temperature of the polymer for a duration of time;
    wherein the glass transition temperature is not equal to room temperature.

30. The method of claim 29, wherein the polymer comprises a bioabsorbable polymer.

31. The method of claim 29, wherein the polymer comprises poly(lactic acid).

32. The method of claim 29, wherein the polymer comprises a block copolymer or a graft copolymer, and wherein a moiety of the block copolymer or the graft copolymer is poly(lactic acid).

33. The method of claim 29, wherein the device is a stent and wherein the act of exposing the device to the temperature is done concurrently with or subsequent to securing the stent onto a patient delivery device.

34. The method of claim 29, wherein the device is a stent and wherein the act of exposing the device to the temperature is done concurrently with crimping of the stent onto a catheter.

35. The method of claim 29, wherein the composition additionally comprises rapamycin, everolimus or functional analogs or structural derivatives thereof.

36. The method of claim 29, wherein the glass transition temperature is above room temperature.

37. The method of claim 29, wherein the composition additionally comprises a drug.

38. A method of applying a polymeric coating to an implantable medical device, comprising:
    applying to the implantable medical device a composition comprising a polymer and a solvent to form the polymeric coating on the implantable medical device, and
    exposing the device to a temperature equal to the glass transition temperature of the polymer for a duration of time;
    wherein the polymeric coating is free from any active agents.

39. The method of claim 38, wherein the glass transition temperature is above room temperature.

40. A method of applying a polymeric coating to an implantable medical device, comprising:
    applying to the implantable medical device a composition comprising a polymer and a solvent to form the polymeric coating on the implantable medical device, and
    exposing the device to a temperature equal to the glass transition temperature of the polymer for a duration of time;
    wherein the polymer comprises a crystalline component and an amorphous component such that the temperature is equal to the glass transition temperature of either of the components.

41. A method of applying a polymeric coating to an implantable medical device, comprising:
    applying to the implantable medical device a composition comprising a polymer and a solvent to form the polymeric coating on the implantable medical device, and exposing the device to a temperature equal to or greater than the glass transition temperature of the polymer and less than the melting temperature of the polymer for a duration of time, wherein the device is a stent and wherein the act of exposing the device to the temperature is done concurrently with or subsequent to securing the stent onto a patient delivery device; and wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), random and block copolymers of α-methylstyrene and vinyl acetate, random and block copolymers of α-methylstyrene and vinyl chloride, random and block copolymers of α-methylstyrene and styrene, random and block copolymers of styrene and butyl methacrylate, random and block copolymers of styrene and methyl methacrylate, random and block copolymers of styrene and ethylene oxide, random and block copolymers of styrene and isoprene, random and block copolymers of styrene and isobutylene, random and block copolymers of methyl methacrylate and ethyl acrylate, random and block copolymers of methyl methacrylate and vinyl acetate, random and block copolymers of methyl methacrylate and ethyl methacrylate, and any combination thereof.

42. The method of claim 41, wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), and any combination thereof.

43. A method of applying a polymeric coating to an implantable medical device, comprising:

applying to the implantable medical device a composition comprising a polymer and a solvent to form the polymeric coating on the implantable medical device, and exposing the device to a temperature equal to or greater than the glass transition temperature of the polymer and less than the melting temperature of the polymer for a duration of time, wherein the device is a stent and wherein the act of exposing the device to the temperature is done concurrently with crimping of the stent onto a catheter; and wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), random and block copolymers of α-methylstyrene and vinyl acetate, random and block copolymers of α-methylstyrene and vinyl chloride, random and block copolymers of α-methylstyrene and styrene, random and block copolymers of styrene and butyl methacrylate, random and block copolymers of styrene and methyl methacrylate, random and block copolymers of styrene and ethylene oxide, random and block copolymers of styrene and isoprene, random and block copolymers of styrene and isobutylene, random and block copolymers of methyl methacrylate and ethyl acrylate, random and block copolymers of methyl methacrylate and vinyl acetate, random and block copolymers of methyl methacrylate and ethyl methacrylate, and any combination thereof.

44. The method of claim 43, wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), and any combination thereof.

45. A method of applying a polymeric coating to an implantable medical device, comprising:

applying to the implantable medical device a composition comprising a polymer and a solvent to form the polymeric coating on the implantable medical device, and exposing the device to a temperature greater than the glass transition temperature of the polymer and less than the melting temperature of the polymer for a duration of time;

wherein the glass transition temperature is above room temperature; and wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon caprolactone), random and block copolymers of α-methylstyrene and vinyl acetate, random and block copolymers of α-methylstyrene and vinyl chloride, random and block copolymers of α-methylstyrene and styrene, random and block copolymers of styrene and butyl methacrylate, random and block copolymers of styrene and methyl methacrylate, random and block copolymers of styrene and ethylene oxide, random and block copolymers of styrene and isoprene, random and block copolymers of styrene and isobutylene, random and block copolymers of methyl methacrylate and ethyl acrylate, random and block copolymers of methyl methacrylate and vinyl acetate, random and block copolymers of methyl methacrylate and ethyl methacrylate, and any combination thereof.

46. The method of claim 45, wherein the polymer is selected from the group consisting of ethylene vinyl alcohol copolymer, poly(n-butyl methacrylate), poly(ethylene-co-vinyl acetate), poly(ethylene terephthalate), poly(vinylidene fluoride), poly(p-phenylene sulfide), poly(6-aminocaproic acid), poly(methyl methacrylate), poly(vinyl alcohol), poly(epsilon carpolactone), and any combination thereof.

47. A method of applying a polymeric coating to an implantable medical device, comprising:

applying to the implantable medical device a composition comprising a polymer and a solvent to form the polymeric coating on the implantable medical device, and exposing the device to a temperature greater than the glass transition temperature of the polymer and less than the melting temperature of the polymer for a duration of time;

wherein the glass transition temperature is above room temperature; and wherein the polymer exhibits more than one glass transition temperature, and the exposure temperature is above the highest of the glass transition temperatures.

48. A method of applying a polymeric coating to an implantable medical device, comprising:

applying to the implantable medical device a composition comprising a first polymer, a second polymer, and a solvent to form the polymeric coating on the implantable medical device, the coating formed comprising a polymer blend; and exposing the device to a temperature greater than the glass transition temperature of the polymer blend and less than the melting temperature of the polymer blend for a duration of time;

wherein the glass transition temperature is above room temperature; and wherein the exposure temperature is above the lowest of the glass transition temperatures if the polymer blend exhibits more than one glass transition temperature.

49. The method of claim 48, wherein the exposure temperature is less than the lowest melting temperature if the polymer blend exhibits more than one melting temperature.

50. A method of applying a polymeric coating to an implantable medical device, comprising:

applying to the implantable medical device a composition comprising a first polymer, a second polymer, and a solvent to form the polymeric coating on the implantable medical device, the coating formed comprising a polymer blend; and exposing the device to a temperature greater than the glass transition temperature of the polymer blend and less than the melting temperature of the polymer blend for a duration of time;

wherein the glass transition temperature is above room temperature; and wherein the exposure temperature is above the highest of the glass transition temperatures if the polymer blend exhibits more than one glass transition temperature.

51. The method of claim 50, wherein the exposure temperature is less than the lowest melting temperature if the polymer blend exhibits more than one melting temperature.

52. A method of applying a coating to an implantable medical device, comprising:

applying to the implantable medical device a composition comprising a polymer and a solvent to form a polymeric primer layer free from any active agents on the implantable medical device; and exposing the device to a temperature greater than the glass transition temperature of the polymer and less than the melting temperature of the polymer for a duration of time;

wherein the glass transition temperature is above room temperature; and wherein the duration of time is sufficient to improve the mechanical properties of the primer layer; and after the exposure to the temperature, applying a second composition comprising a second polymer, which may be the same as or different from the polymer of the primer layer, and a solvent, which may be the same as or different from the solvent in the composition used to apply the primer layer, to form a second polymeric coating layer on the implantable medical device; and wherein the exposure of the device to a temperature greater than the glass transition temperature of the polymer of the primer layer and less than the melting temperature of the polymer of the primer layer for a duration of time increase the effectiveness of the primer as an adhesive tie layer between the device and the second polymeric coating layer.

53. The method of claim 52 wherein the second composition further comprises a drug.

54. A method of applying a polymeric coating to an implantable medical device, comprising:

applying to the implantable medical device a composition comprising a polymer and a solvent to form the polymeric coating on the implantable medical device;

exposing the device to a temperature equal to or greater than the glass transition temperature of the polymer and less than the melting temperature of the polymer for a duration of time, wherein the polymer comprises a bioabsorbable polymer and wherein the glass transition temperature is above room temperature; and wherein the bioabsorbable polymer is selected from the group consisting of poly(hydroxybutyrate) (PHB), poly(hydroxyvalerate) (PHV), poly(hydroxybutyrate-co-valerate), poly(caprolactone) (PCL), poly(lactide-co-glycolide) (PLGA), poly(glycerol-sebacate) (PGS), poly(ester amide), collagen, elastin, silk, AB and ABA block-copolymers of PEG with poly(butylene terephthalate) (PBT), poly(ethylene-glycol)-block-poly(butylene terephthalate) (PEG-PBT), poly(ethylene-glycol)-block-poly (butylene terephthalate)-block-poly(ethylene-glycol) (PEG-PBT-PEG), poly(butylene terephthalate)-block-poly(ethylene-glycol)-block poly(butylene terephthalate) (PBT-PEG-PBT), AB and ABA block-copolymers of PEG with PCL, poly(ethylene-glycol)-block-poly(caprolactone) (PEG-PCL), poly(ethylene-glycol)-block-poly(caprolactone)-block-poly(ethylene-glycol) (PEG-PCL-PEG), poly(caprolactone)-block-poly(ethylene-glycol)block-poly(caprolactone) (PCL-PEG-PCL), and any combination thereof.

* * * * *